(12) United States Patent
Padmanabhan et al.

(10) Patent No.: US 8,323,564 B2
(45) Date of Patent: Dec. 4, 2012

(54) PORTABLE SAMPLE ANALYZER SYSTEM

(75) Inventors: Aravind Padmanabhan, Plymouth, MN (US); James A. Cox, New Brighton, MN (US); Bernard S. Fritz, Eagan, MN (US); Tom M. Rezachek, Cottage Grove, MN (US); Peter L. Reutiman, Crystal, MN (US); Ron L. Bardell, St. Louis Park, MN (US); Cleopatra Cabuz, Eden Prairie, MN (US)

(73) Assignee: Honeywell International Inc., Morristown, NJ (US)

( * ) Notice: Subject to any disclaimer, the term of this patent is extended or adjusted under 35 U.S.C. 154(b) by 1489 days.

(21) Appl. No.: 11/615,874

(22) Filed: Dec. 22, 2006

(65) Prior Publication Data

US 2007/0172388 A1    Jul. 26, 2007

Related U.S. Application Data

(60) Continuation-in-part of application No. 10/908,460, filed on May 12, 2005, and a continuation-in-part of application No. 10/908,461, filed on May 12, 2005, now Pat. No. 7,641,856, and a continuation-in-part of application No. 11/306,508, filed on Dec. 30, 2005, which is a continuation-in-part of application No. 10/950,898, filed on Sep. 27, 2004, now Pat. No. 7,130,046, application No. 11/615,874, which is a continuation-in-part of application No. 10/938,265, filed on Sep. 9, 2004, now Pat. No. 7,630,063, application No. 11/615,874, which is a continuation-in-part of application No. 11/306,508, which is a continuation-in-part of application No. 10/908,460, application No. 11/615,874, which is a continuation-in-part of application No. 11/306,508, which is a continuation-in-part of application No. 10/908,014, filed on Apr. 25, 2005, which is a (Continued)

(51) Int. Cl.
*G01N 21/00* (2006.01)
*B01L 3/00* (2006.01)
(52) U.S. Cl. ......................................... 422/63; 422/502
(58) Field of Classification Search .................. 422/502, 422/63
See application file for complete search history.

(56) References Cited

U.S. PATENT DOCUMENTS 3,822,095 A    7/1974    Hirshfield
(Continued)

FOREIGN PATENT DOCUMENTS

DE    10122321    4/2002
(Continued)

OTHER PUBLICATIONS http://www.micronics.net/tsensor.htm, pp. 1-4, downloaded Jun. 14, 2000.

(Continued)

*Primary Examiner* — Lore Jarrett
(74) *Attorney, Agent, or Firm* — Seager Tufte & Wickhem LLC.

(57) ABSTRACT

A system relating to sample analyzers, and more particular, to sample analyzers that are simple to operate and have a reduced risk of providing an erroneous result to a user. In some cases, the sample analyzer may be a portable sample analyzer that includes a disposable fluidic cartridge. The operators of the analyzers need not be trained.

14 Claims, 35 Drawing Sheets

Related U.S. Application Data

(60) continuation-in-part of application No. 10/304,773, filed on Nov. 26, 2002, which is a continuation-in-part of application No. 09/630,924, filed on Aug. 2, 2000, now Pat. No. 6,597,438, application No. 11/615,874, which is a continuation-in-part of application No. 11/306,508, which is a continuation-in-part of application No. 10/908,014, which is a continuation-in-part of application No. 10/908,685, filed on Nov. 3, 2004, which is a division of application No. 10/174,851, filed on Jun. 19, 2002, now Pat. No. 6,837,476, application No. 11/615,874, which is a continuation-in-part of application No. 11/306,508, which is a continuation-in-part of application No. 10/908,014, which is a continuation-in-part of application No. 10/340,231, filed on Jan. 10, 2003, now Pat. No. 6,889,567, which is a division of application No. 09/586,093, filed on Jun. 2, 2000, now Pat. No. 6,568,286, application No. 11/615,874, which is a continuation-in-part of application No. 11/306,508, which is a continuation-in-part of application No. 10/950,898, application No. 11/615,874, which is a continuation-in-part of application No. 11/306,508, which is a continuation-in-part of application No. 10/938,265, which is a continuation-in-part of application No. 10/304,773, which is a continuation-in-part of application No. 09/630,924, application No. 11/615,874, which is a continuation-in-part of application No. 11/306,508, which is a continuation-in-part of application No. 10/938,265, which is a continuation-in-part of application No. 10/225,325, filed on Aug. 21, 2002, now Pat. No. 6,970,245, application No. 11/615,874, which is a continuation-in-part of application No. 11/306,508, which is a continuation-in-part of application No. 10/932,662, filed on Sep. 2, 2004, application No. 11/615,874, which is a continuation-in-part of application No. 11/306,508, which is a continuation-in-part of application No. 10/899,607, filed on Jul. 15, 2004, application No. 11/615,874, which is a continuation-in-part of application No. 11/306,508, which is a continuation-in-part of application No. 10/938,245, filed on Sep. 9, 2004, which is a continuation of application No. 10/824,859, filed on Apr. 14, 2004, which is a continuation-in-part of application No. 10/225,325, which is a continuation-in-part of application No. 09/630,927, filed on Aug. 2, 2000, now Pat. No. 6,549,275, application No. 11/615,874, which is a continuation-in-part of application No. 11/306,508, which is a continuation-in-part of application No. 10/759,875, filed on Jan. 16, 2004, which is a continuation-in-part of application No. 09/896,230, filed on Jun. 29, 2001, now Pat. No. 6,700,130, application No. 11/615,874, which is a continuation-in-part of application No. 11/306,508, which is a continuation-in-part of application No. 10/759,875, which is a continuation-in-part of application No. 10/304,773, application No. 11/615,874, which is a continuation-in-part of application No. 11/306,508, which is a continuation-in-part of application No. 10/304,773, which is a continuation-in-part of application No. 09/630,924, application No. 11/615,874, which is a continuation-in-part of application No. 11/306,508, which is a continuation-in-part of application No. 10/908,014, which is a continuation-in-part of application No. 10/953,197, filed on Sep. 28, 2004, application No. 11/615,874, which is a continuation-in-part of application No. 11/306,508, which is a continuation-in-part of application No. 11/027,134, filed on Dec. 30, 2004, which is a continuation-in-part of application No. 10/304,773, which is a continuation-in-part of application No. 09/630,924, application No. 11/615,874, which is a continuation-in-part of application No. 11/306,508, which is a continuation-in-part of application No. 11/306,402, filed on Dec. 27, 2005.

(60) Provisional application No. 60/753,293, filed on Dec. 22, 2005, provisional application No. 60/755,014, filed on Dec. 29, 2005, provisional application No. 60/571,235, filed on May 14, 2004.

U.S. PATENT DOCUMENTS

| Patent No. | | Date | Inventor(s) | |
|---|---|---|---|---|
| 3,928,094 | A | 12/1975 | Angell | |
| 3,976,862 | A | 8/1976 | Curbelo | |
| 4,284,412 | A | 8/1981 | Hansen et al. | |
| 4,430,299 | A | * 2/1984 | Horne | 422/64 |
| 4,478,076 | A | 10/1984 | Bohrer | |
| 4,478,077 | A | 10/1984 | Boher | |
| 4,501,144 | A | 2/1985 | Higashi et al. | |
| 4,599,000 | A | 7/1986 | Yasuyoshi | |
| 4,651,564 | A | 3/1987 | Johnson et al. | |
| 4,683,159 | A | 7/1987 | Bohrer et al. | |
| 4,695,034 | A | 9/1987 | Shimizu et al. | |
| 4,704,033 | A | 11/1987 | Fay et al. | |
| 4,745,279 | A | 5/1988 | Karkar et al. | |
| 4,818,263 | A | 4/1989 | Mitch | |
| 4,874,949 | A | 10/1989 | Harris et al. | |
| 4,911,616 | A | 3/1990 | Laumann, Jr. | |
| 4,932,989 | A | 6/1990 | Presby | |
| 4,980,292 | A | 12/1990 | Elbert et al. | |
| 5,017,497 | A | 5/1991 | de Grooth et al. | |
| 5,050,429 | A | 9/1991 | Nishimoto et al. | |
| 5,078,581 | A | 1/1992 | Blum et al. | |
| 5,082,242 | A | 1/1992 | Bonne et al. | |
| 5,085,562 | A | 2/1992 | van Lintel | |
| 5,096,388 | A | 3/1992 | Weinberg | |
| 5,108,623 | A | 4/1992 | Cangelosi et al. | |
| 5,129,794 | A | 7/1992 | Beatty | |
| 5,171,132 | A | 12/1992 | Miyazaki et al. | |
| 5,176,358 | A | 1/1993 | Bonne et al. | |
| 5,185,641 | A | 2/1993 | Igushi et al. | |
| 5,194,909 | A | 3/1993 | Tycko | |
| 5,219,278 | A | 6/1993 | van Lintel | |
| 5,224,843 | A | 7/1993 | van Lintel | |
| 5,244,537 | A | 9/1993 | Ohnstein | |
| 5,323,999 | A | 6/1994 | Bonne et al. | |
| 5,441,597 | A | 8/1995 | Bonne et al. | |
| 5,452,878 | A | 9/1995 | Gravesen et al. | |
| 5,457,526 | A | 10/1995 | Kosaka | |
| 5,510,267 | A | 4/1996 | Marshall | |
| 5,528,045 | A | 6/1996 | Hoffman et al. | |
| 5,570,193 | A | 10/1996 | Landa et al. | |
| 5,601,080 | A | 2/1997 | Oppenheimer | |
| 5,616,501 | A | 4/1997 | Rodriguez | |
| 5,633,724 | A | 5/1997 | King et al. | |
| 5,683,159 | A | 11/1997 | Johnson | |
| 5,716,852 | A | 2/1998 | Yager et al. | |
| 5,717,631 | A | 2/1998 | Carley et al. | |
| 5,726,751 | A | 3/1998 | Altendorf et al. | |
| 5,757,476 | A | 5/1998 | Nakamoto et al. | |
| 5,760,900 | A | 6/1998 | Ito et al. | |
| 5,793,485 | A | 8/1998 | Gourley | |
| 5,799,030 | A | 8/1998 | Brenner | |
| 5,822,170 | A | 10/1998 | Cabuz et al. | |
| 5,836,750 | A | 11/1998 | Cabuz | |
| 5,837,547 | A | 11/1998 | Schwartz | |

| | | |
|---|---|---|
| 5,839,807 A | 11/1998 | Perlo |
| 5,858,195 A | 1/1999 | Ramsey |
| 5,863,502 A | 1/1999 | Southgate et al. |
| 5,880,474 A | 3/1999 | Norton et al. |
| 5,893,722 A | 4/1999 | Hibbs-Brennen et al. |
| 5,901,939 A | 5/1999 | Cabuz et al. |
| 5,922,210 A | 7/1999 | Brody et al. |
| 5,932,100 A | 8/1999 | Yager et al. |
| 5,948,684 A | 9/1999 | Weigl et al. |
| 5,970,315 A | 10/1999 | Carley et al. |
| 5,971,158 A | 10/1999 | Yager et al. |
| 5,972,710 A | 10/1999 | Weigl et al. |
| 5,974,867 A | 11/1999 | Forster et al. |
| 5,989,402 A * | 11/1999 | Chow et al. .................. 204/601 |
| 6,007,775 A | 12/1999 | Yager |
| 6,032,689 A | 3/2000 | Tsai et al. |
| 6,054,335 A | 4/2000 | Sun et al. |
| 6,082,185 A | 7/2000 | Saaski |
| 6,091,197 A | 7/2000 | Sun et al. |
| 6,091,537 A | 7/2000 | Sun et al. |
| 6,094,293 A | 7/2000 | Yokoyama et al. |
| 6,097,485 A | 8/2000 | Lievan |
| 6,097,859 A | 8/2000 | Solgaard et al. |
| 6,106,245 A | 8/2000 | Cabuz |
| 6,109,889 A | 8/2000 | Zengerie et al. |
| 6,116,756 A | 9/2000 | Peeters et al. |
| 6,124,663 A | 9/2000 | Haake et al. |
| 6,139,800 A | 10/2000 | Chandler |
| 6,179,586 B1 | 1/2001 | Herb et al. |
| 6,184,607 B1 | 2/2001 | Cabuz et al. |
| 6,197,494 B1 * | 3/2001 | Oberhardt .................. 435/4 |
| 6,215,221 B1 | 4/2001 | Cabuz et al. |
| 6,237,619 B1 | 5/2001 | Maillefer et al. |
| 6,240,944 B1 | 6/2001 | Ohnstein et al. |
| 6,249,341 B1 | 6/2001 | Basiji et al. |
| 6,281,975 B1 | 8/2001 | Munk |
| 6,382,228 B1 * | 5/2002 | Cabuz et al. .................. 137/10 |
| 6,524,790 B1 | 2/2003 | Kopf-Sill et al. |
| 6,549,275 B1 | 4/2003 | Cabuz et al. |
| 6,597,438 B1 | 7/2003 | Cabuz et al. |
| 2002/0028434 A1 * | 3/2002 | Goix et al. .................. 435/4 |
| 2003/0057968 A1 | 3/2003 | Wang et al. |
| 2003/0142291 A1 | 7/2003 | Padmanabhan et al. |
| 2004/0065143 A1 | 4/2004 | Husher |
| 2004/0109386 A1 | 6/2004 | Gold et al. |
| 2004/0154933 A1 | 8/2004 | Cosofret |
| 2004/0155309 A1 * | 8/2004 | Sorin et al. .................. 257/433 |
| 2004/0211077 A1 | 10/2004 | Schwichtenberg |
| 2004/0233424 A1 | 11/2004 | Lee et al. |
| 2005/0105077 A1 | 5/2005 | Padmanabhan et al. |
| 2005/0255600 A1 | 11/2005 | Padmanabhan et al. |

FOREIGN PATENT DOCUMENTS

| | | |
|---|---|---|
| EP | 0269076 | 6/1988 |
| EP | 0483117 | 4/1992 |
| EP | 0694784 | 1/1996 |
| EP | 1001326 | 5/1999 |
| EP | 1134548 | 9/2001 |
| EP | 1359419 | 5/2003 |
| JP | 60082865 | 12/1983 |
| JP | 61066947 | 4/1986 |
| JP | 10073528 | 3/1998 |
| JP | 2000056228 | 2/2000 |
| JP | 2004257756 | 9/2004 |
| WO | 9527199 | 10/1995 |
| WO | 9960397 | 11/1999 |
| WO | 0109598 | 2/2001 |
| WO | 0210713 | 2/2002 |
| WO | 0210714 | 2/2002 |
| WO | 2004059316 | 7/2004 |
| WO | 2005090983 | 9/2005 |
| WO | 2005108963 | 11/2005 |
| WO | 2005114142 | 12/2005 |
| WO | 2005114144 | 12/2005 |

OTHER PUBLICATIONS http://www.micronics.net/hfilter.htm, pp. 1-3, downloaded Jun. 14, 2000.
http://www.micronics.net/mcytometry.htm, pp. 1-4, downloaded Jun. 14, 2000.
http://www.micronics.net/orcafluidics.htm, pp. 1-4, downloaded Jun. 14, 2000.
Altendorf et al, "Results Obtained Using a Prototype Microfluidics-Based Hematology Analyzer", SPIE Biomedical Optics 97, 1997.
Altendorf et al., "Differential Blood Cell Counts Obtained Using a Microchannel Based Flow Cytometer", Solid State Sensors & Actuators, vol. 1, 531, 1997.
Altendorf et al., "Implementation of Novel Optical Detection Methods for Clinically Important Blood Analytes Using Microfabricated Flow Structures (T-Sensors™)", MicroTAS 98, Banff, Canada, Apr. 1998.
Altendorf et al., "Microfabrication Technology for Research and Diagnostics, Silicon Microchannel Optical Flow Cytometry", SPIE Proceedings, Biomedical Optics 96, Jan. 1996.
Cabuz et al., "Mesoscopic Sampler Based on 3D Array of Electrostatically Activated Diaphragms", The 10th Int. Conf. on Solid-State Sensors and Actuators, Transducers'99, Jun. 7-12, 1999, Sendai Japan, p. 1890-1.
Darling et al., "Integration of Microelectrodes With Etched Microchannels for In-Stream Electrochemical Analysis", MicroTAS 98, Banff, Canada, Apr. 1998.
Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.
Hatch et al., "Microfluidic Approaches to Immunoassays", SPIE conference on Micromachining and Microfabrication Symposium at Santa Clara, CA, Sep. 20-22, 1999.
Huang et al., "Development of a Flow Cytometry Based Miniature Chemical Fluid Analysis System Using Fluorescent Microbeads", SPIE Biomedical Optics, BIOS 97, conference proceedings, 1997.
Lehman et al., "High-Frequency Modulation Characteristics of Red VCSELs", Electronics Letters, Feb. 13, 1997, vol. 33(4), pp. 298-300. Copyright 1997 IEEE.
Ohnstein et al., "Micromachined Silicon Microvalve", Proceedings of MEMS, 1990, IEEE Micro Electromechanical Systems, Napa Valley, California, Feb. 11-14, 1990, pp. 95-98.
Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.
Shapiro, "Practical Flow Cytometry", third edition, 1995, p. 237.
Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.
Terstappen et al., "Four-Parameter White Blood Cell Differential Counting Based on Light Scattering Measurements", Alan R. Liss, Inc., Cytometry 9:39-43, 1988.
Toshiyoshi et al., "Micromechanical Lens Scanner for Fiber Optic Switches", Proc. 3rd International Conference on Micro Opto Electro Mechanical Systems (MOEMS 99), Aug. 30-Sep. 1, 1999, Mainz, Germany, pp. 165-170.
Toshiyoshi et al., "Surface micromachined 2D Lens Scanner Array", Proc. IEEE?LEOS International Coference on Optical EMMS/Sheraton Kauai Resort, Kauai, Hawaii, Aug. 21-24, 2000, 3 pages.
Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.
Tuantranont et al., "MEMS-Controllable Microlens Array for Beam Steering and Precision Alignment in Optical Interconnect Systems", Solid-State Sensor and Actuator Workshop, Hilton Head Island, South Carolina, Jun. 4-8, 2000, pp. 101-104.
Weigl et al, "Silicon-Microfabricated Diffusion-Based Optical Chemical Sensor", Reprint from "Sensors & Actuators" B 38-39, 452-457, 1997.
Weigl et al, "Microfluidic Diffusion-Based Separation and Detection", Science, vol. 283, pp. 346-347, Jan. 15, 1999.

Weigl et al, "Optical and Electrochemical Diffusion-Based Detection of Analytes in Complex Samples Using Microfabricated Flow Structures (T-SensorSTM)", Micro- and nanofabn'cated electro-optical mechanical systems for biomedical and environmental applications II-SPIE vol. 3606, Jan. 25-26, 1999.

Weigl et al, "Simultaneous Self-Referencing Analyte Determination in Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection in Silicon Flow Structures", Analytical Methods & Instrumentation, μTTAS 96 special edition, 1996.

Weigl et al., "Fluorescence and Absorbance Analyte Sensing in Whole Blood and Plasma Based on Diffusion Separation in Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", μTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Yager et al., "Applying Microfluidic Chemical Analytical Systems to Imperfect Samples", Micro Total Analysis Systems 98, D. Harrison & A. van den Berg (ed.), Kluwer Academic Publishers, Dordrecht, 207-212, 1998.

Yager et al., "Design of Microfluidic Sample Preconditioning Systems for Detection of Biological Agents in Environmental Samples", Yager, M. et al., SPIE Proceedings, 3515, 252-259, 1998.

HemoCue Hb 201+, Operating Manual, pp. 1-41, prior to Dec. 2006.

Lamvik et al., Nonlabeled Secondary Antibodies Augment/Maintain the Binding of Primary, Specific Antibodies to Cell Membrande Antigens, Cytometery 45, pp. 187-193, 2001.

* cited by examiner

| Fluid | Volume displaced {µl} | Stroke of displacer {mm} | Diameter of storage cavity {mm} |
|---|---|---|---|
| Sample pusher fluid | 8 | 1.1 | 3.4 |
| Lysing solution | 120 | 2.8 | 8.3 |
| Sphering solution | 300 | 3.8 | 11.3 |
| Sheath fluid | 1800 | 6.9 | 20 |

Figure 9G

PORTABLE SAMPLE ANALYZER SYSTEM

This application claims the benefit of U.S. Provisional Patent Application 60/753,293 filed Dec. 22, 2005.

This application claims the benefit of U.S. Provisional Patent Application 60/755,014, filed Dec. 29, 2005.

This application is a continuation-in-part application of U.S. patent application Ser. No. 10/908,460, filed May 12, 2005, which claims the benefit of U.S. Provisional Application 60/571,235, filed May 14, 2004.

This application is a continuation-in-part application of U.S. patent application Ser. No. 10/908,461, filed May 12, 2005 now U.S. Pat. No. 7,641,856, which claims the benefit of U.S. Provisional Application 60/571,235, filed May 14, 2004.

This application is a continuation-in-part of U.S. patent application Ser. No. 11/306,508, filed Dec. 30, 2005, which is a continuation-in-part of U.S. patent application Ser. No. 10/950,898, filed Sep. 27, 2004 now U.S. Pat. No. 7,130,046.

This application is a continuation-in-part of U.S. patent application Ser. No. 10/938,265, filed Sep. 9, 2004 now U.S. Pat. No. 7,630,063.

This patent application is a continuation-in-part of U.S. patent application Ser. No. 11/306,508, filed Dec. 30, 2005, which is a continuation-in-part of U.S. patent application Ser. No. 10/908,460, filed May 12, 2005, which claims the benefit of Provisional Patent Application No. 60/571,235, filed May 14, 2004.

Also, this patent application is a continuation-in-part of U.S. patent application Ser. No. 11/306,508, filed Dec. 30, 2005, which is a continuation-in-part of U.S. patent application Ser. No. 10/908,014, filed Apr. 25, 2005, which is a continuation-in-part of U.S. patent application Ser. No. 10/304,773, filed Nov. 26, 2002, which is a continuation-in-part of U.S. patent application Ser. No. 09/630,924, filed Aug. 2, 2000, now U.S. Pat. No. 6,597,438.

Also, this patent application is a continuation-in-part of U.S. patent application Ser. No. 11/306,508, filed Dec. 30, 2005, which is a continuation-in-part of U.S. patent application Ser. No. 10/908,014, filed Apr. 25, 2005, which is a continuation-in-part of U.S. patent application Ser. No. 10/980,685, filed Nov. 3, 2004, which is a division of U.S. patent application Ser. No. 10/174,851, filed Jun. 19, 2002, now U.S. Pat. No. 6,837,476.

Also, this patent application is a continuation-in-part of U.S. patent application Ser. No. 11/306,508, filed Dec. 30, 2005, which is a continuation-in-part of U.S. patent application Ser. No. 10/908,014, filed Apr. 25, 2005, which is a continuation-in-part of U.S. patent application Ser. No. 10/340,231, filed Jan. 10, 2003, now U.S. Pat. No. 6,889,567, which is a division of U.S. patent application Ser. No. 09/586,093, filed Jun. 2, 2000, now U.S. Pat. No. 6,568,286.

Also, this patent application is a continuation-in-part of U.S. patent application Ser. No. 11/306,508, filed Dec. 30, 2005, which is a continuation-in-part of U.S. patent application Ser. No. 10/950,898, filed Sep. 27, 2004.

Also, this patent application is a continuation-in-part of U.S. patent application Ser. No. 11/306,508, filed Dec. 30, 2005, which is a continuation-in-part of U.S. patent application Ser. No. 10/938,265, filed on Sep. 9, 2004, which is a continuation-in-part of U.S. patent application Ser. No. 10/304,773, filed Nov. 26, 2002, which is a continuation-in-part of U.S. application Ser. No. 09/630,924, filed Aug. 2, 2000.

Also, this patent application is a continuation-in-part of U.S. patent application Ser. No. 11/306,508, filed Dec. 30, 2005, which is a continuation-in-part of U.S. patent application Ser. No. 10/938,265, filed on Sep. 9, 2004, which is a continuation-in-part of U.S. patent application Ser. No. 10/225,325, filed Aug. 21, 2002, now U.S. Pat. No. 6,970,245.

Also, this patent application is a continuation-in-part of U.S. patent application Ser. No. 11/306,508, filed Dec. 30, 2005, which is a continuation-in-part of U.S. patent application Ser. No. 10/932,662, filed Sep. 2, 2004.

Also, this patent application is a continuation-in-part of U.S. patent application Ser. No. 11/306,508, filed Dec. 30, 2005, which is a continuation-in-part of U.S. patent application Ser. No. 10/899,607, filed Jul. 15, 2004.

Also, this patent application is a continuation-in-part of U.S. patent application Ser. No. 11/306,508, filed Dec. 30, 2005, which is a continuation-in-part of U.S. patent application Ser. No. 10/938,245, filed on Sep. 9, 2004, which is continuation of U.S. patent application Ser. No. 10/824,859, filed Apr. 14, 2004, which is a continuation-in-part of U.S. patent application Ser. No. 10/225,325, filed Aug. 21, 2002, now U.S. Pat. No. 6,970,245, which is a continuation-in-part of U.S. patent application Ser. No. 09/630,927, filed Aug. 2, 2000, now U.S. Pat. No. 6,549,275.

Also, this patent application is a continuation-in-part of U.S. patent application Ser. No. 11/306,508, filed Dec. 30, 2005, which is a continuation-in-part of U.S. patent application Ser. No. 10/759,875, filed Jan. 16, 2004, which is a continuation-in-part of U.S. patent application Ser. No. 09/896,230, filed Jun. 29, 2001, now U.S. Pat. No. 6,700,130.

Also, this patent application is a continuation-in-part of U.S. patent application Ser. No. 11/306,508, filed Dec. 30, 2005, which is a continuation-in-part of U.S. patent application Ser. No. 10/759,875, filed Jan. 16, 2004, which is a continuation-in-part of U.S. patent application Ser. No. 10/304,773, filed Nov. 26, 2002.

Also, this patent application is a continuation-in-part of U.S. patent application Ser. No. 11/306,508, filed Dec. 30, 2005, which is a continuation-in-part of U.S. patent application Ser. No. 10/304,773, filed Nov. 26, 2002, which is a continuation-in-part of U.S. patent application Ser. No. 09/630,924, filed Aug. 2, 2000, now U.S. Pat. No. 6,597,438.

Also, this patent application is a continuation-in-part of U.S. patent application Ser. No. 11/306,508, filed Dec. 30, 2005, which is a continuation-in-part of U.S. patent application Ser. No. 10/908,014, filed Apr. 25, 2005, which is a continuation-in-part of U.S. patent application Ser. No. 10/953,197, filed Sep. 28, 2004.

Also, this patent application is a continuation-in-part of U.S. patent application Ser. No. 11/306,508, filed Dec. 30, 2005, which is a continuation-in-part of U.S. patent application Ser. No. 11/027,134, filed Dec. 30, 2004, which is a continuation-in-part U.S. patent application Ser. No. 10/304,773, filed Nov. 26, 2002, which is a continuation-in-part of U.S. patent application Ser. No. 09/630,924, filed Aug. 2, 2000, now U.S. Pat. No. 6,597,438.

Also, this patent application is a continuation-in-part of U.S. patent application Ser. No. 11/306,508, filed Dec. 30, 2005, which is a continuation-in-part of U.S. patent application Ser. No. 11/306,402, filed Dec. 27, 2005.

BACKGROUND

The present invention generally relates to sample analyzers, and more particular, to sample analyzers that are simple to operate and have a reduced risk of providing an erroneous result.

Chemical and/or biological analysis is important for life sciences research, clinical diagnostics and a wide range of environmental and process monitoring. In some cases, sample analyzers are used to perform and/or assist in performing chemical and/or biological analysis of a sample fluid. The sample fluid may be a liquid or a gas, depending on the application.

Many sample analyzers are rather large devices that are used in a laboratory environment by trained personnel. To use many sample analyzers, a collected sample must first be processed, such as by diluting the sample to a desired level, adding appropriate reagents, centrifuging the sample to provide a desired separation, and so on, prior to providing the prepared sample to the sample analyzer. To achieve an accurate result, such sample processing must typically be performed by trained personnel, which can increase the cost and time required to perform the sample analysis.

Many sample analyzers also require operator intervention during the analysis phase, such as requiring additional information input or additional processing of the sample. This can further increase the cost and time required to perform a desired sample analysis. Also, many sample analyzers merely provide raw analysis data as an output, and further calculations and/or interpretation must often be performed by trained personnel to make an appropriate clinical or other decision.

U.S. Provisional Patent Application 60/753,293 filed Dec. 22, 2005, is hereby incorporated by reference. U.S. Provisional Patent Application 60/755,014 filed Dec. 29, 2005, is hereby incorporated by reference. U.S. patent application Ser. No. 10/908,460, filed May 12, 2005, is hereby incorporated by reference. U.S. patent application Ser. No. 10/908,461, filed May 12, 2005, is hereby incorporated by reference. U.S. patent application Ser. No. 11/306,508, filed Dec. 30, 2005, is hereby incorporated by reference. a continuation-in-part of U.S. patent application Ser. No. 10/950,898, filed Sep. 27, 2004, is hereby incorporated by reference. U.S. patent application Ser. No. 10/938,265, filed Sep. 9, 2004, is hereby incorporated by reference.

SUMMARY

The present invention generally relates to sample analyzers, and more particular, to sample analyzers that are simple to operate and have a reduced risk of providing an erroneous result to a user. In some cases, the sample analyzer may be a portable sample analyzer that includes a disposable fluidic cartridge.

BRIEF DESCRIPTION OF THE DRAWING

FIG. 9g shows a table shows the diameters suggested for the cavities for the pusher fluid, lysing solution, sphering solution and sheath fluid;

DESCRIPTION

The present invention relates to sample analyzers, and more particular, to sample analyzers that are simple to operate and have a reduced risk of providing an erroneous result. In some examples, the sample analyzer may be, for example, a blood analyzer such as a flow cytometer, a hematology analyzer, a clinical chemistry analyzer (e.g., glucose analyzer, ion analyzer, electrolytes analyzer, dissolved gasses analyzer, and so forth), a urine analyzer or any other suitable analyzer, as desired.

The present invention is such that it or tests performed with it may be waived from regulatory oversight if they meet certain requirements. The present invention may be implemented for, provide, and/or perform tests which can be laboratory examinations and procedures that are simple and accurate so as to render a likelihood of erroneous results negligible, or to pose no reasonable risk of harm to the patient if the test is performed incorrectly. One kind of waivers may be from the Clinical Laboratory Improvement Amendments of 1988 (CLIA).

Figure 1:
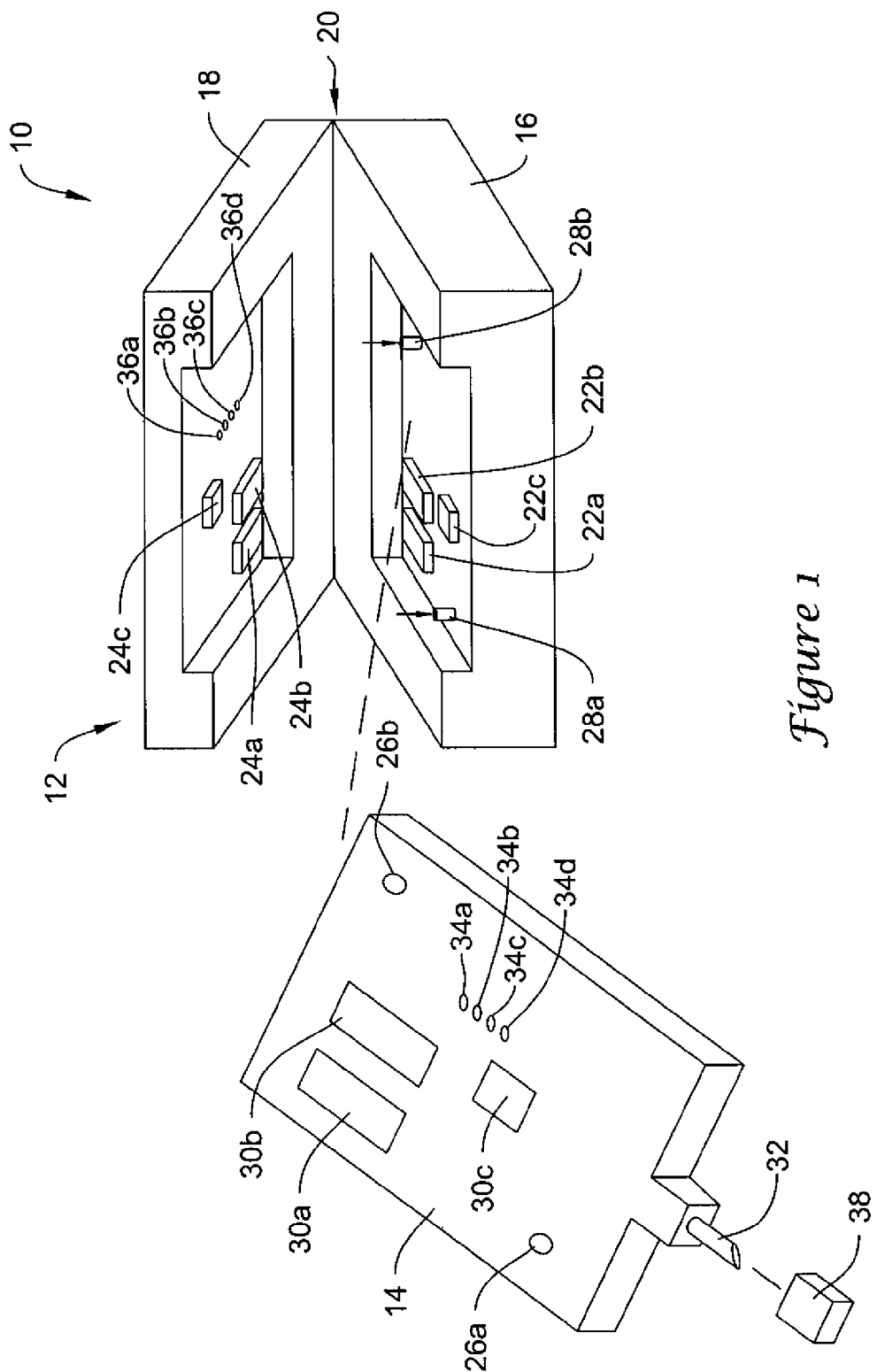
FIG. 1 is a perspective view of an illustrative sample analyzer and cartridge.

FIG. 1 is a perspective view of a flow cytometer. A flow cytometer analyzer is described for illustrative purposes only, and it is contemplated that it may be applied to other types of sample analyzers, as desired. The illustrative sample analyzer is generally shown at 10, and includes a housing 12 and a removable or disposable cartridge 14. The illustrative housing 12 includes a base 16, a cover 18, and a hinge 20 that attaches the base 16 to the cover 18, but this is not required. In the illustrative example, the base 16 includes a first light source 22a, a second light source 22b, and a third light source 22c, along with associated optics and the necessary electronics for operation of the sample analyzer. Each of the light sources may be a single light source or multiple light sources, depending on the application. In some cases, the overall dimensions of the housing may be less than 1 cubic foot, less than one-half cubic foot, less than one-quarter cubic foot, or smaller, as desired. Likewise, the overall weight of the housing may be less than 10 pounds, less than 5 pounds, less than one pound, or less, as desired.

The illustrative cover 12 includes a pressure source (e.g., pressure-chambers with control microvalves), a first light detector 24a, a second light detector 22b, and a third light detector 22c, each with associated optics and electronics. Each of the light detectors may also be a single light detector or multiple light detectors, depending on the application. Polarizers and/or filters may also be provided, if desired, depending on the application.

The illustrative removable cartridge 14 is adapted to receive a sample fluid via a sample collector port, which in the illustrative example, includes a lancet 32. The lancet 32 may be retractable and/or spring loaded, in some examples. A cap 38 may be used to protect the sample collector port and/or lancet 32 when the removable cartridge 14 is not in use.

In the illustrative example, the removable cartridge 14 performs a blood analysis on a whole blood sample. The lancet 32 may be used to prick the finger of the user to produce a sample of blood, which through capillary action, may be drawn into an anti-coagulant coated capillary in the removable cartridge 14. The removable cartridge 14 may be constructed with fluidic circuits, some of which are fabricated using a laminated structure with etched channels. However, it is contemplated that the removable cartridge 14 may be constructed in any suitable manner including by injection molding or any other suitable manufacturing process or approach, as desired.

During use, and after a blood sample has been drawn into the removable cartridge 14, the removable cartridge 14 may be inserted into the housing. In some cases, the removable cartridge 14 may be inserted into the housing when the cover 18 is in the open position. However, in other examples, the removable cartridge 14 may be inserted into the housing in any suitable way. For example, the housing may have a slot, and the removable cartridge 14 may be inserted into the slot of the housing.

Returning to the illustrative example of FIG. 1, the removable cartridge 14 may include holes 26a and 26b for receiving registration pins 28a and 28b in the base 16, which may help provide alignment and coupling between the different parts of the instrument. The removable cartridge 14 may also include a first transparent flow stream window 30a, a second transparent flow stream window 30b and a third transparent window 30c, which are in alignment with the first, second and third light sources 22a, 22b and 22c, and the first, second and third light detectors 24a, 24b and 24c, respectively.

When the cover is moved to the closed position, and the system is pressurized, the cover 18 may provide controlled pressures via pressure providing ports 36a, 36b, 36c, and 36d to pressure receiving ports 34a, 34b, 34c and 34c, respectively, in the illustrative removable cartridge 14. It is contemplated that more or less pressure providing and pressure receiving ports may be used, depending on the application. Alternatively, or in addition, it is contemplated that one or more micro-pumps, such as electrostatically actuated meso pumps, may be provided on or in the removable cartridge 14 to provide the necessary pressures to operate the fluidic circuit on the removable cartridge 14. Some illustrative electrostatically actuated meso pumps are described in, for example, U.S. Pat. Nos. 5,836,750, 6,106,245, 6,179,586, 6,729,856, and 6,767,190, all assigned to the assignee of the present invention, and all hereby incorporated by reference.

Once pressurized, the illustrative instrument may perform a blood analysis on the collected blood sample. In some cases, the blood analysis may include a complete blood count (CBC) analysis, but other types of analysis can be performed, depending on the application.

To count and classify red blood cells, a portion of the whole blood sample may be partitioned and provided to a red blood measurement channel in the removable cartridge 14. The blood sample may then be diluted if desired, the red blood cells may be sphered on the fly, the resulting sample may be hydrodynamically focused for core formation and ultimately provided to a first cytometry channel. The first cytometry channel may be located along the first transparent flow stream window 30a of the removable cartridge 14 so that the cells in the flow stream can be optically interrogated by the first light source 22a and the first light detector 24a. In some cases, a first flow sensor may be provided on the removable cartridge 14 to provide a measure of the flow rate through the first cytometry channel.

In some cases, the measured parameters may include, for example, sample flow rate (FR), measurement time (T) duration, sample dilution factor (DF), number of red blood cells counted ($N_{RB}$), number of platelets counted (Npt), the diameter of each cell (drbc) and hemoglobin concentration of each cell (CHC). From these parameters, a number of red blood cell analysis parameters may be calculated including, for example, a red blood cell count (RBC=$N_{RB}$/(DF×FR×T)), a platelet count (Plt=$N_{Plt}$/(DF×FR×T)), a mean cell hemoglobin concentration (MCHC=<CHC>), a mean cell volume (MCV=$(\pi/6)$×<drbc$^3$>), a mean cell hemoglobin content (MCH=$(\pi/6)$×<drbc$^3$×CHC>), a relative distribution width (RDW=Standard Deviation of [$(\pi/6)$×drbc$^3$]/MCV), a Hematocrit parameter (Hct=RBC×MCV) and/or a hemoglobin concentration (Hb=MCHC×Hct).

In some examples, some of the blood sample is also directed to an absorption measurement channel. The absorption measurement channel may be located along the third transparent window 30c of the removable cartridge 14 so that the blood sample can be optically interrogated by the third light source 22c and the third light detector 24c. A flow sensor may be provided on the removable cartridge 14 to provide a measure of the flow rate into or through the absorption measurement channel. The absorption measurement channel may provide a measure of the absorption of the incident light provided by the third light source 22c. The measured absorption level may provide an indication of the bulk or mean cell hemoglobin concentration in the blood sample.

To count and classify white blood cells, a portion of the whole blood sample may be partitioned and provided to a white blood measurement channel in the removable cartridge 14. The blood sample may then be diluted if desired, the red blood cells may be lysed on the fly, the resulting sample may be hydrodynamically focused for core formation and ultimately provided to a second cytometry channel. The second cytometry channel may be located along the second transparent flow stream window 30b of the removable cartridge 14 so that the cells in the flow stream can be optically interrogated by the second light source 22b and the second light detector 24b. A flow sensor may be provided on the removable cartridge 14 to provide a measure of the flow rate through the second cytometry channel. In some cases, measured white blood cell parameters may include, for example, three (3) or (5) part white cell differentiation, total white blood cell count and/or on-axis white blood cell volume. Other parameters may also be measured or calculated, depending on the application.

FIG. 1 shows one illustrative sample analyzer and cartridge assembly. However, it is contemplated that other sample analyzer configurations may be used. For example, the sample analyzer 10 and removable cartridge may be similar to that described in U.S. Patent Application 2004/0211077 to Schwichtenberg et al., which is hereby incorporated by reference.

In some cases, the sample analyzer 10 is adapted to be used at the point of care of a patient such as in a doctor's office, in the home, or elsewhere in the field. The ability to provide a sample analyzer 10 that can be reliably used outside of the laboratory environment, with little or no specialized training, may help streamline the sample analysis process, reduce the cost and burden on medical personnel, and increase the convenience of sample analysis for many patients, including those that require relatively frequent blood monitoring/analysis.

During operation, the sample analyzer 10 may receive a collected sample, such as a collected whole blood sample, and once the analyzer is activated, the sample analyzer 10 may automatically process the sample and provide information to the user to make a clinical decision. In some examples, the sample analyzer 10 may display or print out quantitative results (e.g., inside and/or outside of a predefined range), such that no further calculations or interpretation is required by the user.

Figure 2:
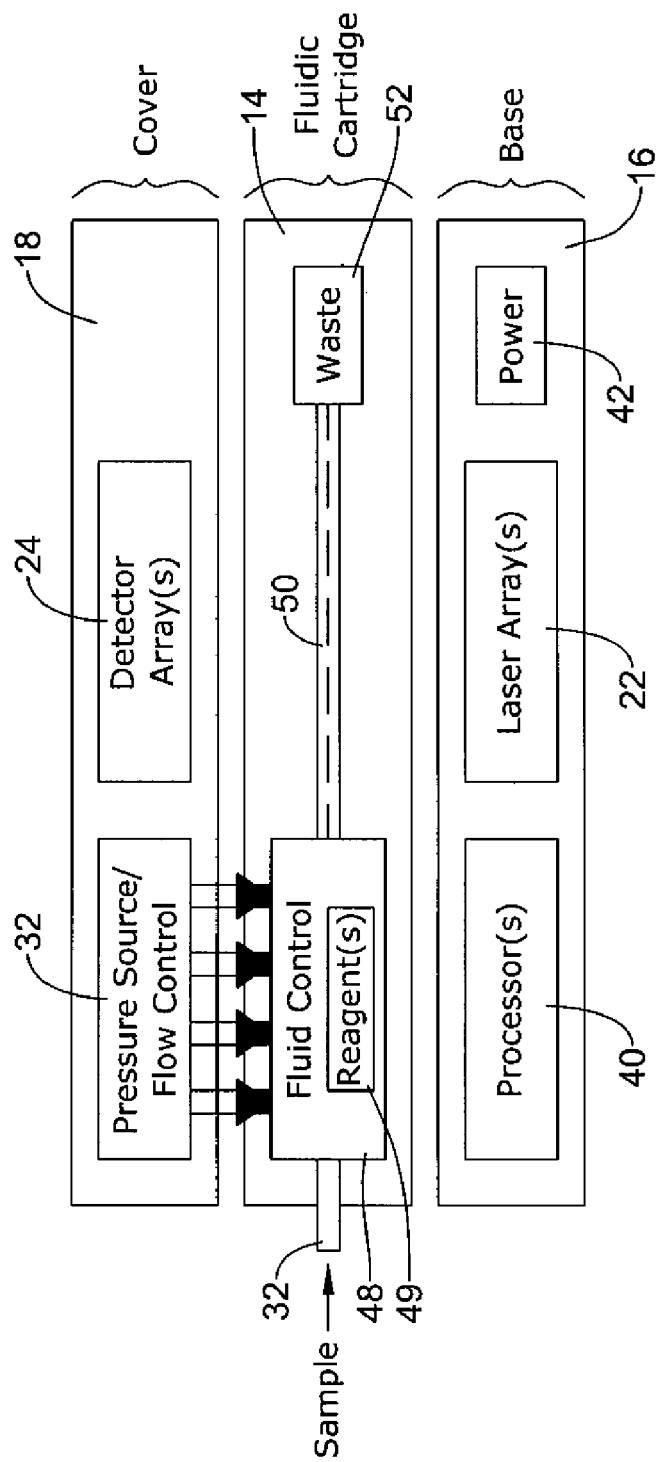
FIG. 2 is a schematic view of the illustrative sample analyzer and cartridge of FIG. 1.

FIG. 2 is a schematic view of the illustrative sample analyzer and cartridge of FIG. 1. As detailed above, and in the illustrative example, the base 16 may include a number of light sources 22, associated optics and the necessary control and processing electronics 40 for operation of the analyzer. The base 16 may also include a battery 42, transformer or other power source. The cover 12 is shown having a pressure source/flow control block 44 and a number of light detectors 24 with associated optics.

The removable cartridge 14 may receive a sample fluid via the sample collector port or lancet 32. When pressurized by the pressure source/flow control block 44, the removable cartridge 14 may perform a blood analysis on the received blood sample. In some examples, and as described above, the removable cartridge 14 may include a number or reagents 49, and a fluidic circuit for mixing the reagents with the blood sample to prepare the blood sample for analysis. Also, the removable cartridge 14 may, in some cases, include a number of flow sensors to help control and/or verify the proper operation of the fluidic circuit.

In some cases, the blood sample is prepared (e.g., lysed, sphered, stained, diluted and/or otherwise processed) and then hydrodynamically focused for core formation in one or more on-board cytometry channels, such as cytometry channel 50. In the illustrative example, the cytometry channel 50 is routed past a transparent flow stream window such as the first transparent flow stream window 30a in the removable cartridge 14. An array of light sources 22 and associated optics in the base 16 may provide light through the core stream via the flow stream window 30a. An array of light detectors 24 and associated optics may receive scattered and non-scattered light from the core, also via the flow stream window 30a. The controller or processor 40 may receive output signals from the array of detectors 24, and may differentiate and/or counts selected cells that are present in the core stream.

It is contemplated that the removable cartridge 14 may include a fluid control block 48 for helping to control the velocity of at least some of the fluids on the removable cartridge 14. In the illustrative example, the fluid control block 48 may include flow sensors for sensing the velocity of the various fluids and report the velocities to the controller or processor 40. The controller or processor 40 may then adjust one or more control signals, which are provided to the pressure source/flow control block 44, to achieve the desired pressures and thus the desired fluid velocities for proper operation of the analyzer.

Because blood and other biological waste can spread disease, the removable cartridge 14 may include a waste reservoir 52 downstream of the illustrative cytometry channel 50. The waste reservoir 52 may receive and store the fluid of the flow stream in the removable cartridge 14. When a test is completed, the removable cartridge 14 may be removed from the analyzer and disposed of, for instance, in a container compatible with biological waste.

Figure 3:
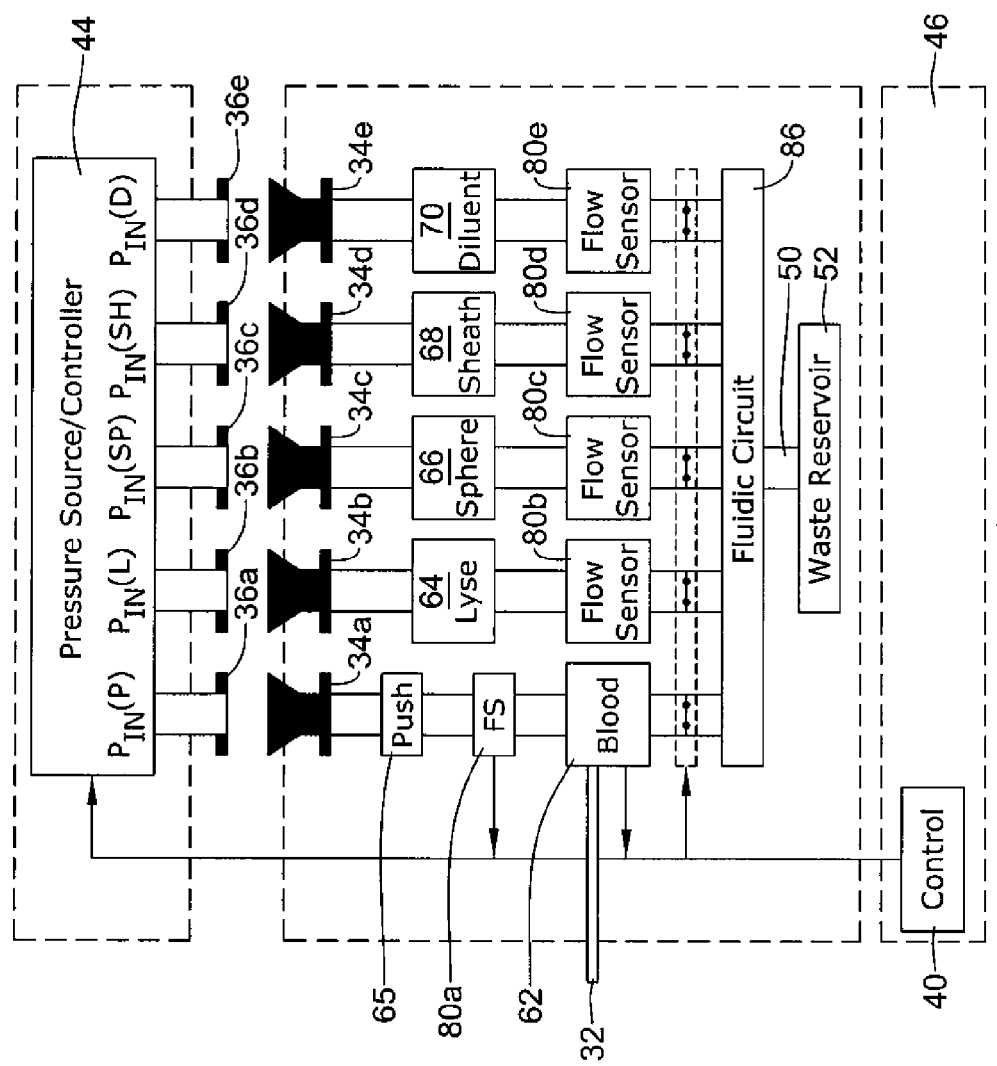
FIG. 3 is a more detailed schematic diagram showing the flow control of the sample analyzer and cartridge of FIG. 2.

FIG. 3 is a more detailed schematic diagram showing the flow control of the sample analyzer and cartridge of FIG. 2. In the illustrative example, the pressure source/flow controller 44 in the cover 18 provides five controlled pressures including a sample push (P) pressure 36a, a lyse (L) pressure 36b, a sphere (SP) pressure 36c, a sheath (SH) pressure 36d, and a diluent (D) pressure 36e. These are only illustrative, and it is contemplated that more, less or different pressures (e.g., stain pressure to a stain reservoir) may be provided by pressure source/flow controller 44, depending on the application. Also, it is contemplated that the cover 18 may not include a pressure source/flow controller 44 at all. Instead, the removable cartridge 14 may include an on-board pressure source, such as a compressed air reservoir, one or more micro-pumps such as electrostatically actuated meso pumps as described above, or any other suitable pressure source, as desired. The array of light sources and detectors are not shown in FIG. 3.

In the illustrative example, pressure source 36a provides pressure to a blood sample reservoir 62 via a pusher fluid 65, pressure source 36b provides pressure to a lyse reservoir 64, pressure source 36c provides pressure to a sphere reservoir 66, pressure source 36d provides pressure to a sheath reservoir 68, and pressure source 36e provides pressure to a diluent reservoir 70.

In one illustrative example, each pressure source may include a first pressure chamber for receiving an input pressure, and a second pressure chamber for providing a controlled pressure to the removable cartridge. A first valve may be provided between the first pressure chamber and the second pressure chamber for controllably releasing the pressure in the first pressure chamber to the second pressure chamber. A second valve, in fluid communication with the second pressure chamber, may controllably vent the pressure in the second pressure chamber to atmosphere. This may allow the pressure source/flow controller 44 to provide a controlled pressure to each of the pressure receiving ports on the removable cartridge 14. Each valve may be an array of electrostatically actuated microvalves that are individually addressable and controllable, as described in, for example, U.S. Pat. No. 6,240,944, which is hereby incorporated by reference. Alternatively, each valve may be an array of electrostatically actuated microvalves that are pulse modulated with a controllable duty cycle to achieve a controlled "effective" flow or leak rate. Other valves may also be used, if desired.

The illustrative removable cartridge 14 includes five pressure receiving ports 34a, 34b, 34c, 34d and 34e, each for receiving a corresponding controlled pressure from the pressure source/flow controller 44. In the illustrative example, the pressure receiving ports 34a, 34b, 34c, 34d and 34e direct the controlled pressures to the blood reservoir 62, the lyse reservoir 64, the sphere reservoir 66, the sheath reservoir 68, and the diluent reservoir 70, respectively. The lyse reservoir 64, sphere reservoir 66, sheath reservoir 68 and diluent reservoir 70 may be filled before the removable cartridge 14 is shipped for use, while the blood reservoir 62 may be filled in the field via sample collector port or lancet 32.

As shown, a flow sensor may be provided in-line with each or selected fluids. Each flow sensor 80a-80e may measure the velocity of the corresponding fluid. The flow sensors 80a-80e may be thermal anemometer type flow sensors, and microbridge type flow sensors. Microbridge flow sensors are described in, for example, U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 5,050,429, all of which are hereby incorporated by reference.

Alternatively, or in addition, the sensors 80a-80e may be used to detect one or more characteristics of the fluid, such as thermal conductivity, specific heat, fluid density, electrical resistivity, and/or other characteristics of the fluid to, for example, help identify or verify that the fluid passing through the flow channel is the expected fluid or expected fluid type. This may help verify that the expected fluid is actually being used in the flow channel during a particular analysis or procedure. A controller may be programmed to detect whether the expected fluid is actually being used in the flow channel, and in some cases, issue a warning and/or shut down the sample analyzer.

An output signal from each flow sensor 80a-80e may be provided to controller or processor 40. The controller or processor 40 may provide control signals to the pressure source/controller 44, as shown. For example, to control the pressure provided to the blood sample, the controller or processor 40 may open a first valve between a first pressure chamber and a second pressure chamber in the pressure source/controller 44 for controllably releasing a pressure in the first pressure chamber to the second pressure chamber when the velocity of the blood sample drops below a first predetermined value. Likewise, the controller or processor 40 may open a second valve that vent the pressure in the second pressure chamber when the velocity of the blood sample increases above a second predetermined value. The controller or processor 40 may control the velocities of the lysing reagent, sphering reagent, sheath fluid and diluent in a similar manner.

In some cases, the controller or processor 40 may detect one or more changes in the flow rate passing through a flow channel. A change in flow rate may correspond to, for example, one or more bubbles in a flow channel, an occlusion or partial occlusion of a flow channel caused by, for example, coagulation of the blood sample, unwanted or foreign objects in a flow channel, and/or other undesirable characteristics of a flow channel. In some cases, a rise time, fall time or some other characteristic of the flow rate may be used. The controller or processor 40 may be programmed to detect such characteristics from the flow rate, and in some cases, issue a warning and/or shut down the sample analyzer.

Thermal anemometer type flow sensors typically include a heater element that, when energized, produces one or more heat pulses in the fluid, and further includes one or more heat sensors positioned upstream and/or downstream of the heater element to detect the one or more heat pulses. The velocity of the fluid through the flow channel may be related to the time that it takes for a heat pulse to travel from the heater element to one of the spaced heat sensors.

In some cases, thermal anemometer type flow sensors may be used to detect the thermal conductivity and/or specific heat of the fluid. Changes in the thermal conductivity and/or specific heat of the fluid may correspond to changes in the fluid characteristics, such as a change of state of the fluid (coagulation of a blood sample), bubbles in the fluid, unwanted or foreign objects in the fluid, and so on. Alternatively, or in addition, thermal anemometer type flow sensors may be used to detect one or more characteristics of the fluid such as thermal conductivity, specific heat, and so forth, to, for example, help identify or verify that the fluid passing through the flow channel is the expected fluid or expected fluid type. This may help verify that the expected fluid is actually being used in the flow channel during a particular analysis or procedure. In some examples, it is contemplated that the controller or processor 40 may detect characteristics of the fluid by monitoring the thermal conductivity and/or specific heat of the fluid that passes by the thermal anemometer type flow sensors. The controller or processor 40 may be programmed to detect, for example, undesirable characteristics in the fluid (e.g., bubbles), and/or whether the expected fluid is actually being used in the flow channel, and in some cases, issue a warning and/or shut down the sample analyzer.

In some cases, an impedance sensor may be provided in fluid communication with a flow channel. The controller or processor 40 may be coupled to the impedance sensor. Changes in the impedance of the fluid may indicate a change in fluid characteristics, such as a change in the state of the fluid (coagulation of a blood sample), bubbles in the fluid, unwanted or foreign objects in the fluid, the correct fluid type, and so on. Thus, and in some examples, it is contemplated that the controller or processor 40 may detect characteristics of the fluid by monitoring the impedance of the fluid that passes by the impedance sensor.

Downstream valves generally shown at 110 may also be provided. Controller or processor 40 may open/close downstream valves 110, as desired. For example, the downstream valves 110 may remain closed until the system is fully pressurized. This may help prevent the blood, lysing reagent, sphering reagent, sheath fluid and diluent from flowing into the fluidic circuit 86 before the system is fully pressurized. Also, the downstream valves 110 may be controlled to aid in performing certain tests, like zero-flow tests, and so forth. In another example, downstream valves 110 may be opened by mechanical action when, for example, the cover is closed.

Figure 4:
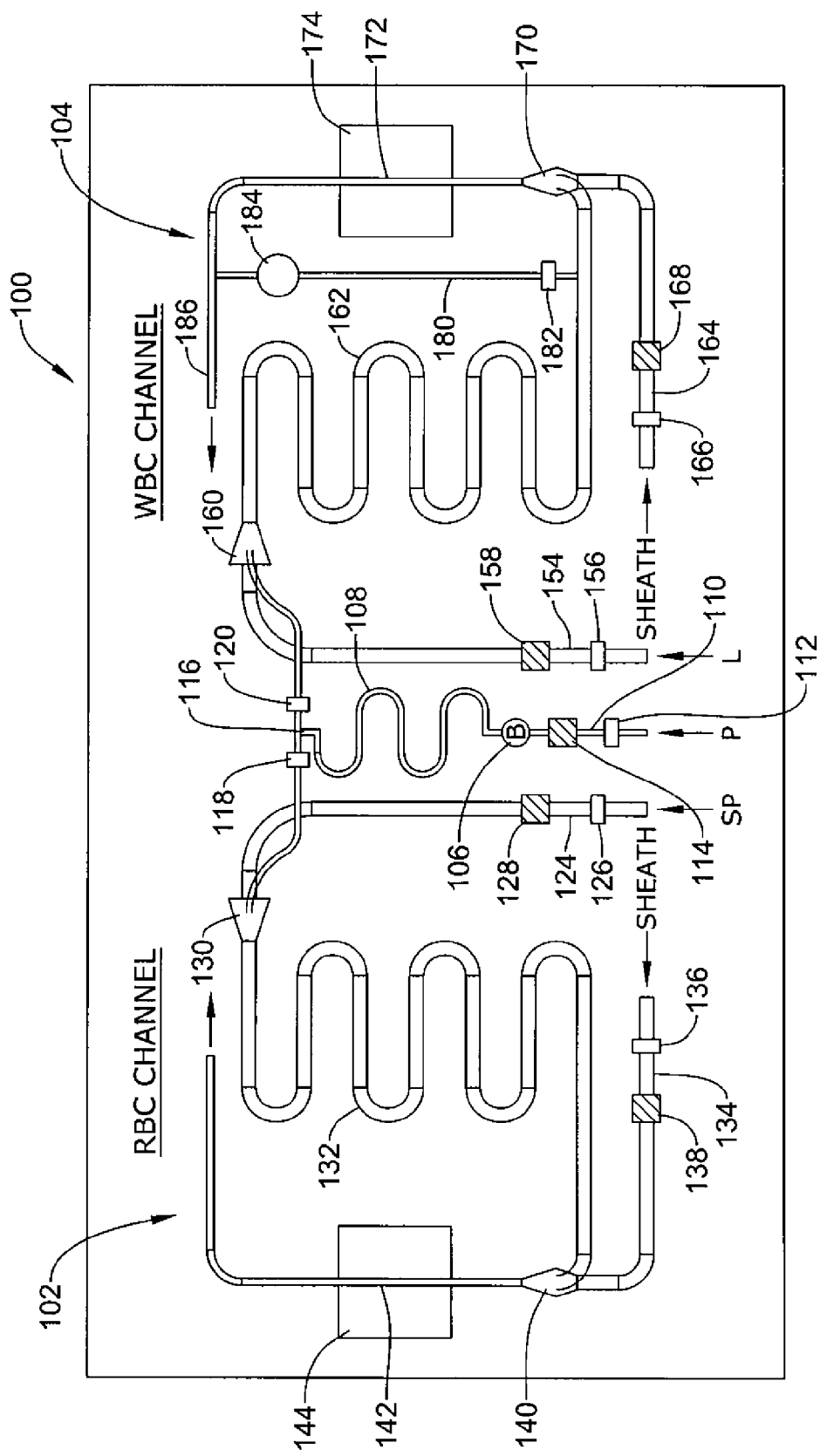
FIG. 4 is a schematic view of certain features of an illustrative cartridge.

FIG. 4 is a schematic view of certain features of an illustrative removable cartridge. The illustrative removable cartridge is generally shown at 100, and may be similar to removable cartridge 14 shown and described above with reference to FIGS. 1-3. It should be understood that the removable cartridge 100 is only illustrative, and that the present example can be applied to many microfluidic cartridges, regardless of form, function or configuration. For example, the present example may be applied to removable cartridges adapted for flow cytometry, hematology, clinical chemistry, blood chemistry analysis, urinalysis, blood gas analysis, virus analysis, bacteria analysis, electrolyte measurements, and so on. It is also contemplated that the removable cartridges of the present system, such as removable cartridge 100, may be made from any suitable material or material system including, for example, glass, silicon, one or more polymers, or any other suitable material or material system, or combination of materials or material systems.

The illustrative removable cartridge 100 includes a first measurement channel 102 and a second measurement channel 104, although more or less measurement channels may be used, as desired. The first measurement channel 102, in the illustrative example, is a red blood cell measurement channel, and the second measurement channel 104 is a white blood cell measurement channel. A whole blood sample is received by the removable cartridge 100 via blood receiving port 106, which through capillary action, draws in a known amount of blood into an anti-coagulant coated blood sample storage capillary 108. A sample push (P) pressure, such as a sample push (P) pressure 36a of FIG. 3, is provided to a sample push fluid reservoir, such as sample push fluid reservoir 65 of FIG. 3. When pressure is applied, the sample push fluid is forced from the sample push fluid reservoir into a blood sample push channel 110.

In some illustrative examples, a valve 112 and a flow sensor 114 may be provided in line with the blood sample push channel 110. The valve 112 may be controlled to open when it is desirable to push the blood sample through the fluidic circuit. The flow sensor 114 may measure the flow rate of the blood sample push fluid, and thus the blood sample flow rate through the anti-coagulant coated capillary 108. The flow rate provided by the flow sensor 114 may be used to help control the sample push (P) pressure that is provided to the removable cartridge 100.

In the illustrative example, the whole blood sample is partitioned and provided to the red blood cell measurement channel 102 and the white blood cell measurement channel 104 via branch 116. In the illustrative example, a valve 118 is provided in line with the branch to control the blood sample flow into the red blood cell measurement channel 102, and a valve 120 is provided to control the blood sample flow into the white blood cell measurement channel 104.

Turning specifically to the red blood cell measurement channel 102, a red blood cell sphering reagent pressure (SP), such as a sphering pressure (SP) 36c of FIG. 3, is provided to a sphering reagent reservoir, such as sphering reservoir 66 of FIG. 3. When pressure is applied, the sphering reagent in the sphering reservoir 66 is forced into a sphering reagent channel 124.

In some illustrative examples, a valve 126 and a flow sensor 128 may also be provided in line with the sphering reagent channel 124. The valve 126 may be controlled to open when it is desirable to push the sphering reagent into the fluidic circuit. The flow sensor 128 may measure the flow rate of the sphering reagent, and provide a measure of the sphering reagent flow rate through the sphering reagent channel 124. The flow rate provided by the flow sensor 128 may be used to help control the sphering pressure (SP) that is provided to the removable cartridge 100 by the pressure source/controller 44.

During normal functional operation of the illustrative removable cartridge 100, the sphering reagent is pushed into an intersecting region 130 at a sphering reagent flow rate, and the blood sample is pushed into the intersecting region 130 at a blood sample flow rate. The blood sample flow rate and the sphering reagent flow rate may be controlled by the pressure source/controller 44 of FIG. 3.

The intersection region 130 may be configured so that the sphering reagent flows circumferentially around the blood sample when both fluids are flowing through the intersection region 130. In some cases, the sphering reagent flow rate may be higher than the blood sample flow rate, which may help improve the flow characteristics in a downstream sphering-on-the-fly channel 132, and in some cases, to help form a thin ribbon of blood that is completely and uniformly surrounded by the sphering reagent. Such a ribbon flow may help the sphering reagent uniformly sphere the red blood cells as they travel through the sphering-on-the-fly channel 132. Furthermore, the length of the sphering-on-the-fly channel 132, in conjunction with the flow rate of the sphering reagent and blood sample, may be set such that the blood sample is exposed to the sphering reagent for an appropriate amount of time.

A sheath fluid (SH) pressure, such as a sheath (SH) pressure 36d of FIG. 3, may be provided to a sheath fluid reservoir, such as sheath fluid reservoir 68 of FIG. 3. When pressure is applied, the sheath fluid is forced from the sheath fluid reservoir 68 into a sheath channel 134. In some illustrative examples, a valve 136 and a flow sensor 138 may be provided in line with a sheath channel 134. The valve 136 may be controlled to open when it is desirable to push the sheath fluid into the fluidic circuit. The flow sensor 138 may measure the flow rate of the sheath fluid, and may provide a measure of the sheath flow rate through the sheath channel 134. The flow rate provided by the flow sensor 138 may be used to help control the sheath pressure (SH) that is provided to the removable cartridge 100.

In the illustrative example, the sheath fluid is provided to an intersecting region 140 at a sheath fluid flow rate, and the sphered blood sample is provided to the intersecting region 140 at a sphered blood sample flow rate. The sphered blood sample flow rate and the sheath flow rate may be controlled by a pressure source/controller, such as pressure source/controller 44 of FIG. 3.

The intersection region 140 may be configured so that the sheath fluid flows circumferentially around the sphered blood sample when both fluids are flowing through the intersection region 140. In some cases, the sheath flow rate is significantly higher than the sphered blood sample flow rate, which may help improve core formation in a downstream flow cytometry channel 142. For example, in some flow cytometry applications, the intersecting region 140 may be configured to hydrodynamically focus and arrange the sphered blood cells in a single file core so that each red blood cell can be individually optically interrogated by an analyzer as they pass through an optical window region 144 in the removable cartridge 100. In some cases, the fluid that passes through the cytometry channel 142 is directed to an on-board waste reservoir.

Turning now to the white blood cell measurement channel 104, a white blood cell lysing reagent pressure (L), such as a lysing pressure (L) 36b of FIG. 3, is provided to a lysing reagent reservoir, such as lyse reservoir 64 of FIG. 3. When pressure is applied, the lysing reagent in the lyse reservoir 64 is forced into a lysing reagent channel 154.

In some illustrative examples, a valve 156 and a flow sensor 158 may be provided in line with the lysing reagent channel 154. The valve 156 may be controlled to open when it is desirable to push the lysing reagent into the fluidic circuit. The flow sensor 158 may measure the flow rate of the lysing reagent, and provide a measure of the lysing reagent flow rate through the lysing reagent channel 154. The flow rate provided by the flow sensor 158 may be used to help control the lysing pressure (L) that is provided to the removable cartridge 100 by the pressure source/controller 44.

During normal functional operation of the illustrative removable cartridge 100, the lysing reagent is provided to an intersecting region 160 at a lysing reagent flow rate, and the blood sample is provided to the intersecting region 160 at a blood sample flow rate. The blood sample flow rate and the lysing reagent flow rate may be controlled by a pressure source/controller, such as pressure source/controller 44 of FIG. 3.

The intersection region 160 may be configured so that the lysing reagent flows circumferentially around the blood sample when both fluids are flowing through the intersection region 160. In some cases, the lysing reagent flow rate may be higher than the blood sample flow rate, which may help improve the flow characteristics in a lysing-on-the-fly channel 162, and in some cases, to help form a thin ribbon of blood that is completely and uniformly surrounded by the lysing reagent. Such a ribbon flow may help the lysing reagent uniformly lyse the red blood cells as they travel through the lysing-on-the-fly channel 162. Furthermore, the length of the lysing-on-the-fly channel 162, in conjunction with the flow rate of the lysing reagent and blood sample, may be set such that the blood sample is exposed to the lysing reagent for an appropriate amount of time.

A sheath fluid (SH) pressure, such as a sheath (SH) pressure 36d of FIG. 3, may be provided to a sheath fluid reservoir, such as sheath fluid reservoir 68 of FIG. 3. When pressure is applied, the sheath fluid is forced from the sheath fluid reservoir 68 into a sheath channel 164. In some illustrative examples, a valve 166 and a flow sensor 168 may be provided in line with a sheath channel 164. The valve 166 may be controlled to open when it is desirable to push the sheath fluid into the fluidic circuit. The flow sensor 168 may measure the flow rate of the sheath fluid, and may provide a measure of the sheath flow rate through the sheath channel 164. The flow rate provided by the flow sensor 168 may be used to help control the sheath pressure (SH) that is provided to the removable cartridge 100. In some cases, the sheath flow rate through sheath channel 164 is the same as the sheath flow rate through sheath channel 134. However, in other cases, the sheath flow rate through sheath channel 164 may be different from the sheath flow rate through sheath channel 134.

In the illustrative example, the sheath fluid is provided to an intersecting region 170 at a sheath fluid flow rate, and the lysed blood sample is provided to the intersecting region 170 at a lysed blood sample flow rate. The lysed blood sample flow rate and the sheath flow rate may be controlled by a pressure source/controller, such as pressure source/controller 44 of FIG. 3.

The intersection region 170 may be configured so that the sheath fluid flows circumferentially around the lysed blood sample when both fluids are flowing through the intersection region 170. In some cases, the sheath flow rate is significantly higher than the lysed blood sample flow rate, which may help improve core formation in a downstream flow cytometry channel 172. For example, in some flow cytometry applications, the intersecting region 170 may be configured to hydrodynamically focus and arrange the white blood cells in the lysed blood sample in a single file core so that each white blood cell can be individually optically interrogated by an analyzer as they pass through an optical window region 174 in the removable cartridge 100. In some cases, the fluid that passes through the cytometry channel 172 is provided to an on-board waste reservoir.

Figure 8:
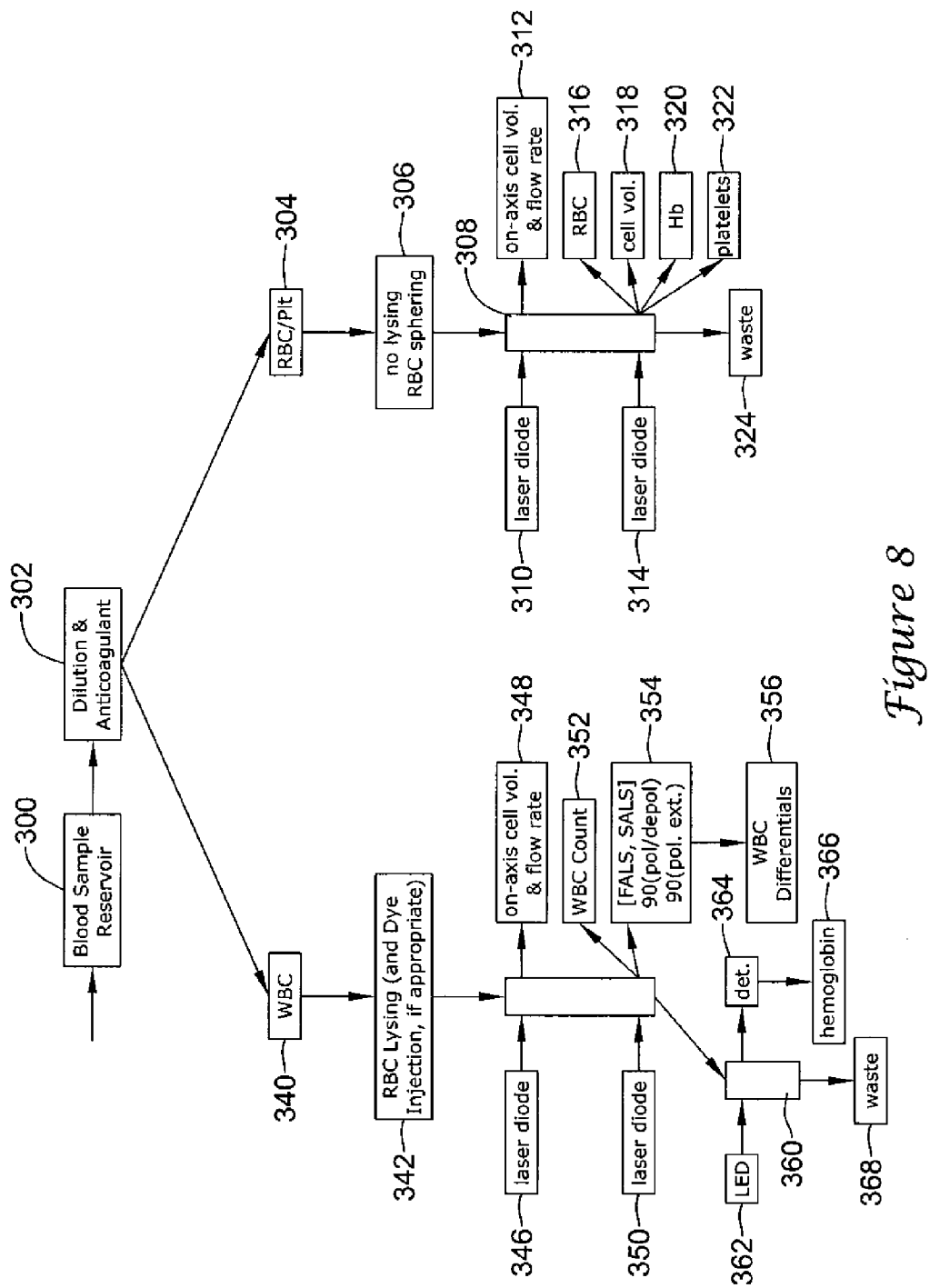
FIG. 8 is a schematic flow diagram showing another illustrative approach for analyzing a blood sample.

In some cases, an absorption measurement channel may also be provided. In the illustrative example, a portion of the lysed blood sample is provided to absorption channel 180. A valve 182 may be provided to selectively allow a portion of the lysed blood sample to pass to the absorption channel or region 184. The analyzer may include a light source to illuminate the absorption channel or region 184, as well as a detector to detect the light that is not absorbed by the lysed blood sample in the absorption channel or region 184. The analyzer may then determine an absorption level, from which a bulk absorption based hemoglobin measurement can be made. In some cases, and as shown in FIG. 8, the absorption channel 184 may be situated downstream of the cytometry channel 172, if desired. In other cases, a whole blood sample may be provided directly, such as from branch 116, to an absorption channel. In such cases, the absorption channel may include a mechanism to lyse the red blood cells prior to taking the absorption measurement. While the illustrative removable cartridge 100 is adapted to perform a Complete Blood Count (CBC) analysis on a whole blood sample, it is contemplated that other removable cartridge configurations and analysis types may be used, as desired.

Figure 5:
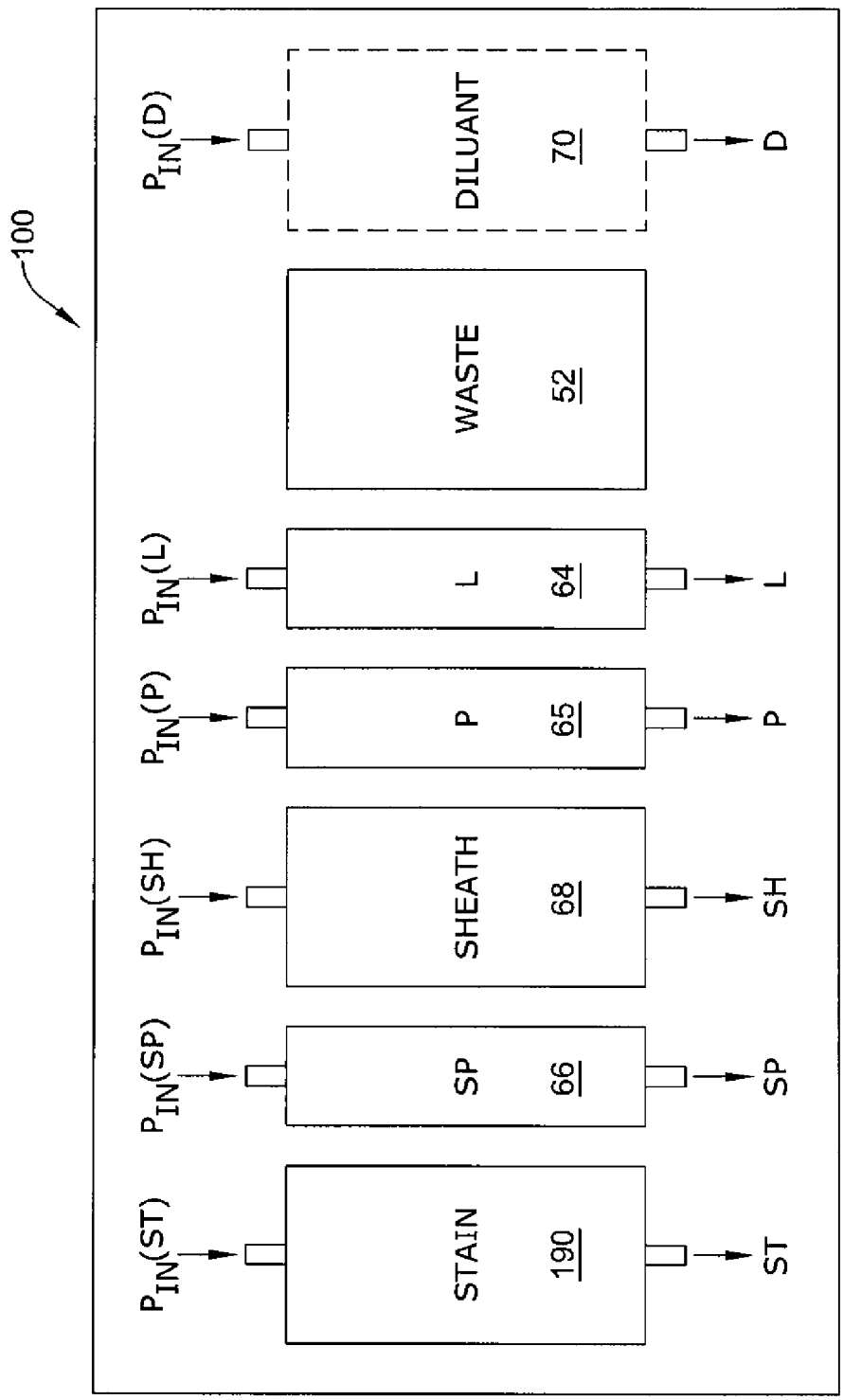
FIG. 5 is a schematic view of a number of illustrative storage reservoirs that can be included in a cartridge.

FIG. 5 is a schematic view of a number of illustrative storage reservoirs that can be included in a removable cartridge. In the illustrative example, a removable cartridge such as removable cartridge 100 of FIG. 4 may include, for example, a lysing reagent reservoir 64, a pusher fluid reservoir 65, a sphering reagent reservoir 66, a sheath fluid reservoir 68, a diluent fluid reservoir 70, a stain reservoir 190 and a waste reservoir 52. These are only illustrative, and it is contemplated that more, less, none or different reservoirs may be provided on or in a removable cartridge.

Each reservoir may be sized and include an appropriate amount of fluid and/or reagent to support the desired operation of the removable cartridge. The diluent reservoir 70 may include a diluent fluid for diluting the incoming sample, such as a whole blood sample. In the illustrative example of FIG. 4, the sphering reagent and/or lysing reagents may perform the function of a diluent, and therefore, a separate diluent reservoir 70 may not be required or even desired. Likewise, and in some examples, a stain reservoir such as stain reservoir 190 may be desirable to add a stain to the white blood cell channel to support white blood cell differentiation. It is contemplated that the reagents and/or fluids stored in the reservoirs may initially be in liquid or lyophilized form, depending on the application.

Figure 6:
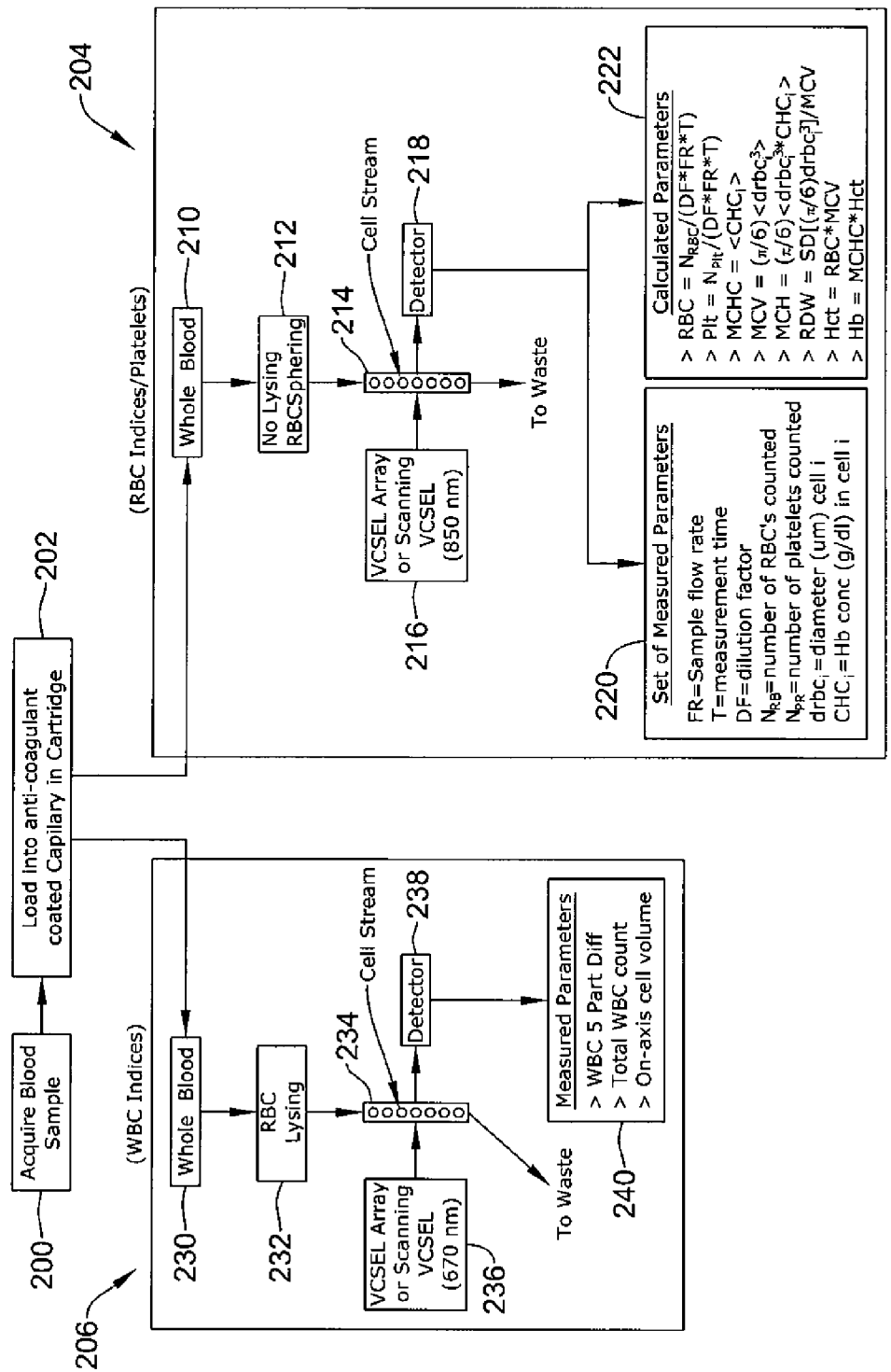
FIG. 6 is a schematic flow diagram showing an illustrative approach for analyzing a blood sample.

FIG. 6 is a schematic flow diagram showing an illustrative approach for analyzing a blood sample using a removable cartridge. In the illustrative approach, a blood sample is first acquired at step 200. Next, the blood sample is provided to an anti-coagulant coated capillary in a removable cartridge. The blood sample is then partitioned and provided to a Red Blood Cell and Platelet (RBC/P) measurement channel 204 and a White Blood Cell (WBC) measurement channel 206.

In the RBC/P measurement channel 204, the red blood cells are first sphered as shown at 212, and then hydrodynamically focused and provided single file down a RBC/P cytometry channel 214 in the removable cartridge. A light source 216, such as a Vertical Cavity Surface Emitting Laser (VCSEL), shines light on the individual cells as they pass by an analysis region of the RBC/P cytometry channel 214. In some cases, an array of VCSEL devices is provided, and only the VCSEL(s) that is/are aligned with the individual cells as they pass by the analysis region of the RBC/P cytometry channel 214 is activated. Some of the incident light provided by the VCSEL is scattered, and a detector 218 detects the scattered light. In some cases, the detector 218 may detect forward angle scatter light (FALS), small angle scatter Light (SALS) and large angle scatter light (LALS).

In some cases, a laser (or other) source is focused into the RBC/P cytometer channel 214, either as an elongated line source or as two separate spot sources. The RBC and platelets in the RBC/P cytometer channel 214 through the focused light. High quality collection optics may be used to form a sharp image of the cells and focused illumination onto an opaque screen containing one, two or more parallel slits whose longitudinal axes are arranged orthogonal to the flow direction in the RBC/P cytometer channel 214. The distance between the slits may be, for example, on the order of the mean cell separation expected in the RBC/P cytometer channel 214. The opaque screen containing the slits may be placed in front of one or more detectors 218. As the image of a cell passes over a slit, it obscures the light incident on the slit and causes a reduction in the signal on the detector 218, producing a pulse waveform whose width is proportional to the cell diameter. When two spaced slits are provided, the two waveforms may permit the calculation of the cell flow velocity, and hence the cell size. High signal-to-noise may be obtained using this technique, which permits easy counting of events and identification of multiple cell events. Pulse width and amplitude may further enable the discrimination of some cell types.

In some cases, an image of both the cell and the light source is imaged on a double slit aperture placed in front of the detector 218. The double slit aperture provides a well defined geometrical aperture and high signal-to-noise ratio to count cells. As discussed above, signals from the slits may permit the accurate measurement of cell flow velocity, which in turn may permit the calculation of cell diameter.

In some cases, and as shown at 220, a number of parameters may be measured during this analysis, including for example, sample flow rate (FR), measurement time (T) duration, and sample dilution factor (DF). By monitoring the output of the detector(s), and/or the corresponding scatter signature, the number of red blood cells ($N_{RB}$), the number of platelets ($N_{Plt}$), the diameter of each cell (drbc) and the hemoglobin concentration of each cell may be measured.

From these parameters, and as shown at 282, a number of red blood cell analysis parameters may be calculated including, for example, a red blood cell count (RBC=$N_{RB}$/(DF×FR×T)), a platelet count (Plt=$N_{Plt}$/(DF×FR×T)), a mean cell hemoglobin concentration (MCHC=<CHC>), a mean cell volume (MCV=$(\pi/6)\times<drbc^3>$), a mean cell hemoglobin content (MCH=$(\pi/6)\times<drbc^3\times CHC>$), a relative distribution width (RDW=Standard Deviation of $[(\pi/6)\times drbc^3]/MCV$), a Hematocrit parameter (Hct=RBC×MCV) and/or a hemoglobin concentration (Hb=MCHC×Hct).

In the illustrative WBC measurement channel 206, the red blood cells are first lysed as shown at 232, and then hydrodynamically focused and provided single file down a WBC cytometry channel 234 in the removable cartridge. A light source 236, such as a vertical cavity surface emitting laser (VCSEL), shines light on the individual cells as they pass by an analysis region of the WBC cytometry channel 234. In some cases, an array of VCSEL devices is provided, and only the VCSEL(s) that is/are aligned with the individual cells as they pass by the analysis region of the WBC cytometry channel 234 is activated. Some of the incident light provided by the VCSEL is scattered, and a detector 238 detects the scattered light. In some cases, the detector 238 detects forward angle scatter light (FALS), small angle scatter light (SALS), and large angle scatter light (LALS). In some cases, and as shown at 240, a number of parameters may be measured during the analysis including, for example, on-axis cell volume, total WBC count, and WBC five (5) part differentiation.

Figure 7:
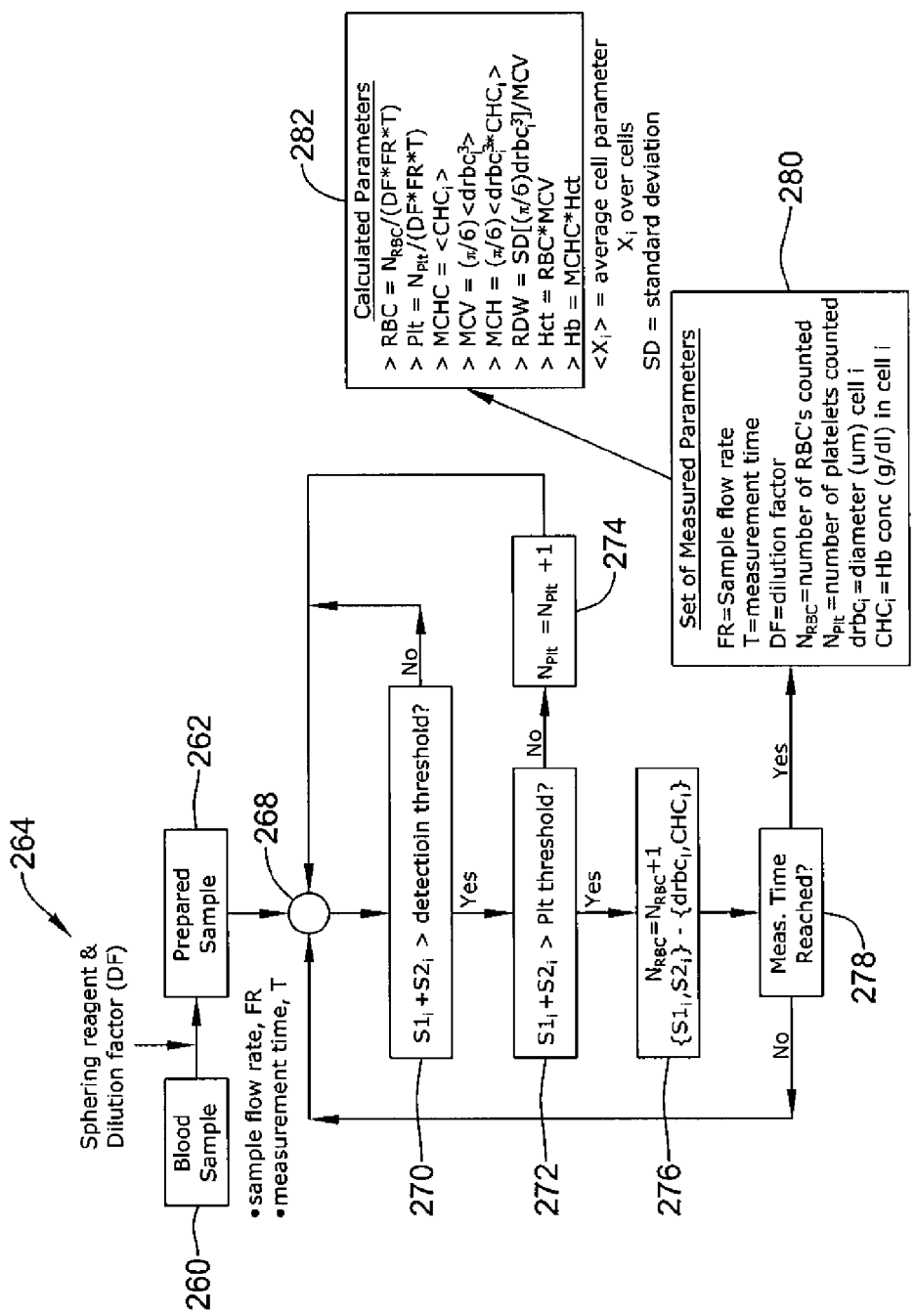
FIG. 7 is a flow diagram showing an illustrative approach for obtaining a number of red blood cell parameters.

FIG. 7 is a flow diagram showing an illustrative approach for obtaining a number of red blood cell parameters. In the illustrative approach, a blood sample is acquired at step 260. Next, the blood sample is diluted to a desired Dilution Factor (DF), and sphered as shown at 264. The diluted and sphered blood cells are then hydrodynamically focused and provided single file down a RBC/P cytometry channel in the removable cartridge. A light source 216, such as a vertical cavity surface emitting laser (VCSEL), shines light on the individual cells as they pass by an analysis region of the RBC/P cytometry channel. Some of the incident light provided by the VCSEL(s) is scattered, and a detector may be used to detect the scattered light. In some cases, the detector detects both Forward Angle Scatter Light (FALS) and Small Angle Scatter Light (SALS) for each cell. A processor or the like may then map the two independent scatter parameters, namely SALS and FALS, for each cell to a cell diameter parameter and a cell hemoglobin concentration parameter as follows:

$\{S_{SALSi}, S_{FALSi}\} \rightarrow \{drbc_i, CHC_i\}$

As shown at 270, if the intensity of the scatter $S_{SALSi}$ plus $S_{FALSi}$ is not greater than a predetermined detection threshold, control is passed back to step 268. However, if the intensity of the scatter $S_{SALSi}$ plus $S_{FALSi}$ is greater than a predetermined detection threshold, control is passed to step 272. Step 272 determines if the sum of $S_{SALSi}$ and $S_{FALSi}$ is greater than a predetermined platelet threshold. If the sum of $S_{SALSi}$ and $S_{FALSi}$ is not greater than the predetermined platelet threshold, it is determined that the particle "i" is a platelet, and control is passed to step 274. Step 274 increments the number of counted platelets ($N_{Plt}$) by one, and passes control back to step 268.

If the sum of $S_{SALSi}$ and $S_{FALSi}$ is greater than a predetermined platelet threshold, the cell is a red blood cell, and control is passed to step 276. Step 276 increments the number of counted red blood cells ($N_{RBC}$) by one, and passes control to step 278. Step 278 determines if a predetermined measurement time has been reached. If not, control is passed back to step 268.

Once the measurement time is reached at step 278, control is passed to step 280. Step 280 shows a number of measured parameters including, for example, sample flow rate (FR), measurement time (T) duration, sample dilution factor (DF), number of red blood cells counted ($N_{RBC}$), number of platelets counted ($N_{Plt}$), the diameter of each cell ($drbc_i$) and hemoglobin concentration of each cell ($CHC_i$). From these parameters, and as shown at step 282, a number of blood cell analysis parameters may be calculated including, for example, a red blood cell count (RBC=$N_{RBC}$/(DF×FR×T)), a platelet count (Plt=$N_{Plt}$/(DF×FR×T)), a mean cell hemoglobin concentration (MCHC=<$CHC_i$>, a mean cell volume (MCV=$(\pi/6)\times<drbc_i^3>$), a mean cell hemoglobin content (MCH=$(\pi/6)\times<drbc_i^3\times CHC_i>$), a relative distribution width (RDW=Standard Deviation of $[(\pi/6)\times drbc_i^3]/MCV$), a Hematocrit parameter (Hct=RBC×MCV) and/or a hemoglobin concentration (Hb=MCHC×Hct), wherein the notation <$X_i$> means the average cell parameter over all cells $X_i$.

FIG. 8 is a schematic flow diagram showing another illustrative approach for analyzing a blood sample. In this illustrative approach, a blood sample is acquired, and provided to a blood sample reservoir, as shown at step 300. Next, the blood sample is provided to an anti-coagulant coated capillary in a removable cartridge, and diluted. The blood sample is then partitioned and provided to a red blood cell and platelet (RBC/P) measurement channel 304 and a white blood cell (WBC) measurement channel 340.

In the REC/P measurement channel 304, the red blood cells are first sphered as shown at 306, and then hydrodynamically focused and provided single file down a RBC/P cytometry channel 308 in the removable cartridge. A first light source 310, such as a vertical cavity surface emitting laser (VCSEL) and associated optics, provides a focused light beam on the individual cells as they pass by an analysis region of the RBC/P cytometry channel 308. In some cases, an array of VCSEL devices is provided, and only the VCSEL(s) that is/are aligned with the individual cells as they pass by an analysis region of the RBC/P cytometry channel 308 is/are activated.

As the individual cells/particles pass through the focused incident light beam, some of the light is blocked, scattered or otherwise obstructed, which can be detected by a detector (not shown). When two or more light sources are focused on different spaced spots along the RBC/P cytometry channel 308, the leading and/or trailing edge of each cell can be detected. By measuring the time it takes for a cell to traverse the distance from one focused spot to the next, the flow rate and thus the cell velocity can be determined. With the cell velocity determined, the length of time that a cell blocks, scatters or otherwise obstructs the light beam can be correlated to cell size and/or cell volume.

In some examples, another light source 314 and associated optics may be provided by an analyzer. The associated optics of light source 314 may collimate the light, and measure off-axis scatter, such as SALS and FALS scatter. As noted above, the SALS and FALS scatter can be used to measure, for example, a number of red blood cells counted ($N_{RBC}$) 316, number of platelets counted ($N_{Plt}$) 322, the diameter of each cell ($drbc_i$) the cell volume 318, and hemoglobin concentration 320 of each cell ($CHC_i$). From these parameters, and as discussed above, a number of blood cell analysis parameters may be calculated including, for example, a red blood cell count (RBC=$N_{RBC}$/(DF×FR×T)), a platelet count (Plt=$N_{Plt}$/(DF×FR×T)), a mean cell hemoglobin concentration (MCHC=<$CHC_i$>), a mean cell volume (MCV=($\pi/6$)×<$drbc_i^3$>), a mean cell hemoglobin content (MCH=($\pi/6$)×<$drbc_i^3$×$CHC_i$>), a relative distribution width (RDW=Standard Deviation of [($\pi/6$)×$drbc_i^3$]/MCV), a Hematocrit parameter (Hct=RBC×MCV) and/or a hemoglobin concentration (Hb=MCHC×Hct), wherein the notation <$X_i$> means the average cell parameter over all cells $X_i$.

In the illustrative WBC measurement channel 340, the red blood cells are lysed, and dye is injected as appropriate, as shown at 342. The cells are then hydrodynamically focused and provided single file down a WBC cytometry channel 344 in the removable cartridge. A light source 346, such as a vertical cavity surface emitting laser (VCSEL), shines light on the individual cells as they pass by an analysis region of the WBC cytometry channel 344. In some cases, an array of VCSEL devices is provided, and only the VCSEL(s) that is/are aligned with the individual cells as they pass by the analysis region of the WBC cytometry channel 344 is activated.

As the individual cells/particles pass through the focused incident light beam, some of the light is blocked, scattered or otherwise obstructed, which can be detected by a detector (not shown). When two or more light sources are focused on different spaced spots along the WBC cytometry channel 344, the leading and/or trailing edge of each cell can be detected. By measuring the time it takes for a cell to traverse the distance from one focused spot to the next, the flow rate and thus the cell velocity can be determined. With the cell velocity determined, the length of time that a cell blocks, scatters or otherwise obstructs the light beam can be correlated to cell size and/or cell volume.

In some examples, a light source 350 and associated optics and/or polarizers may be provided. The associated optics of light source 350 may collimate the light, and measure off-axis scatter, such as SALS, FALS and LALS scatter, as shown at 354. Like above, the SALS, FALS and LALS scatter can be used to measure, for example, the number of white blood cells counted ($N_{WBC}$) 352, as well as to help with white blood cell differentiation, as shown at 356. In some cases, one or more polarizers is/are provided to polarize the light provided by the light source, and the level of polarization extinction/rotation detected at the detector may be used to help perform white blood cell differentiation, but this is not required in all examples.

In the illustrative example, the cells that exit the WBC cytometry channel 344 may be provided to a bulk absorption channel 360. A light source 362 may shine light onto the cells present in the absorption channel 360, and a detector 364 may detect the light that is not absorbed by the resident cells. The absorption channel 360 may thus be used to measure the bulk absorption level of the resident cells. The absorption level may provide, for example, a measure of the bulk or mean cell hemoglobin concentration in the blood sample. The hemoglobin channel may have re-zeroing optics and auto focus and/or alignment. Light source 362 may be a LED having an output close to the center of the absorption peak, thus possibly making a filter unnecessary. There may be a curvette for receiving and holding a sample to be evaluated in terms of hemoglobin. Humidity and temperature sensors may be on the card to indicate present and historical conditions of the card in terms of these parameters. Time of warm-up or cool-down of card may indicate its temperature previous to initialization of operation. Monitoring such conditions may be relevant to materials and solutions on the card. Knowledge of these conditions may be implemented in terms of safeguards to eliminate or significantly reduce the chances of the card or cartridge having a structural de-lamination.

Transfer and movement of fluids without contamination may be achieved with interfaces illustrated in FIGS. 9a through 9f. Once the reagents are stored in a reagents cartridge on the instrument, an issue may be the compressibility of the fluid in each supply line from the reagent reservoir to a fluidic interface. To obtain high fidelity fluid flow control, this issue should be minimized. Compressibility may be due to gas bubbles that originate either from dissolved gases that come out of a solution during temperature changes or from air that diffuses in through the gas-permeable walls of the supply lines. One approach to remove this issue may be to withdraw the bubbly solution, such as a reagent, from the fluidic interface of the instrument to a valve that can route into a waste tank on the reagents cartridge, for example, and replace it with a fresh fluid. Once the bubbles have been reabsorbed or flushed to waste, the valve may be switched again and the fluid/air meniscus returned to the fluidic interface. After the meniscus is returned near the fluidic interface, another issue to resolve may be a potential contamination of the instrument by the blood sample. Several solutions may be provided for controlling the flow of the sample blood and reagents without contact with controlled contact.

Figure 9A:
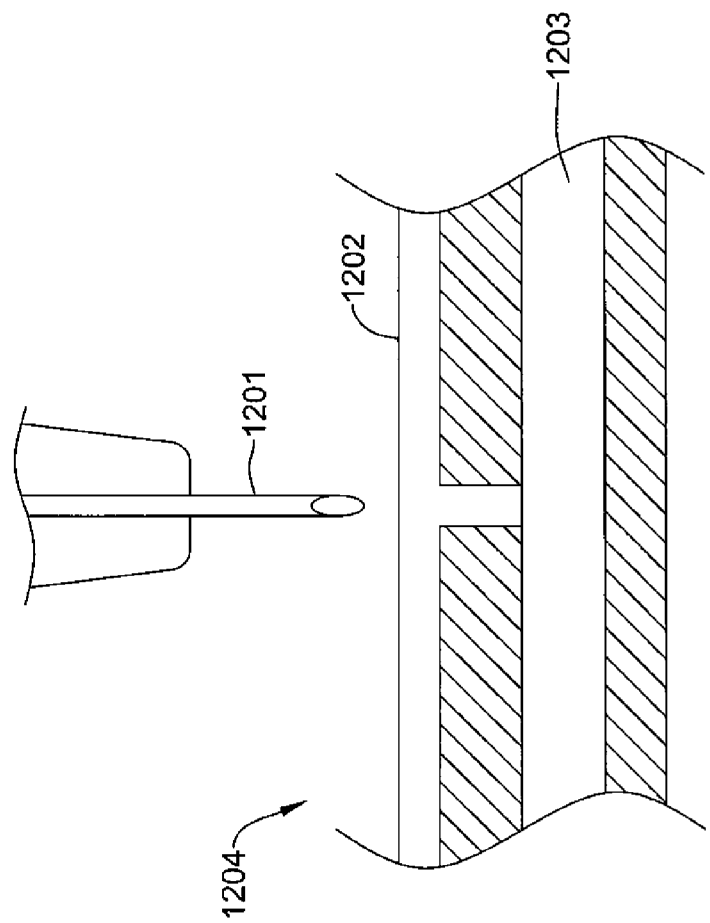
FIGS. 9a, 9b, 9c, 9d, 9e and 9f show the needle-septum interface, shaft-membrane interface and membrane-membrane interface, respectively.
Figure 9B:
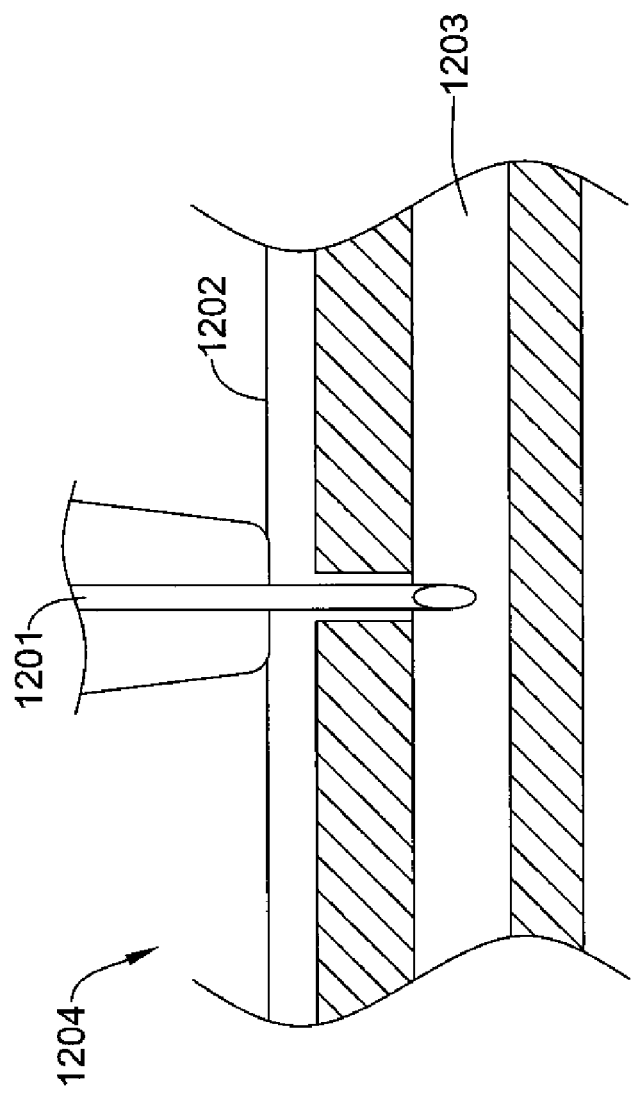

In a needle-septum interface shown in FIGS. 9a and 9b, a needle 1201 may pierce a septum 1202 and deliver liquids stored on the instrument to a channel 1203 the card 1204.

Flow sensors and controllers may be situated on the instrument. At the end of an assay when the needle 1201 is withdrawn, the septum 1202 self-seals and the card is leak-free and ready for disposal. While this approach may work well for introducing reagents stored on the instrument to the card 1204, the sample blood is already present on the card and the needle would touch the blood once it pierces the septum 1202. The bent-tip needle 1201 may be designed specifically for piercing a septum without coring.

In practice, the contamination of the needle 1201 may be minimal and surmountable for several reasons. During an assay, the pusher fluid flushes inside of the needle. At the end of the assay, the outside of the needle 1201 may be wiped by the septum 1202 as the needle is withdrawn. The small scale of the needle 1201 may limit the amount of blood that can be retained on the surface area of its tip. Heat sterilization of the needle tip by the instrument may be a very rapid heat/cool cycle because of the small size and geometric similarity of a needle to a heat transfer pin. The sterilization procedure may be proven experimentally. Also, normally-off valves could prevent backflow of any fluids into the instrument during a power outage.

Figure 9C:
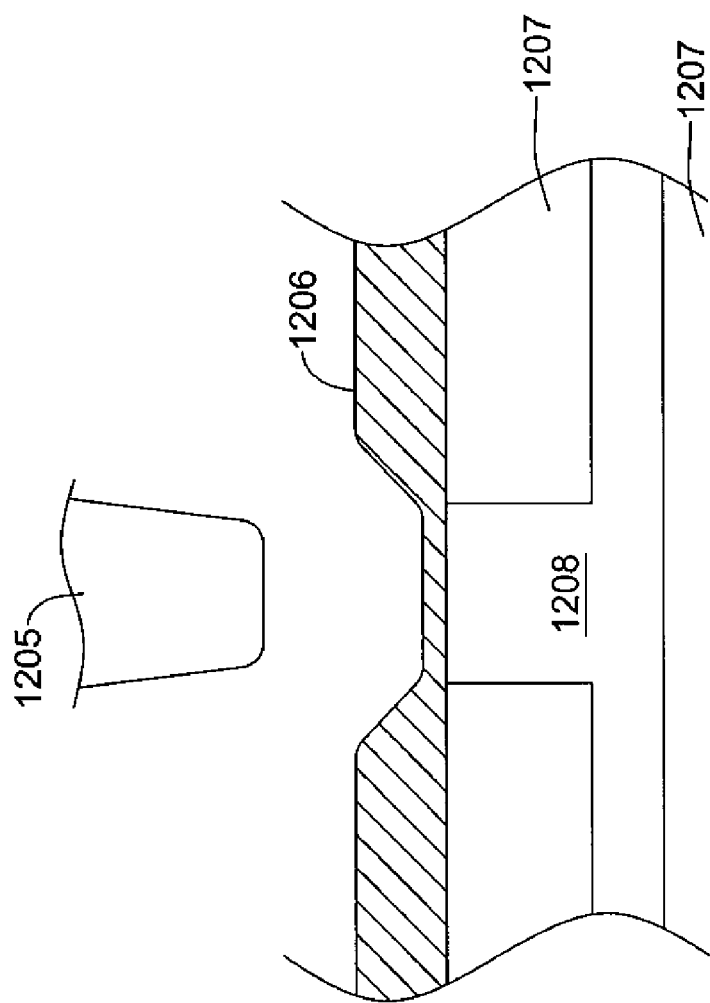
Figure 9D:
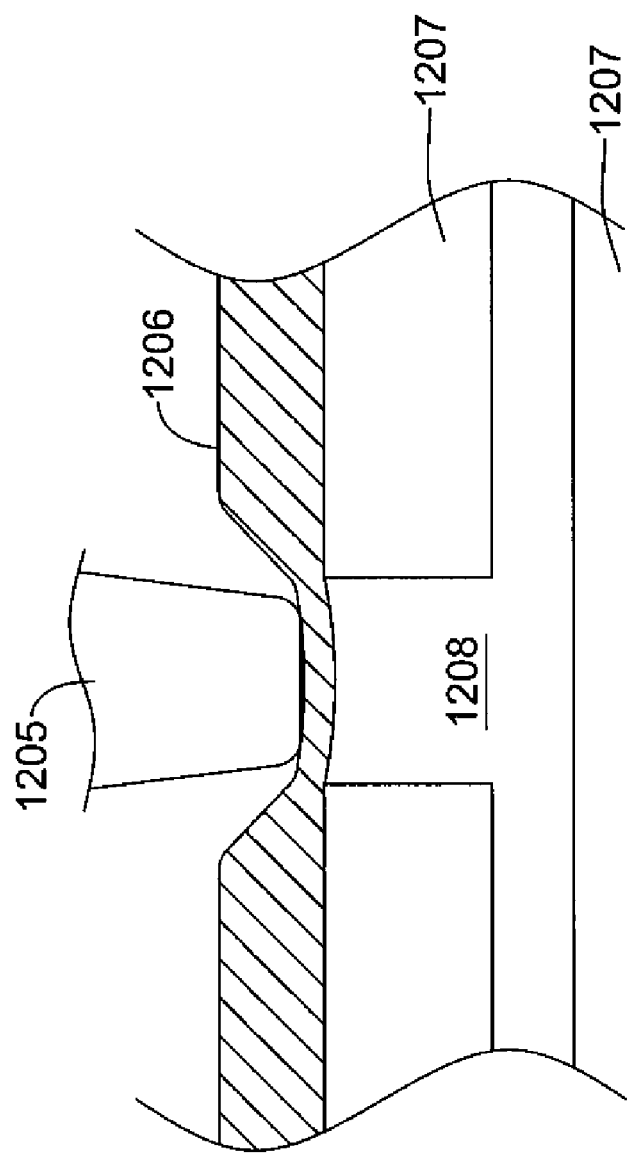

A shaft-membrane interface of FIGS. 9c and 9d may be noted. In this approach, a long thin sample loop may be replaced by a cylindrical sample storage cavity sealed on one end by an elastomeric membrane 1206. Membrane 1206 may be situated on a molded case 1207 and over the sample reservoir 1208. To dispense the sample, a lead screw rotated by a micro stepper motor is advanced against the membrane. This may be essentially a syringe pump that advances a shaft 1205 against membrane 1206 instead of advancing a plunger in a syringe barrel. An advantage of this approach is the physical barrier the membrane 1206 may eliminate the contamination issue.

The approach may involve finding zero displacement of the shaft 1205 (i.e., just touching the membrane 1206) after the card is mounted in the instrument. The volume change response of the sample storage cavity would probably be nonlinear with the shaft displacement and calibration needed. The tip of the shaft 1205 may be designed for displacement efficiency. Delivering 80 percent of the sample in the storage cavity at full stroke of the shaft may be realistic. The membrane 1206 would need to be recessed sufficiently that fingers could not accidentally compress/actuate the membrane and dispense the sample.

Figure 9E:
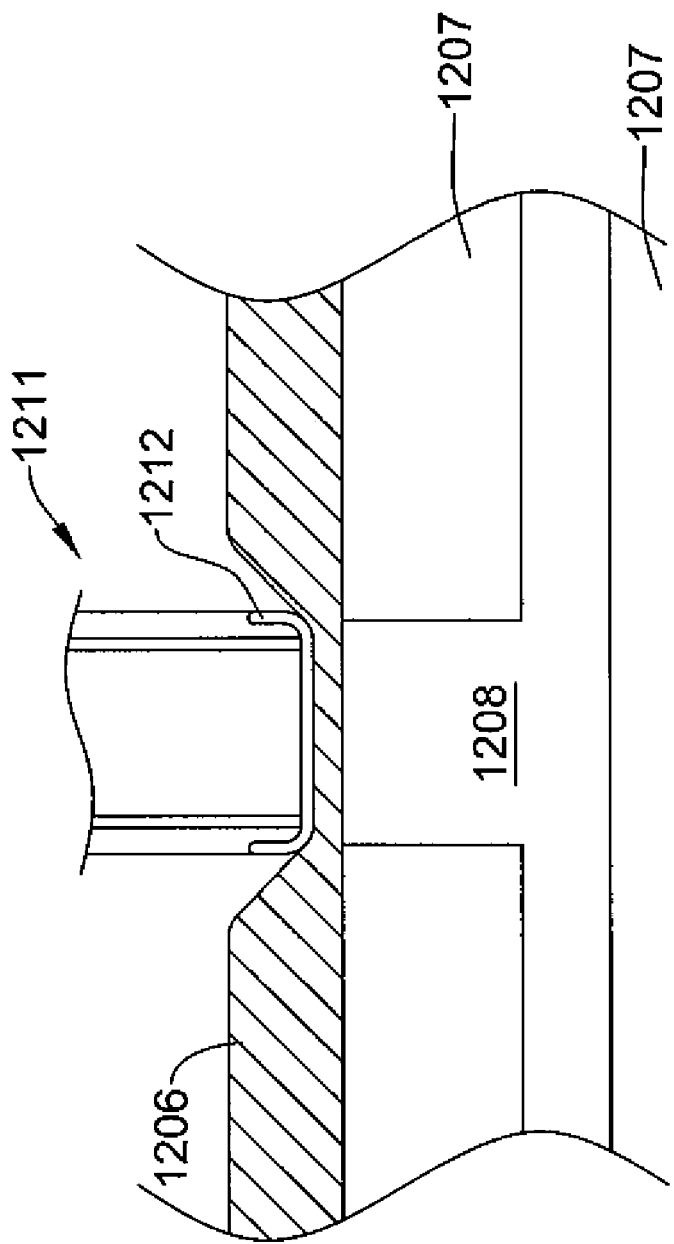
Figure 9F:
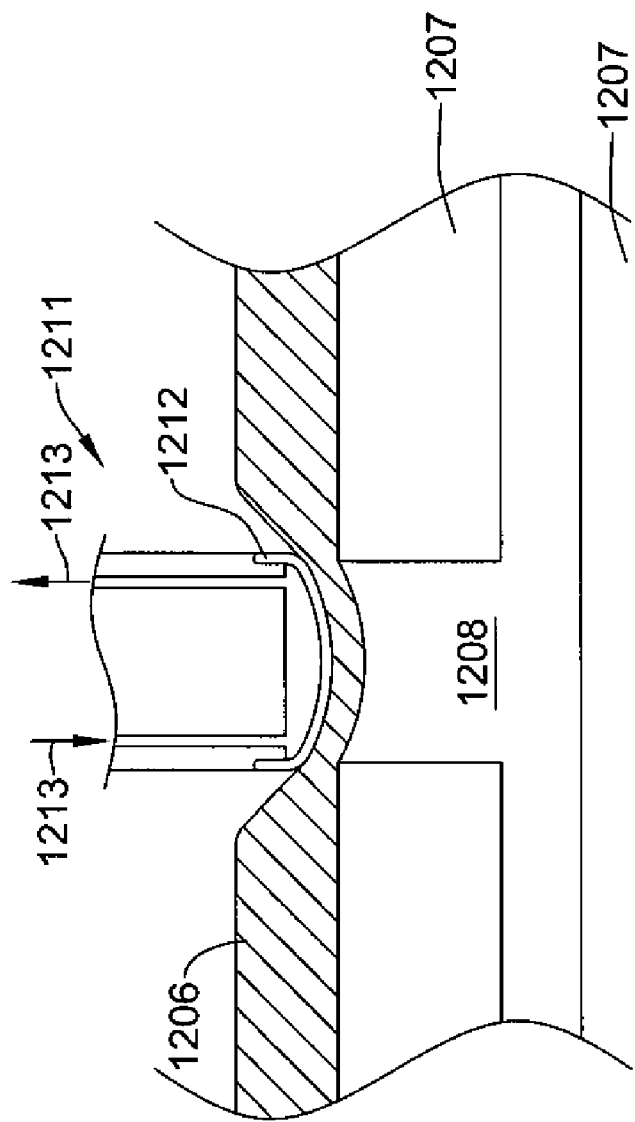

A membrane-membrane interface may be illustrated in FIGS. 9e and 9f. In this approach, the sample may again be stored in a cylindrical reservoir closed at one end by an elastomeric membrane. Membrane 1206 displacement may be caused by an actuator 1211 that has a membrane 1212 closing its tip. If the two membranes 1206 and 1212 are already in contact, pumping actuation fluid 1213 to the actuator 1211 tip may deform both membranes 1212 and 1206, and displace an equal volume of fluid in the sample reservoir 1208.

Some advantages of this approach may be apparent. Flow sensor technology may be used to control the flow rate of the actuation fluid 1213, which ultimately controls the flow rate of the sample. Since the actuation is fluid driven, the membranes 1206 and 1212 naturally tend to deform to provide a high displacement efficiency. This approach may also eliminate the contamination issue by sequestering the blood sample behind a physical membrane.

The approach may involve finding zero displacement after the card is mounted in the instrument so that the membranes 1212 and 1206 are exactly touching without displacing any blood sample. The volume change response in the sample storage cavity 1208 would probably be slightly nonlinear with the volume change of the actuator membrane 1212 and calibration needed. The membrane 1206 on the card should be recessed sufficiently so that fingers would not accidentally compress/actuate the membrane 1206 and dispense the sample.

The sample loop of FIGS. 9e and 9f is not a long narrow channel, but a shallow cylindrical cavity. With good initial contact between the membranes 1212 and 1206 (i.e., no air trapped between them), the volume of actuation fluid 1213 deployed may deflect the membrane by a repeatable amount, which can be calibrated.

There may be dynamics among membrane interfaces. Compliance introduced by elastomeric membranes should be small, since the Poisson ratios of typical elastomers, such as silicone robber and Neoprene, tend to be in the range of 0.45 to 0.50, which is nearly incompressible. Essentially, elastomers are deformable, but not compressible; their shape changes easily but their volume does not. Thus, a membrane-membrane interface, in which the hard materials of the molded case and the actuator limit the shape changes of the elastomers, should not experience a significant dynamic effect from the low compliance of the elastomers.

A deflection of a membrane 1206 cannot dispense all of the sample or reagent contained in a storage cavity. The proportion dispensed may be characterized by a displacement efficiency. An efficiency of $\epsilon=80$ percent should be reasonable. If one also assumes a ratio of membrane deflection to cavity diameter (for example, $\delta=1/3$), then the volume displaced may be approximately $$V_{disp}=\epsilon\delta(\pi/4)d^3$$

The diameter of the storage cavity may be estimated from $$d=((4V_{disp}/((\epsilon\delta\pi))^{1/3}.$$

A table in FIG. 9g lists the diameter of the storage cavity that may be adequate for a sample pusher fluid and each of the reagents, assuming the assay would run for 4 minutes, half for RBC and half for WBC measurement. The size of the on-card reagent storage cavities for sphering solution and sheath solution might be considered on a sufficiently-sized card.

There may be significant advantages to supplying reagents by a needle-septum interface from a reagent storage cartridge contained in the instrument. The blood sample may be controlled either by a membrane-type interface or by a needle-septum interface if a compact sterilization mechanism is provided on the instrument.

Figure 10:
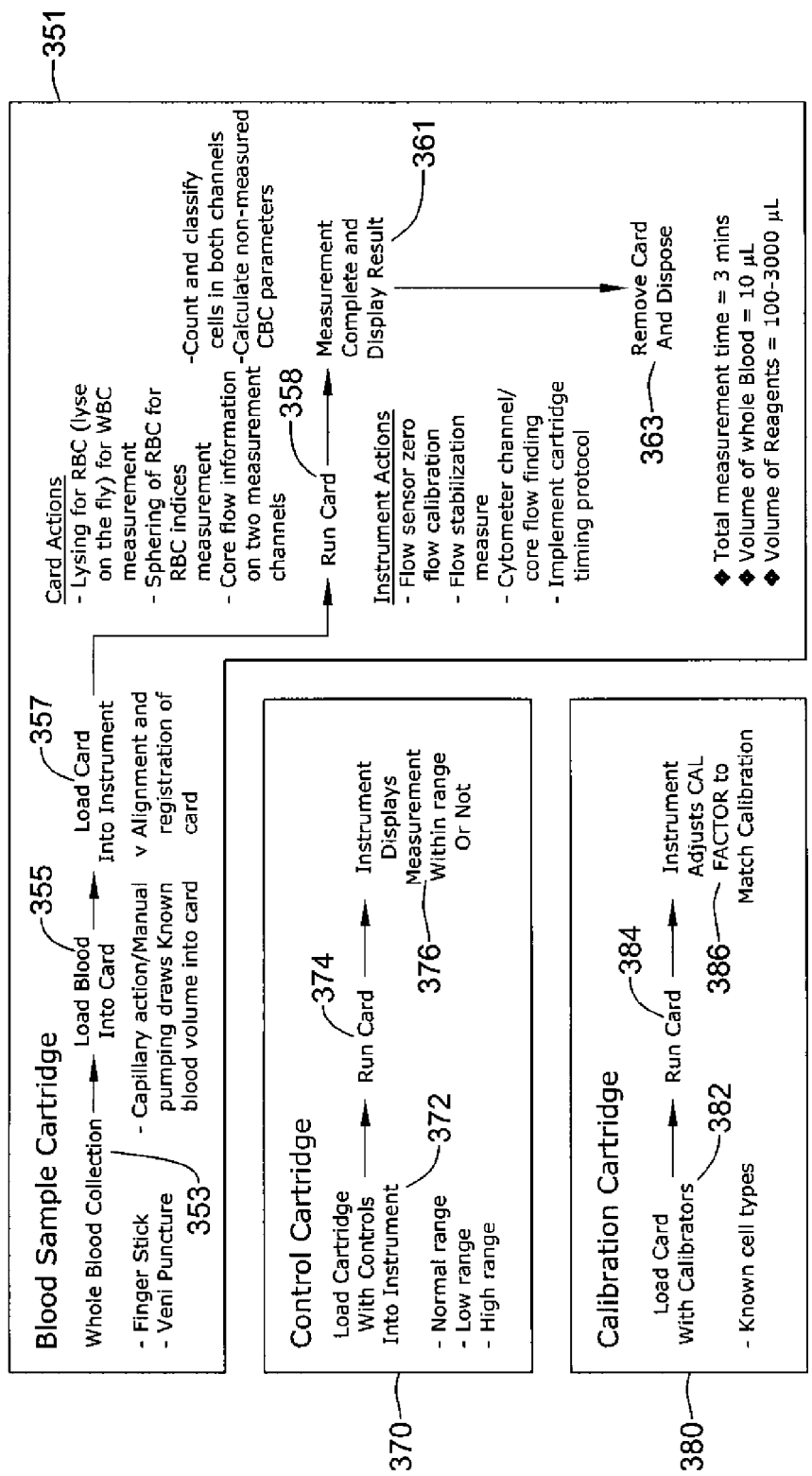
FIG. 10 is a schematic flow diagram showing an illustrative approach for setting up and operating a sample analyzer.

FIG. 10 is a schematic flow diagram showing an illustrative approach for setting up and operating a sample analyzer. In the illustrative example, a blood analysis cartridge may be used and analyzed as shown at 351, a control cartridge may be used and analyzed to help verify the performance of the analyzer as shown at 370, and/or a calibration cartridge may be used and analyzed to help calibrate the analyzer as shown at 380. The blood analysis cartridge may be loaded each time a blood analysis is to be performed. The control cartridge may be loaded into the analyzer at 372 and be run at 374 on a periodic basis, such as once a day, to verify that the analyzer is producing accurate results. The instrument may display indications whether the measurement is within range or not at 376. The indications may depend on whether the measurement is in a normal, low or high range. At 380, the calibration cartridge may be loaded with calibrators at 382 and run at 384. The instrument may adjust a calibration factor to match a calibration at 386. The calibration card may be loaded into the analyzer on a less frequent basis than the control card, such as once every three months, to recalibrate the analyzer. Calibration may include doing a preliminary or post operation precision bead flow through the flow channel to provide such things as scaling of a pulse width which provides information of the size of the particles going through the channel.

Each cartridge may include all of the necessary fluids and/or components to perform the corresponding function. As such, very little training may be needed to operate and/or maintain the analyzer, while still achieving accurate results. The ability to provide a sample analyzer with removable and/or disposable cartridges that can be reliably used outside of the laboratory environment, by personnel with no specialized training, may help streamline the sample analysis process, reduce the cost and burden on medical personnel, and increase the convenience of sample analysis for many patients, including those that require relatively frequent blood monitoring/analysis. The system may note whether the reagents and/or sample fluid is spoiled, not fresh, contaminated, incorrect, or otherwise inappropriate or unacceptable. The resultant action by the system may include not performing an analysis, not providing a result, providing an error indication, and/or the like.

When a blood analysis cartridge is used as shown at 351, a blood sample may be collected and loaded into the blood analysis cartridge, as shown at 353 and 355. The blood sample may be drawn into the blood analysis cartridge by capillary action or manual pumping, as desired. The blood analysis cartridge may then be loaded into the analyzer instrument. In the illustrative example, the analyzer may then self-align the blood analysis cartridge and the corresponding components (e.g., light sources/light detectors, and so on) of the analyzer, as shown at 357. Next, one or more buttons may be pushed to begin the blood analysis process. Rather than pushing a button or the like, and in some cases, the step of simply loading the cartridge into the analyzer may cause the analyzer to initiate the alignment and blood analysis process.

The card may be run at 358. Once the analyzer is activated, the analyzer may perform a number of tests. For example, the analyzer may close all of the valves on the blood analysis card and apply pressure to the various fluid ports on the card. The analyzer may then measure the flow rate flowing past one or more flow sensors on the card. The flow should be zero, since all of the valves are closed. However, if the flow sensors indicate a non-zero flow rate, the analyzer may recalibrate the flow sensors back to a zero flow. This may help increase the accuracy of the flow sensor measurements. The analyzer may check and institute a bubble removal approach as needed. Alternatively, or in addition, the analyzer may check for blood clotting in the removable cartridge by, for example, measuring the flow rate of the blood sample (e.g., using a flow sensor) along with the pressure applied, and if the flow rate is too low relative to the applied pressure, determining that the blood sample has clotted. If blood clotting is detected, the analyzer may display a message that indicates that the measurement has failed.

The analyzer may then implement a blood analysis cartridge timing protocol. The blood analysis cartridge timing protocol may be similar to that shown and described in U.S. patent application Ser. No. 10/932,662, filed Sep. 2, 2004, which is assigned to the assignee of the present invention and hereby incorporated by reference. The particular blood analysis cartridge timing protocol may depend on the specific design of the blood analysis cartridge. The analyzer may also verify that there is a stable core flow in any cytometry channels on the blood analysis cartridge, and identify the location of the core flow if present.

The blood analysis cartridge may then, for example, lyse red blood cells in a portion of the blood sample that will be used for white blood cell measurements, sphere the red blood cells in a portion of the blood sample that will be used for red blood cell measurements, form core flows in any cytometry channels on the blood analysis cartridge, and/or perform any other desirable function. The analyzer may provide light to selected regions of the blood analysis cartridge, such as any cytometry channels, and detect light that passes through the selected regions.

From this, the analyzer may count and classify particles in the sample such as white blood cells, red blood cells, platelets, and so on, and then display, print, produce a sound, or otherwise indicate a result of the blood analysis to a user. In some examples, the analyzer displays or prints out quantitative results (e.g., inside and/or outside of a predefined range), such that no further calculations or interpretation is required by the user. Measurement may be regarded as complete and result displayed at 361. Finally, the blood analysis cartridge may be removed from the analyzer, and disposed of at 363.

When a control run is to be performed as shown at 370, a control cartridge may be used. In some cases, a control run may be performed periodically, such as once a day or once a week. The control cartridge may include a control sample that has known characteristics. Thus, when an analysis is performed by the analyzer on the control sample, a known result should be achieved. In the illustrative approach, a control cartridge is loaded into the analyzer, as shown at 372. Next, the analyzer is activated as shown at 374, and the analyzer performs an analysis and displays a result as shown at 376. In some examples, the analyzer displays or prints out quantitative results (e.g., inside and/or outside of a predefined range), such that no further calculations or interpretation is required by the user. Finally, the control cartridge may be removed from the analyzer, and disposed of. If the results of the control run are outside of a predefined range, it may be desirable to perform a calibration run, such as calibration run 380.

When a calibration run is to be performed as shown at 380, a calibration cartridge may be used. In some cases, a calibration run may be performed periodically, such as one a month, or as otherwise needed. The calibration cartridge may include a calibration sample with known characteristics. Thus, when an analysis is performed by the analyzer on the calibration sample, a known result should be achieved. In the illustrative approach, a calibration cartridge is loaded into the analyzer, as shown at 382. Next, the analyzer is activated as shown at 384, and a number of results are obtained. By comparing the results obtained during the calibration run with expected results, the analyzer may automatically adjust one or more calibration factors in memory to recalibrate the analyzer so that, during a subsequent run, the analyzer will produce the expected or desired results, as shown at 386.

Figure 11A:
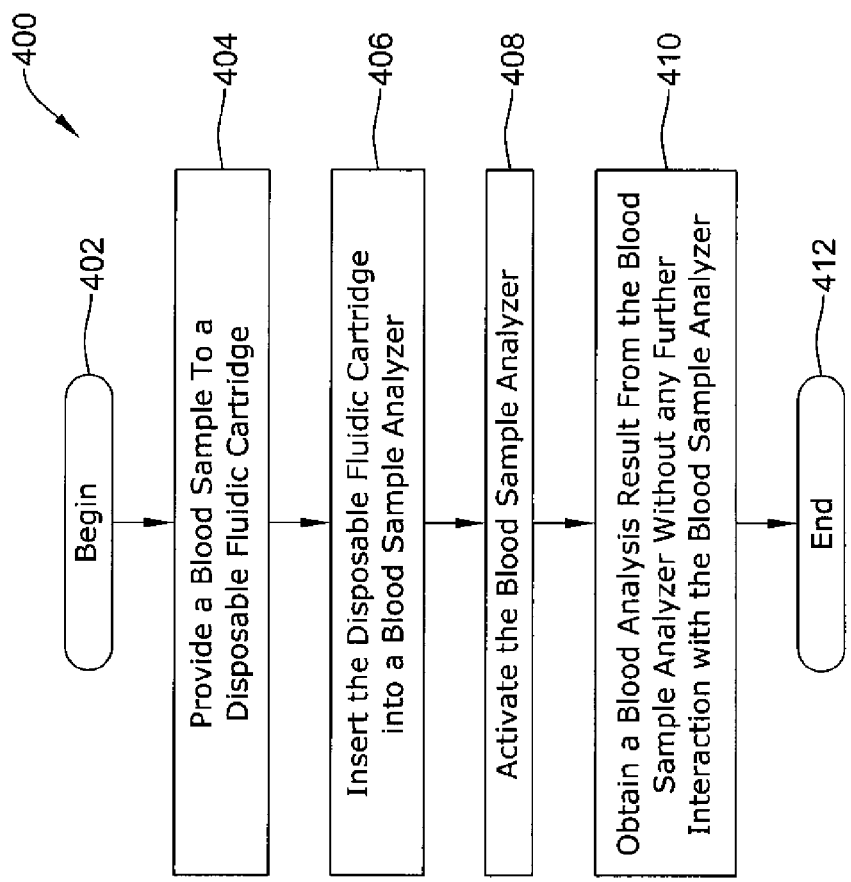
FIG. 11a is a flow diagram showing an illustrative approach for operating a sample analyzer.

FIG. 11*a* is a flow diagram showing an illustrative approach for operating a sample analyzer. The illustrative approach is generally shown at 400, and is entered at step 402. Control is passed to step 404, wherein a blood sample is provided to a disposable fluidic cartridge. Control is then passed to step 406, wherein the disposable fluidic cartridge is inserted into a blood sample analyzer. Control is then passed to step 408. Step 408 activates the blood sample analyzer, and step 410 obtains a blood analysis result from the blood sample analyzer without any further interaction from the user of the blood sample analyzer. Control is then passed to step 412, wherein the approach is exited.

Figure 11B:
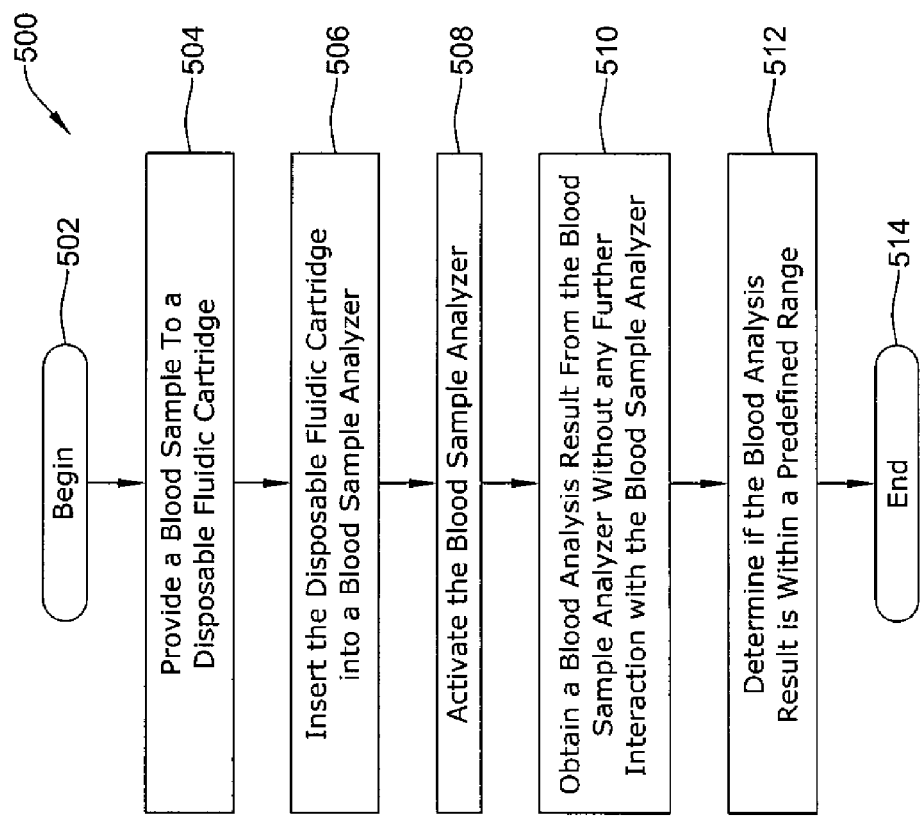
FIG. 11b is a flow diagram showing another illustrative approach for operating a sample analyzer.

FIG. 11*b* is a flow diagram showing another illustrative approach for operating a sample analyzer. The illustrative approach is generally shown at 500, and begins at step 502. Control is passed to step 504, wherein a blood sample is provided to a disposable fluidic cartridge. Control is then passed to step 506, wherein the disposable fluidic cartridge is inserted into a blood sample analyzer. Control is then passed to step 508. Step 508 activates the blood sample analyzer, and step 510 obtains a blood analysis result from the blood sample analyzer without any further interaction from the user of the blood sample analyzer. Control is then passed to step 512. Step 512 determines if the blood analysis result is within a predefined range. As indicated above, and in some examples, the analyzer may display or print out quantitative results (e.g., inside and/or outside of a predefined range), such that no further calculations or interpretation is required by the user. Control is then passed to step 514, wherein the approach is exited.

Figure 12:
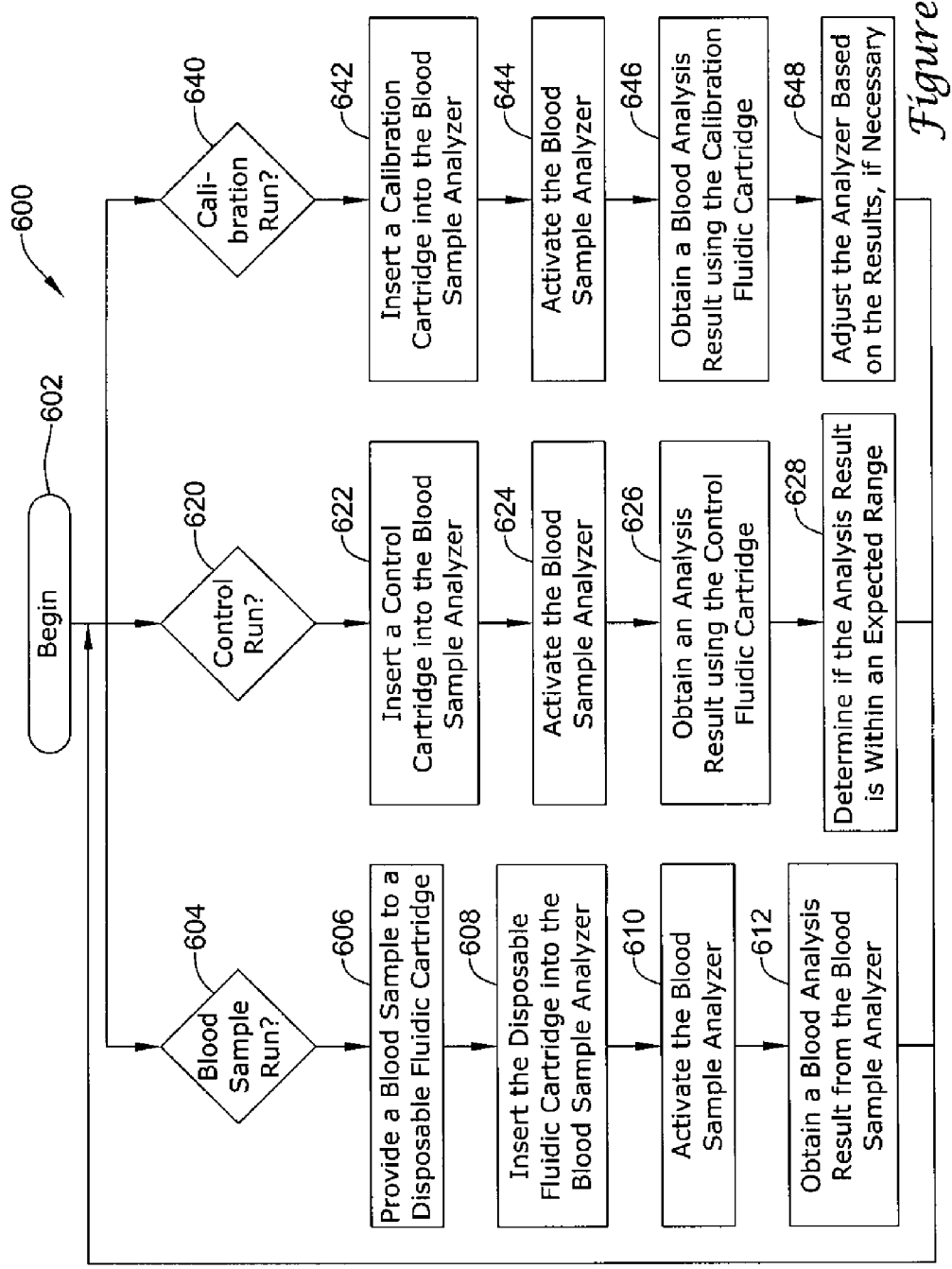
FIG. 12 is a flow diagram showing another illustrative approach for operating a sample analyzer.

FIG. 12 is a flow diagram showing another illustrative approach for operating a sample analyzer. The approach is generally shown at 600, and is entered at step 602. In the illustrative approach, a blood analysis cartridge may be used and analyzed as shown at 604, a control cartridge may be used and analyzed to help verify the performance of the analyzer as shown at 620, and/or a calibration cartridge may be used and analyzed to help calibrate the analyzer as shown at 640. The blood analysis cartridge may be loaded each time a blood analysis is to be performed. The control cartridge may be loaded into the analyzer on a period basis, such as once a day, to verify that the analyzer is producing accurate results. The calibration cartridge may be loaded into the analyzer on a less frequent basis, such as once every three months, to recalibrate the analyzer, or as otherwise needed.

Each cartridge type may include all of the necessary fluids and/or components to perform the corresponding function. As such, very little training may be needed to operate and/or maintain the analyzer, while still achieving accurate results. The ability to provide a sample analyzer with removable and/or disposable cartridges that can be reliably used outside of the laboratory environment, with little or no specialized training, may help streamline the sample analysis process, reduce the cost and burden on medical personnel, and increase the convenience of sample analysis for many patients, including those that require relatively frequent blood monitoring/analysis.

In the illustrative approach of FIG. 12, when a blood analysis cartridge is to be used, control is passed to step 604. At step 606, a blood sample is provided to a disposable fluidic cartridge. Control is then passed to step 608, wherein the disposable fluidic cartridge is inserted into the blood sample analyzer. Control is then passed to step 610. Step 610 activates the blood sample analyzer, and step 612 obtains the blood analysis result from the blood sample analyzer.

When a control cartridge is to be used, control is passed to step 620. Step 620 passes control to step 622, wherein a control cartridge is inserted into the blood sample analyzer. Control is then passed to step 624. Step 624 activates the blood sample analyzer, and step 626 obtains a control analysis result using the control fluidic cartridge. Control is then passed to step 628. Step 628 determines if the control analysis result is within an expected control range. If the control analysis result is not within an expected range, the results obtained for a blood analysis cartridge should not be trusted. In some cases, a calibration cartridge may be run to re-calibrate the sample analyzer, followed by another control cartridge to verify the operation/calibration of the sample analyzer.

When a calibration cartridge is to be used, control is passed to step 640. Step 640 passes control to step 642. Step 642 inserts a calibration cartridge into the blood sample analyzer. Control is then passed to step 644. Step 644 activates the blood sample analyzer, and step 646 obtains a calibration analysis result using the calibration fluidic cartridge. Control is then passed to step 648. Based on the calibration analysis results, step 648 adjusts the analyzer as necessary.

In some cases, the sample analyzer may be a fully automated instrument, a unitized, and/or self-contained test instrument. The sample analyzer may accept and analyze direct unprocessed specimens such as, for example, capillary blood (finger stick) venous whole blood, nasal swabs, or urine to name just a few. Alternatively, or in addition, the sample analyzer may need only basic, non-technique-dependent specimen manipulation, including any for decontamination. Likewise, the sample analyzer may only need basic, non-technique-dependent reagent manipulation, such as "mix reagent A and reagent B", and may need no operator intervention during the analysis steps. In some cases, the sample analyzer may include or provide instructions (and in some cases materials, for obtaining and shipping specimens for confirmation testing, in cases where such testing is clinically advisable.

A quick reference instruction guide may be provided with the sample analyzer. The quick reference guide may provide a quick reference to the operation of the sample analyzer. During use, a user may refer to the quick reference guide should he/she have any questions on how to operate the sample analyzer.

In some cases, the quick reference guide may include self-explanatory pictures or diagrams that graphically illustrate the various operational steps, sometimes from sample collection through analysis. In one illustrative example, the quick reference guide only includes pictures or diagrams, and does not include words or includes a minimum amount of words. This may help users that are not literate in a particular language (e.g., English), to effectively operate the sample analyzer. In one illustrative example, the quick reference guide may show and/or describe the steps of: taking a disposable cartridge from it's package; removing a blood fill cap from a lancet of the cartridge and/or removing a cover (e.g., tape) from a marker that turns color after a predetermined time period after the maker is exposed to air; drawing blood from the patient; providing the drawn blood to the cartridge; loading the cartridge into the instrument; running the instrument and receiving the results; and removing the cartridge from the instrument and disposing the cartridge. This is just one example.

It is contemplated that the housing of the instrument may include a pocket or the like for receiving a quick reference guide. During use, a user may slide the quick reference guide out from the pocket for reference. Alternatively, a quick reference guide may be secured to a housing of the sample analyzer by a spiral binder or the like, which may allow the user to flip through various pages of the quick reference guide during use. In another illustrative example, a quick reference guide may be secured to a removable cartridge, or may be printed on a package containing a removable cartridge. In yet another illustrative example, a quick reference guide may be printed on a poster, which can be hung on a wall or the like adjacent to the sample analyzer.

In some cases, and to further reduce the risk of producing an erroneous result, one or more failure alert and/or fail safe mechanisms may be provided. For example, and in one illustrative example, the sample analyzer may help detect when an incorrect specimen type is provided by the user. For example, if the sample analyzer is set up to perform a white blood cell count of a whole blood sample, the sample analyzer may help detect when the specimen provided by the user is something other than blood.

In one illustrative example, the sample analyzer may perform the analysis, and if one or more output parameters are outside of a predetermined range, the sample analyzer may not provide a result and/or issue an error message or error code. For example, if the sample analyzer is a flow cytometer adapted to count white blood cells in a whole blood sample, and the sample analyzer does not count any white blood cells (or a low number of white blood cells), the sample analyzer may not provide a result, and in some cases, provide an error message or error code.

Figure 13:
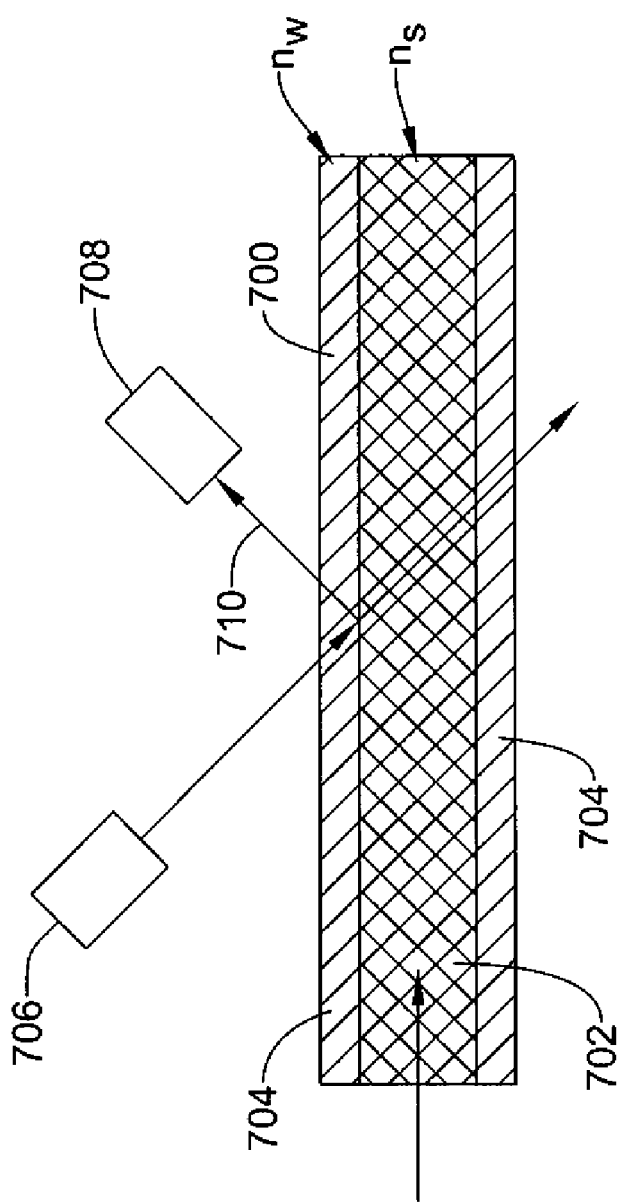
FIG. 13 is a schematic diagram of an illustrative optical measurement that may be used to help identify when an incorrect or undesirable fluid is in a flow channel of a fluidic circuit.

In some examples, one or more optical measurements may be used to help identify when an incorrect fluid is in a flow channel, such as when an incorrect specimen is provided by the user, or when reagents are not provided to the correct flow channels of a fluidic cartridge. FIG. 13 shows one such optical measurement. In FIG. 13, a sample fluid 700 is present in a channel 702 defined by channel walls 704 of, for example, a fluidic cartridge. In the illustrative example, the channel walls 704 have an index of refraction of "$n_w$", and the sample fluid has an index of refraction of "$n_s$". A light source 706 provides an incoming light beam (sometimes a collimated light beam) at an angle relative to one of the channel walls 704. A detector 708 is positioned to detect light 710 that is reflected from the channel wall/sample interface. The amount of light that is reflected to the detector 708 from the channel/sample interface will be dependent on the relative refractive indexes of the channel wall "$n_w$" and the sample fluid "$n_s$". A desired reflected amount or reflected signature may be determined when a desired sample fluid 700 is in the channel 702. When an incorrect specimen type or incorrect reagent or other incorrect sample fluid is provided to the flow channel 700, the refractive index of the incorrect sample fluid "$n_{ic}$" may cause a different reflected signature of light 710 to be measured by the detector 708. Such a change may indicate that an incorrect sample fluid is in the flow channel 702. Alternatively, or in addition, such a change may indicate the presence of bubbles, clots, or other undesirable particles or other characteristics of the sample fluid. When so detected, the sample analyzer may not provide a result, and in some cases, may issue an error message or error code to the user.

Figure 14:
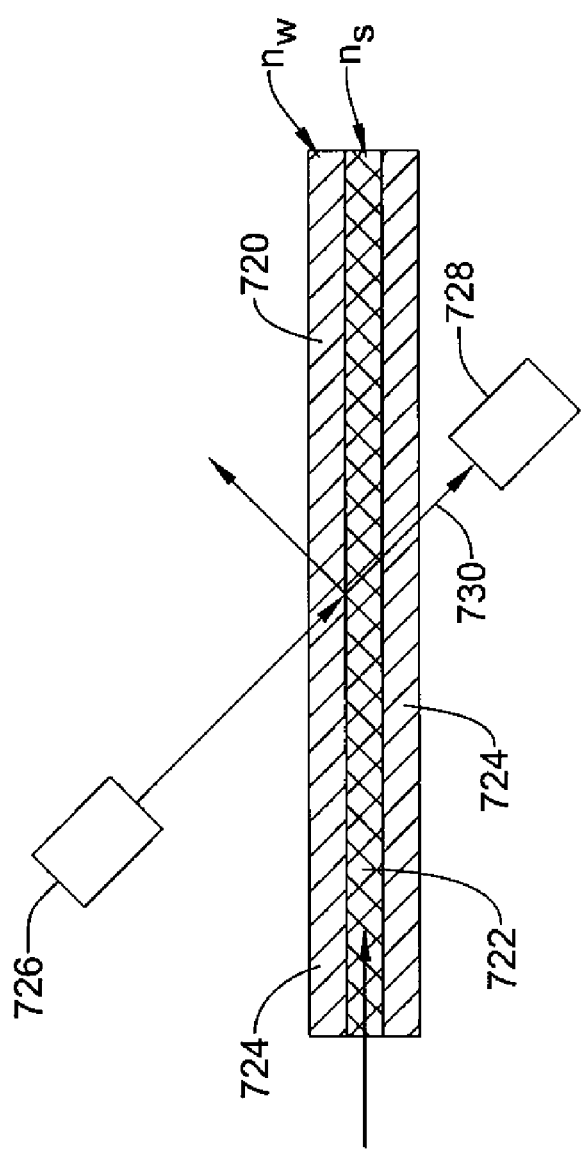
FIG. 14 is a schematic diagram of another illustrative optical measurement that may be used to help identify when an incorrect or undesirable fluid is in a flow channel of a fluidic circuit.

FIG. 14 shows another optical measurement that may be used to help identify when an incorrect or undesirable fluid is in a flow channel. In FIG. 14, a sample fluid 720 is present in a flow channel 722 defined by channel walls 724 of, for example, a fluidic cartridge. In the illustrative example, the channel walls 724 have an index of refraction of "$n_w$", and the sample fluid has an index of refraction of "$n_s$". A light source 726 provides an incoming light beam (sometimes a collimated light beam) at an angle relative to one of the channel walls 724. A detector 728 is positioned to detect light 730 that passes through the channel 722 and the sample fluid 720.

In this illustrative example, the channel 722 is made thin enough so that optical tunneling is permitted through the channel 722 and the sample fluid 720 when the index of refraction "$n_w$" of sample fluid is within a desired range. If the index of refraction "$n_s$" of the sample fluid is below the desired range, the light will not tunnel through the channel 722, but rather, will be reflected. If the index of refraction "$n_s$" of the sample fluid is above the desired range, the light will tend to pass through the channel 722 and the sample fluid 720, and so this example may be most suitable for detecting incorrect sample fluids that have an index of refraction "$n_s$" that is less than the index of refraction of the desired sample (e.g., blood). Alternatively, or in addition, this illustrative example may be useful for detecting the presence of bubbles, clots, or other undesirable particles or other characteristics of the sample fluid, as desired. When so detected, the sample analyzer may not provide a result, and in some cases, may provide an error message or error code.

Figure 15:
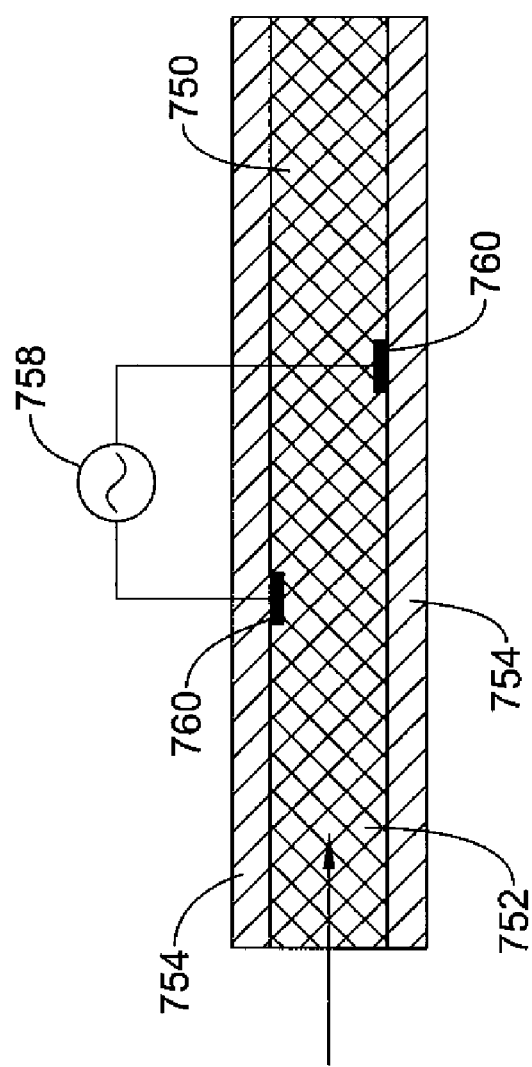
FIG. 15 is a schematic diagram of an electrical measurement that may be used to help identify when an incorrect or undesirable fluid is in a flow channel of a fluidic circuit.

FIG. 15 is another illustrative example that may be useful for identifying when an incorrect or undesirable fluid is in a flow channel of, for example, a fluidic cartridge. In this illustrative example, a sample fluid 750 is provided in a flow channel 752 defined by channel walls 754. In the illustrative example, two or more electrodes 760 are provided on one or more of the channel walls 754. In some examples, the two or more electrodes 760 may be formed on one or more sheets of plastic, which are later laminated or otherwise secured together to form the fluidic circuit of the fluidic cartridge. The two or more electrodes may be patterned to extend into or across a flow channel 752 on the fluidic cartridge and connect into a desired drive circuit.

A power source 758 may provide a signal between the electrodes 760, and may measure the resistance between the electrodes through the sample fluid 750. This may provide a measure of the resistivity of the sample fluid 750 in the channel 752. When an incorrect sample fluid is present in the flow channel 752, the resistivity of the incorrect sample fluid may be outside of an expected range. Having a resistivity that is outside of the expected range may also indicate the presence of bubbles, clots, or other undesirable particles or other characteristics of the sample fluid. When so detected, the sample analyzer may not provide a result, and in some cases, may provide an error message or error code.

In some cases, the power source 758 may provide a low electric potential AC signal (e.g., less than 10V peak-to-peak, less than 5V peak-to-peak, less than 3V peak-to-peak, less than 1V peak-to-peak, less than 0.5V peak-to-peak, or less than 0.1V peak-to-peak) to limit electrochemical reactions in the sample fluid 750 caused by the electrodes 760. Electrochemical reactions may, for example, introduce bubbles or the like into the sample fluid 750, which may be undesirable in some applications.

In addition to, or instead of using a resistivity measurement as described above, it is contemplated that a capacitance measurement may be used. In this illustrative example, the capacitance between the two or more electrodes may be measured through the sample 750. When an incorrect sample fluid is provided to the flow channel 752, the capacitance resulting from the incorrect sample fluid may be outside of an expected range. Having a capacitance that is outside of an expected range may also indicate the presence of bubbles, clots, or other undesirable particles or other characteristics of the sample fluid. When so detected, the sample analyzer may not provide a result, and in some cases, may provide an error message or error code.

Figure 16:
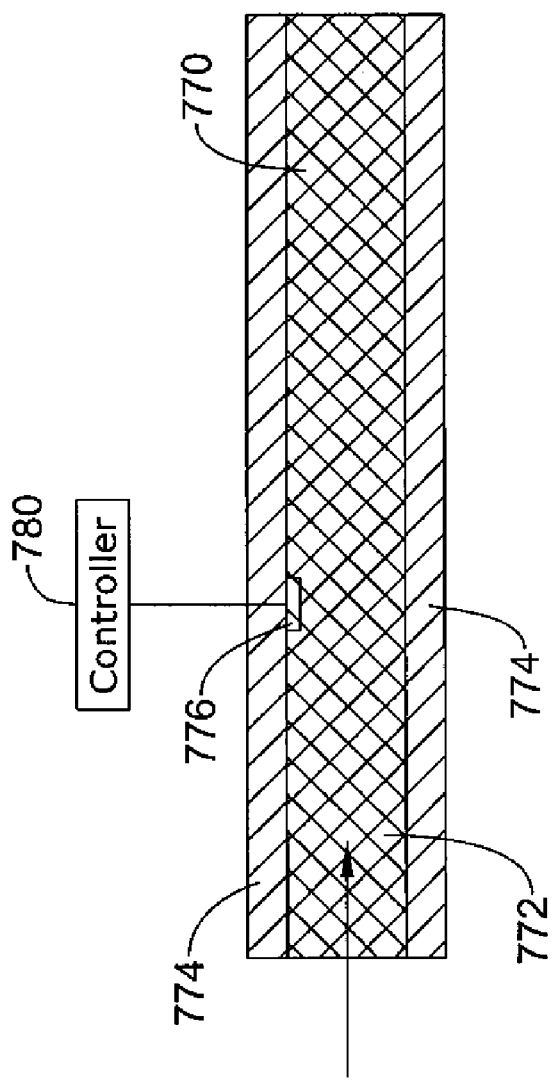
FIG. 16 is a schematic diagram of another measurement that may be used to help identify when an incorrect or undesirable fluid is in a flow channel of a fluidic circuit.

FIG. 16 is another illustrative example that may be useful for identifying when an incorrect or undesirable fluid is in a flow channel of, for example, a fluidic cartridge. In this illustrative example, a sample fluid 770 is provided in a flow channel 772 defined by channel walls 774. In the illustrative example, a PH sensor 776 is provided in fluid communication with the sample fluid 770. The PH sensor 776 may detect a measure of the PH of the sample fluid 770, and report a signal to Controller 780. When an incorrect sample fluid is provided to the flow channel 772, the PH of the incorrect sample fluid may be outside of an expected range. Having a PH level that is outside of an expected range may also indicate the presence of bubbles, clots, or other undesirable particles or other characteristics of the sample 770. When so detected, the sample analyzer may not provide a result, and in some cases, may provide an error message or error code.

Figure 17:
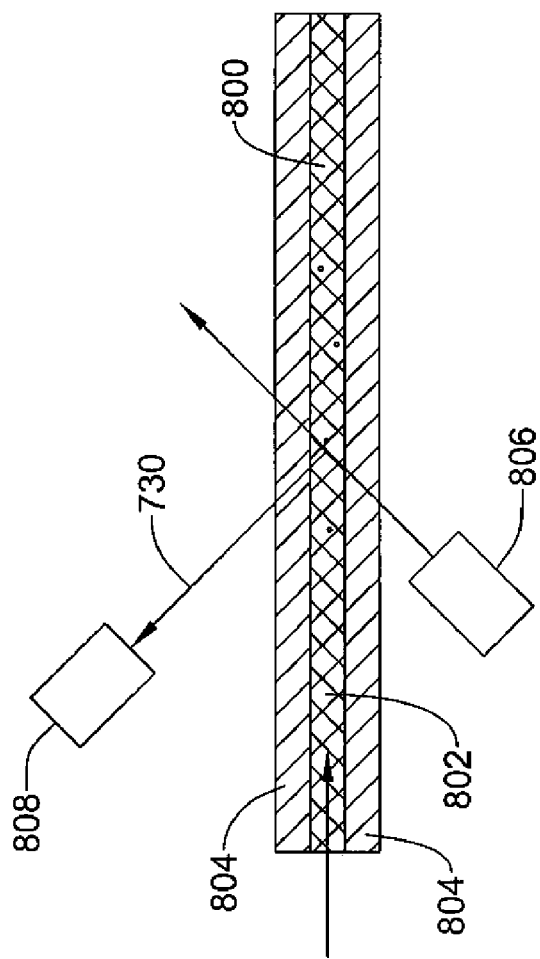
FIG. 17 is a schematic diagram of an illustrative example that may be useful in identifying when a sample fluid in a flow channel has one or more bubbles or other undesirable particles.

FIG. 17 is an illustrative example that may be useful for identifying when a sample fluid in a flow channel has one or more bubbles or other undesirable particles. In this illustrative example, a sample fluid 800 is present in a flow channel 802 defined by channel walls 804 of, for example, a fluidic cartridge. A light source 806 provides an incoming light beam (sometimes a collimated light beam) at an angle relative to one of the channel walls 804. A detector 808 is positioned to detect light 730 that is scattered by bubbles or other undesirable particles in the sample fluid 800 in the flow channel 802. If, for example, the sample fluid 800 does not have any bubbles, the light will tend to pass un-scattered through the sample fluid, and the detector 808 will not detect a signal (or a low signal). When a light scatter signal above a certain threshold is detected by detector 808, indicating the sample fluid 800 in the flow channel 802 has one or more bubbles or other undesirable particles, the sample analyzer may not provide a result, and in some cases, may provide an error message or error code.

Figure 18:
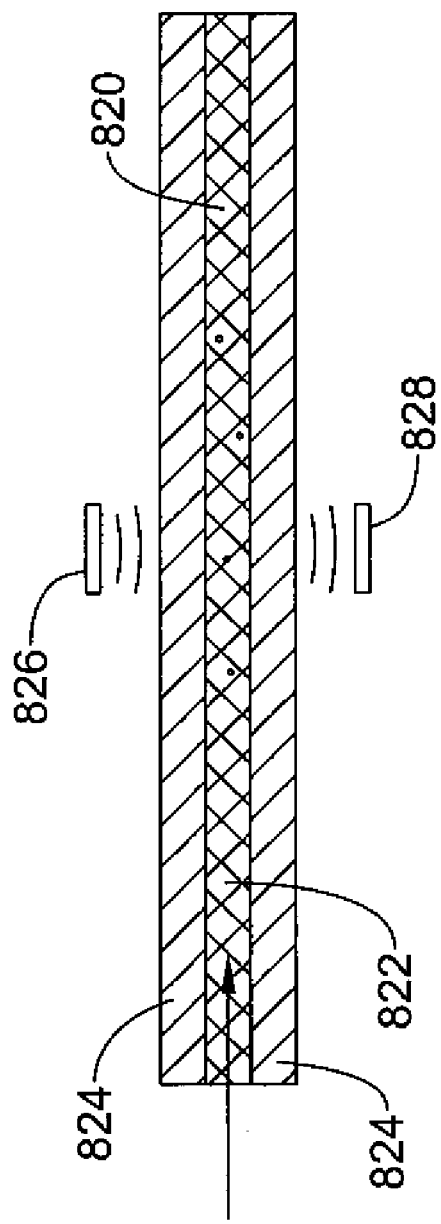
FIG. 18 is a schematic diagram of another illustrative example that may be useful in identifying when a sample fluid in a flow channel has one or more bubbles or other undesirable particles.

FIG. 18 is an illustrative example that may be useful for identifying when a sample fluid in a flow channel has one or more bubbles or other undesirable particles. In this illustrative example, a sample fluid 820 is present in a flow channel 822 defined by channel walls 824 of, for example, a fluidic cartridge. An ultrasound transducer 826 and an ultrasound receiver 828 are provided adjacent to the flow channel 822. In some cases, the ultrasound transducer 826 is provided on one side of the flow channel 822 and the ultrasound receiver 828 is provided on the opposite side. In other cases, the ultrasound transducer 826 and the ultrasound receiver 828 are provided on the same side of the flow channel 822. In either case, the ultrasound receiver 828 may be used to detect scatter in the ultrasound signal emitted by the ultrasound transducer 826 caused by bubbles or other undesirable particles in the fluid sample 820. When so detected, the sample analyzer may not provide a result, and in some cases, may provide an error message or error code.

Figure 19:
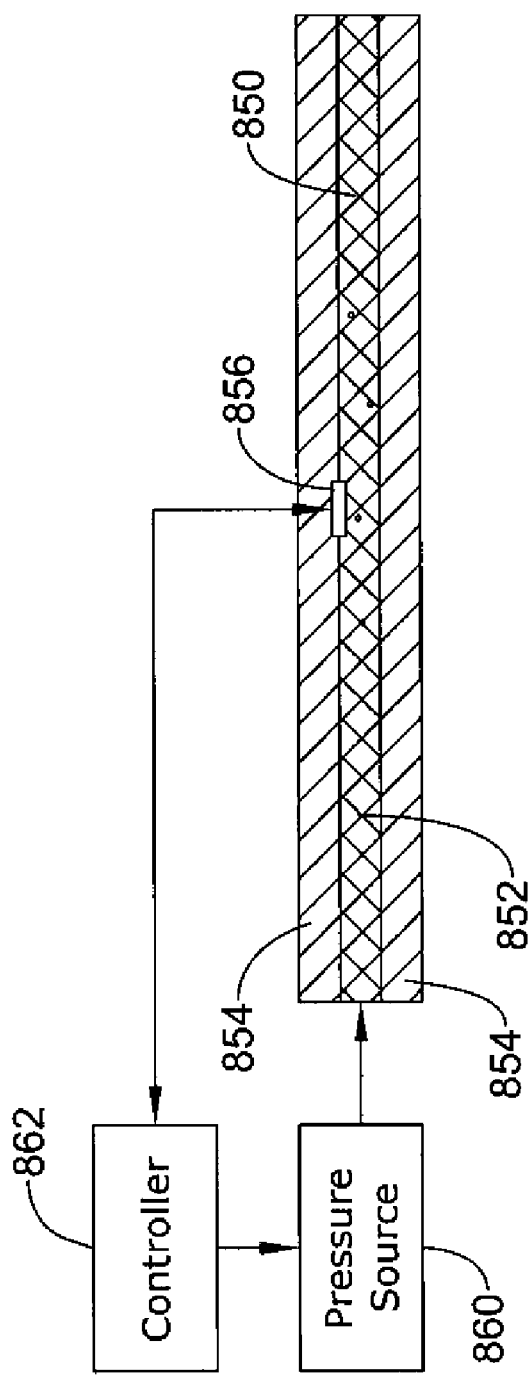
FIG. 19 is a schematic diagram of an illustrative example that may be useful in identifying when a sample fluid in a flow channel has one or more bubbles or other undesirable characteristics.

FIG. 19 is another illustrative example that may be useful for identifying when a sample fluid in a flow channel has one or more bubbles or other undesirable characteristics. In this illustrative example, a sample fluid 850 is present in a flow channel 852 defined by channel walls 854 of, for example, a fluidic cartridge. A flow sensor 856 is provided in fluid communication with the flow channel 852 to detect the flow rate of the sample fluid 850. The flow sensor(s) may be, for example, a thermal anemometer type flow sensor and/or a microbridge type flow sensor. Microbridge flow sensors are described in, for example, U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 5,050,429, all of which are hereby incorporated by reference.

A pressure source 860 may provide a variable pressure to the sample fluid 850 in the flow channel 852. A controller 862 may receive a flow rate signal from the flow sensor 856, and in some cases, may control the pressure source 860. In one illustrative example, and to detect bubbles in the sample fluid, the controller 862 may cause the pressure source 860 to suddenly change the pressure that is applied to the sample fluid 850. The resulting flow rate change in the sample fluid 850 may then be monitored by the flow sensor 856.

Figure 20:
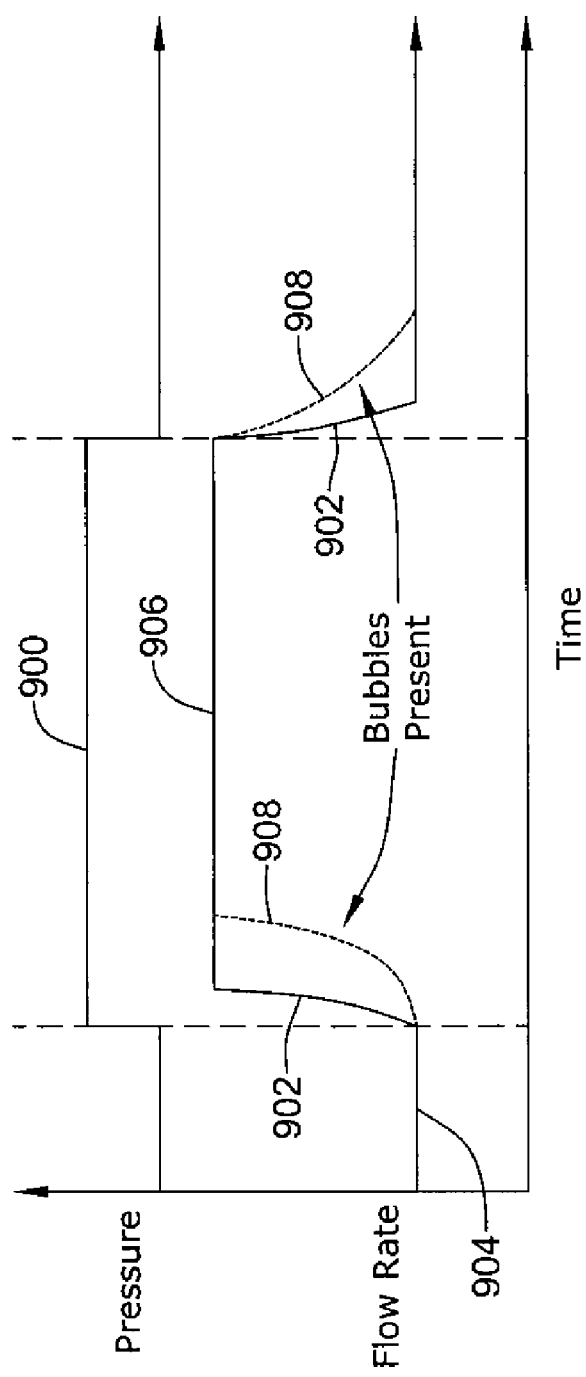
FIG. 20 is a graph showing an illustrative pressure pulse 900 that may be provided by the pressure source to the sample fluid in the flow channel of FIG. 19.

FIG. 20 is a graph showing an illustrative pressure pulse 900 that may be provided by pressure source 860 to the sample fluid 850 in the flow channel 852 of FIG. 19. With little or no bubbles present in the sample fluid 850, the flow rate shown at 902 may result. The flow rate 902 more rapidly increases from a lower flow rate value 904 to a higher flow rate value 906 when the pressure pulse 900 suddenly increases, and then rapidly decreases from the higher flow rate value 906 to the lower flow rate value 904 when the pressure pulse 900 suddenly decreases. However, when bubbles are present in the sample fluid 850, the resulting flow rate 908 (shown in dashed lines) may more gradually increase from the lower flow rate value 904 to the higher flow rate value 906 when the pressure pulse 900 suddenly increases, and may more gradually decrease from the higher flow rate value 906 to the lower flow rate value 904 when the pressure pulse 900 suddenly decreases. The air in the bubbles may, for example, increase the compressibility of the sample fluid 850, thereby resulting in the more gradual increase and decrease in the flow rate change. By monitoring the flow rate change during changes in applied pressure, the presence of bubbles in the sample fluid 850 may be detected. If a sufficient reduction in flow rate change is detected, the sample analyzer may not provide a result, and in some cases, may provide an error message or error code.

It is contemplated that the pressure source 860 may be any suitable pressure source including a conventional pump, a compressed air source, or any other suitable pressure source, as desired. In some cases, the pressure source 860 may be a higher frequency pressure source such as a piezoelectric vibrator, an ultrasonic transducer or any other type of high frequency pressure source. In some cases, the high frequency pressure source may be used in conjunction with a conventional pump or other pressure source, and may operate in parallel therewith. That is, a conventional pump or other pressure source 860 may be used to actually move the sample fluid through the flow channel 852 of the fluidic cartridge during analysis of a sample fluid. The high frequency pressure source may not be used to significantly move the sample fluid along the flow channel, but rather may be used to create higher frequency pressure pulses in the sample fluid to detect certain parameters of the sample fluid including, for example, the presence of bubbles, the compressibility of the sample fluid, and so on. The compressibility of the sample fluid may be used to help determine if the sample fluid 850 in the flow channel 852 is an expected sample fluid type, and if it is not, the sample analyzer may not provide a result, and in some cases, may provide an error message or error code.

In any event, and in some cases, when the high frequency pressure source operates simultaneously or in parallel with a conventional pump or other pressure source, in-situ monitoring of the sample fluid may be provided during sample processing by the fluidic circuit.

Figure 21:
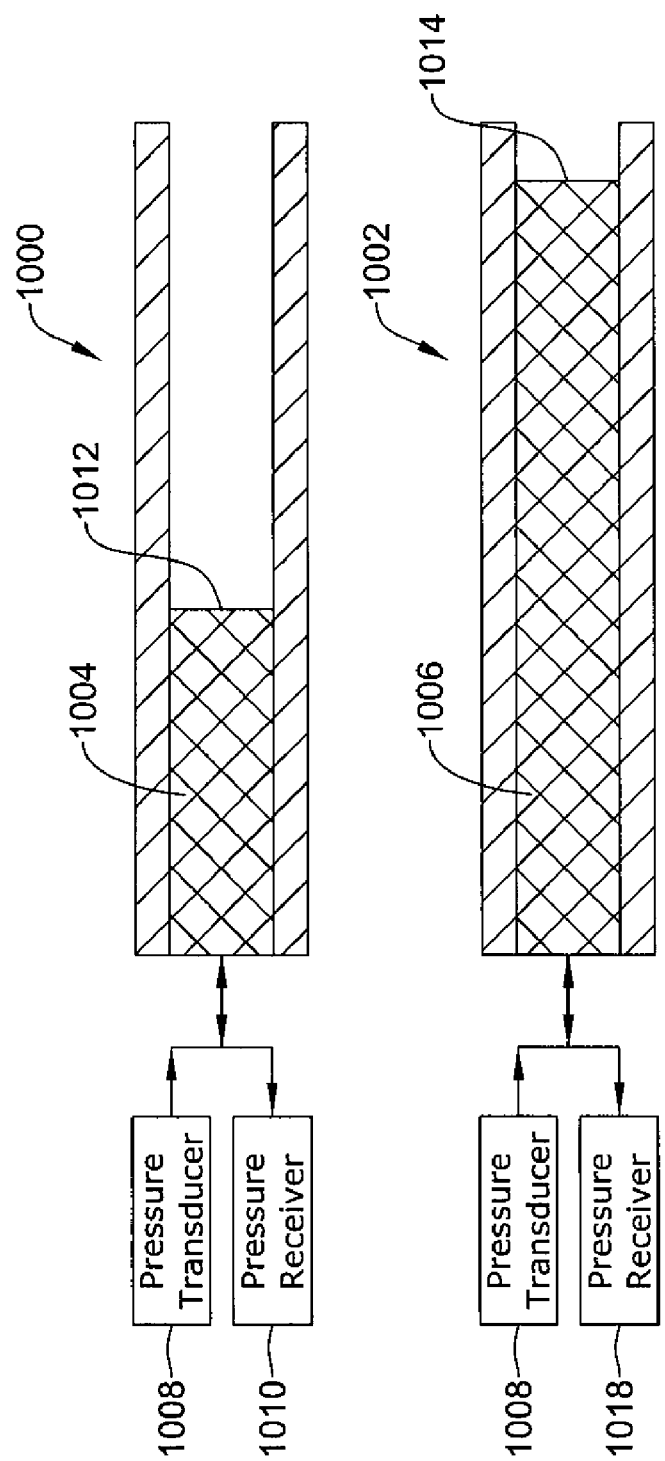
FIG. 21 is a schematic diagram of an illustrative example that may be helpful in determining or estimating the location of a terminal or distal end of a sample fluid in a flow channel of a fluidic circuit.

In some cases, a pressure pulse may be used to determine or estimate the location of a terminal or distal end of a sample fluid in a flow channel of a fluidic circuit. FIG. 21 shows one such illustrative example. In FIG. 21, two flow channels 1000 and 1002 are shown. A sample fluid 1004 is present in flow channel 1000 and a sample fluid 1006 is present in flow channel 1002. A pressure transducer (e.g., pressure source) 1008 and a pressure receiver (e.g., pressure sensor) 1010 are shown fluidly coupled to the sample fluid 1004 at a known location relative to the flow channel 1000. The pressure transducer 1008 may produce a pressure pulse in the sample fluid 1004. The pressure pulse travels down the sample fluid 1004 to the terminal end 1012. Some of the energy from the pressure pulse will be reflected by the terminal end 1012 of the sample fluid 1004 back to the pressure receiver 1010. The distance that the terminal end 1012 is currently located from the pressure transducer 1008 and/or pressure receiver 1010 is related to the time required for the pressure pulse to travel down the sample fluid 1004 to the terminal end 1012 and back to the pressure receiver 1010. Thus, by measuring the time required for the pressure pulse to travel to the terminal end 1012 and back to the pressure receiver 1010, the location of the terminal end 1012 along the flow channel 1000 may be determined.

The flow channel 1002 is similar to flow channel 1000, except that the terminal end is location a further distance down the flow channel. Thus, assuming that sample fluid 1006 is the same as sample fluid 1004, the time required for the pressure pulse to travel to the terminal end 1014 and back to the pressure receiver 1018 will be greater than that for flow channel 1000. Also, the reflected pressure pulse that is received by pressure receiver 1018 may have a reduced amplitude relative to the amplitude of the pressure pulse that is received by the pressure receiver 1010. Thus, monitoring the amplitude may provide another way to estimate or determine the location of the terminal ends 1012 and 1014 along flow channels 1000 and 1002, respectively.

Figure 22:
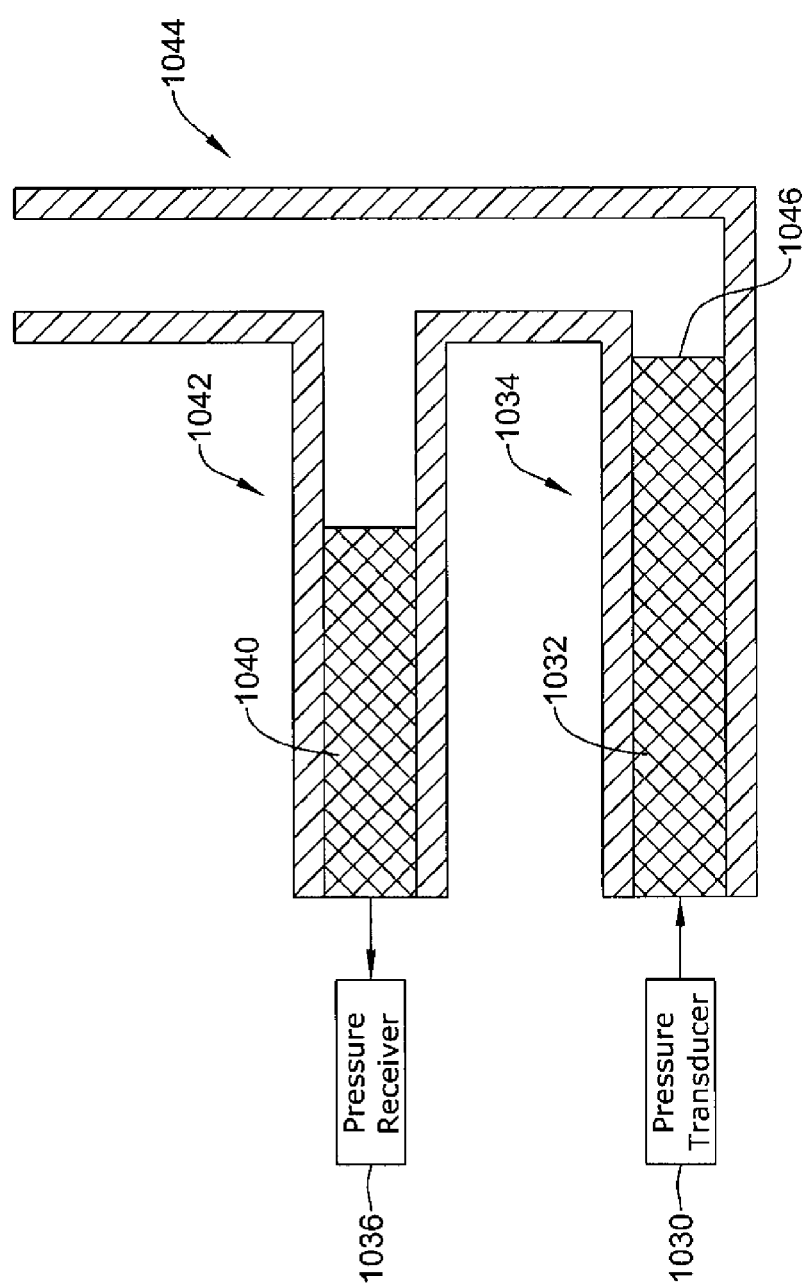
FIGS. 22-23 are schematic diagrams of an illustrative example that may be useful in determining when two or more fluids come together downstream in a fluid circuit.
Figure 23:
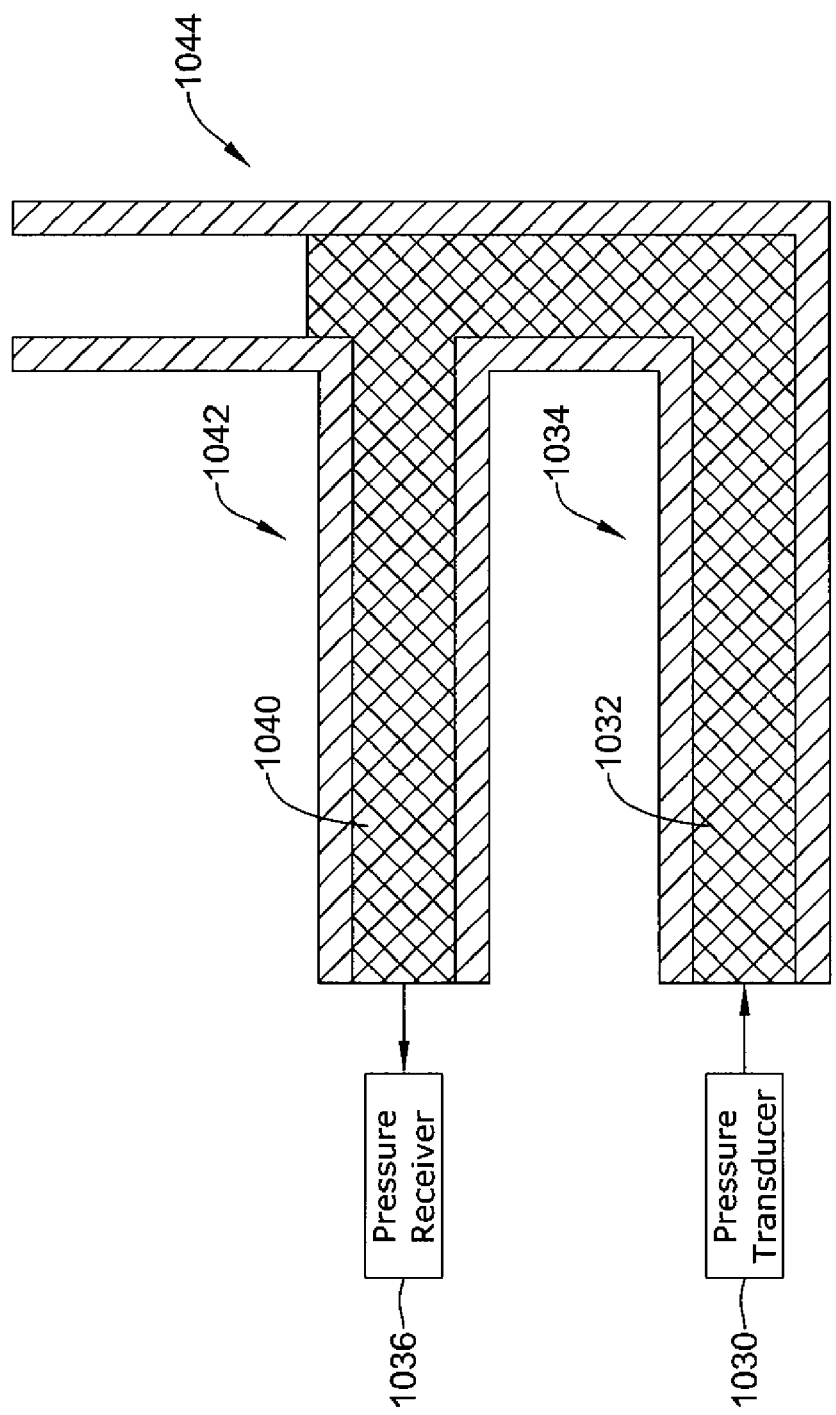

FIGS. 22-23 show an illustrative approach for determining when two fluids come together in a fluidic circuit. In many sample analyzers, different fluids are initially provided down different flow channels. Within the fluidic circuit, however, the various fluids are often intermixed. For example, a blood sample and a sphering reagent may each be initially provided down separate flow channels, but subsequently mixed together somewhere downstream in the fluid circuit. The timing of when and how the various fluids come together can be important to the overall function of a sample analyzer as disclosed in, for example, U.S. patent application Ser. No. 10/932,662, which is assigned to the assignee of the present invention and hereby incorporated by reference.

To help determine when two or more fluids come together downstream in a fluid circuit, a pressure transducer may be used to create a pressure pulse in at least one of the fluid samples. For example, and with reference to FIG. 22, a pressure transducer 1030 (e.g., a pump, a piezoelectric vibrator, an ultrasonic transducer or any other type of pressure transducer), may produce a pressure pulse in sample fluid 1032 in a first flow channel 1034. A pressure receiver 1036 (e.g., pressure sensor, ultrasound receiver, and so forth) may be in fluid communication with a sample fluid 1040 in a second flow channel 1042. The first flow channel 1034 and the second flow channel 1042 may come together at flow channel 1044, as best shown in FIG. 23.

Referring back to FIG. 22, the pressure pulse produced by the pressure transducer 1030 in the first sample fluid 1032 may travel down the first sample fluid 1032, but may not significantly extend past the terminal or distal end 1046 of the first sample fluid 1032. In the illustrative example, the flow channel 1044 shown FIG. 22 initially is filled with air or other gas, which is subsequently displaced by the sample fluids 1032 and 1040 when the sample fluids 1032 and 1040 are pushed down their respect flow channels 1034 and 1042. Before the sample fluids 1032 and 1040 come together, the pressure receiver 1036 may not receive a significant pressure pulse, or a significantly attenuated pressure pulse, from the pressure transducer 1030.

One or more pressure sources (not shown), such as pumps or the like, may be activated to move the sample fluids 1032 and 1040 along their respect flow channels 1034 and 1042 until the sample fluids 1032 and 1040 come together, as better shown in FIG. 23. When this occurs, a pressure pulse produced by pressure transducer 1030 may now more freely travel to the pressure receiver 1036. Thus, it can be determined when the sample fluids 1032 and 1040 come together by monitoring when the pressure receiver 1036 begins to receive, or receives a less attenuated, pressure pulses from the pressure transducer 1030.

In some cases, the pressure transducer 1030 may produce a pressure pulse train (sometimes of relatively high frequency) in the sample fluid, and may operate simultaneously or in parallel with a pump or other pressure source that actually moves the sample fluids 1032 and 1040 along the flow channels 1034, 1042 and 1044 of the fluidic circuit. Thus, the pressure transducer 1030 may be used to provide in-situ monitoring of the sample fluids in the fluidic circuit, and more specifically, when the sample fluids 1032 and 1040 come together downstream.

In some cases, the operation of the sample analyzer may be affected when the sample analyzer is not placed on a level surface during an analysis. To detect this case, it is contemplated the sample analyzer may include a level sensor. In one illustrative example, the level sensor may be a Micro Tilt Sensor (D6B), available from Omron Corporation. Other level sensor may include a ball sensor with electrical outputs. Using a level sensor, the sample analyzer may determine if the sample analyzer is sufficiently level to perform an analysis. If the sample analyzer is not sufficiently level, the sample analyzer may not perform an analysis and/or not provide a result, and in some cases, may provide an error message or error code.

Another approach for checking to see if the sample analyzer is sufficiently level includes depressurizing one or more flow channels that include a fluid, and measure a flow rate of the fluid in the one or more flow channels. If the sample analyzer is not sufficiently level, gravity may cause the flow rates in the one or more flow channels to be outside of an expected range. If the flow rates are outside of the expected range, the sample analyzer may be deemed to be not sufficiently level, and the sample analyzer may not perform an analysis and/or not provide a result, and in some cases, may provide an error message or error code.

In some cases, the operation of the sample analyzer may be affected when the sample analyzer is bumped or otherwise moved during an analysis. To detect this case, it is contemplated the sample analyzer may include a shock and/or vibration sensor. In one illustrative example, the shock and/or vibration sensor may be a Shock/Vibration Sensor (D7E-2), available from Omron Corporation. Using the shock and/or vibration sensor, the sample analyzer may determine if the sample analyzer has been bumped or otherwise moved. If the sample analyzer has been sufficiently bumped, the sample analyzer may require that the user run a control card, or a calibration card, to verify the proper operation of the sample analyzer before proceeding. In some cases, the sample analyzer may determine if the sample analyzer has been bumped or otherwise moved during an analysis. If the sample analyzer has been sufficiently bumped during an analysis, the sample analyzer may not provide a result, and in some cases, may provide an error message or error code.

Figure 24:
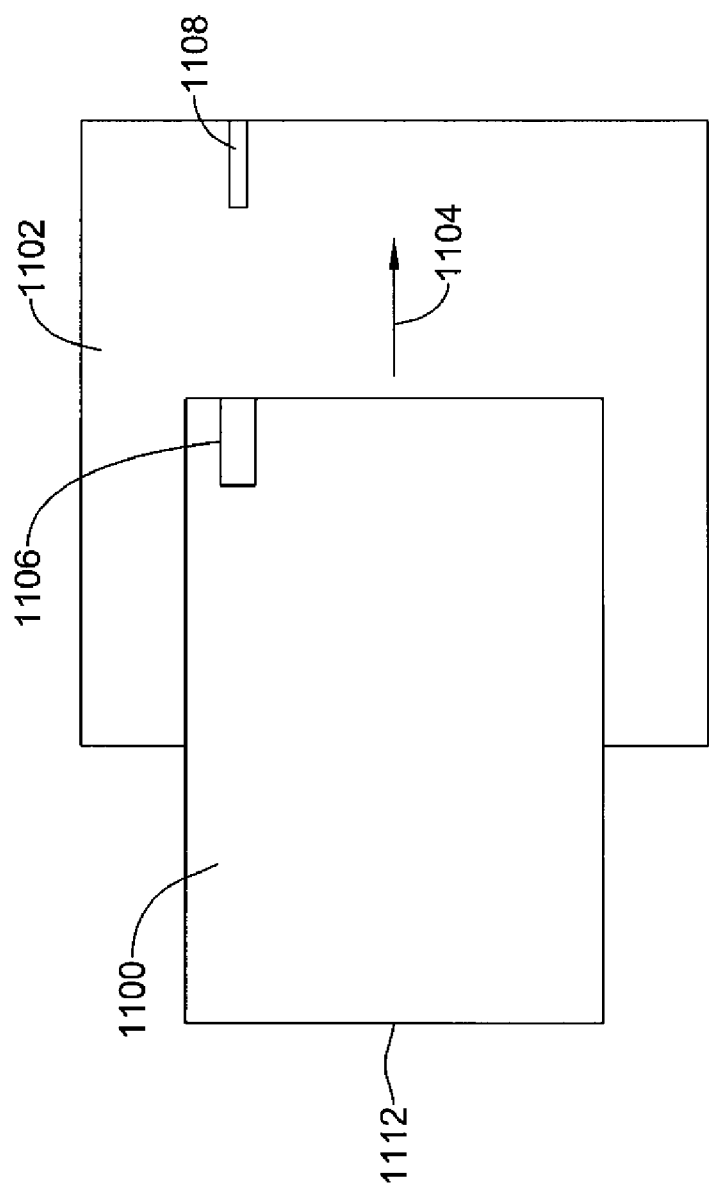
FIG. 24 is a schematic diagram of an illustrative instrument and cartridge, wherein the cartridge and instrument are keyed to only allow the cartridge to be inserted into the instrument in a proper orientation.

In some cases, the sample analyzer may include an instrument and a removable and/or disposable cartridge. Because the behavior of the user is sometimes unpredictable, it may be desirable to verify that the cartridge is inserted properly into the instrument before proceeding with an analysis. One way to accomplish this is to design the cartridge and the instrument such that the cartridge can only be inserted into the instrument in the correct orientation. For example, FIG. 24 shows a cartridge 1100 that is received by a slot in an instrument 1102, as indicated by arrow 1104. The illustrative cartridge 1100 includes a groove 1106 in the top surface of the cartridge 1100. The instrument includes a corresponding male member 1108 that is adapted to extend into the groove 1106 when the cartridge 1100 is inserted in the proper orientation relative to the instrument 1102. If the cartridge 1100 is inserted upside down, the groove 1106 and the male member 1108 will not line up, and the cartridge 1100 will be prevented from being fully inserted into the slot of the instrument 1102. Likewise, if end 1112 of cartridge 1100 is inserted into the slot of the instrument 1102, the groove 1106 and the male member 1108 will not line up, and the cartridge 1100 will be prevented from being fully inserted into the slot of the instrument 1102. This is just one example of having the cartridge 1100 keyed to the instrument 1102 so that the cartridge 1100 can only be inserted into the instrument 1102 in the proper orientation.

The orientation of the cartridge relative to the instrument may be verified in any number of ways, particularly if the cartridge is not keyed relative to the instrument. For example, in some examples, one or more pressure ports may extend between the instrument and cartridge when the cartridge is properly inserted into the instrument. The instrument may apply pressure to one or more of the pressure ports and check to see if the desired flows are observed. If the pressure ports of the instrument are not lined up with the pressure ports of the cartridge, the desired flows may not be seen. If the desired flows rates are not seen, the sample analyzer may not perform an analysis and/or not provide a result, and in some cases, may provide an error message or error code.

In another example, the cartridge may include one or more optical windows or other optical structures. The instrument may optically interrogate the location(s) that would include the one or more optical windows or other optical structures if the cartridge were properly installed in the instrument. If an expected optical response is not detected, the cartridge may not be installed in the proper orientation, and the sample analyzer may not perform an analysis and/or not provide a result, and in some cases, may provide an error message or error code.

In some cases, the sample analyzer may require one or more reagents to perform a desired sample analysis. It may be desirable to determine if the proper reagents are present, and that the reagents are in good condition. In one illustrative example, a reagent may be delivered in a container, and the container may include a bar or other code that identifies various parameters of the reagent. The various parameters may, for example, identify the reagent type, the date of manufacture, the expiration date for the reagent, and other parameters. The sample analyzer may include a bar or other code reader, and may read the various parameters. The sample analyzer may then determine, for example, if the reagent is the proper reagent for the desired sample analysis, whether the reagent is beyond the specified expiration date, and so on. If the reagent is not the correct reagent for the desired analysis, or is not in good condition, the sample analyzer may not perform the analysis and/or not provide a result, and in some cases, may provide an error message or error code.

Figure 25:
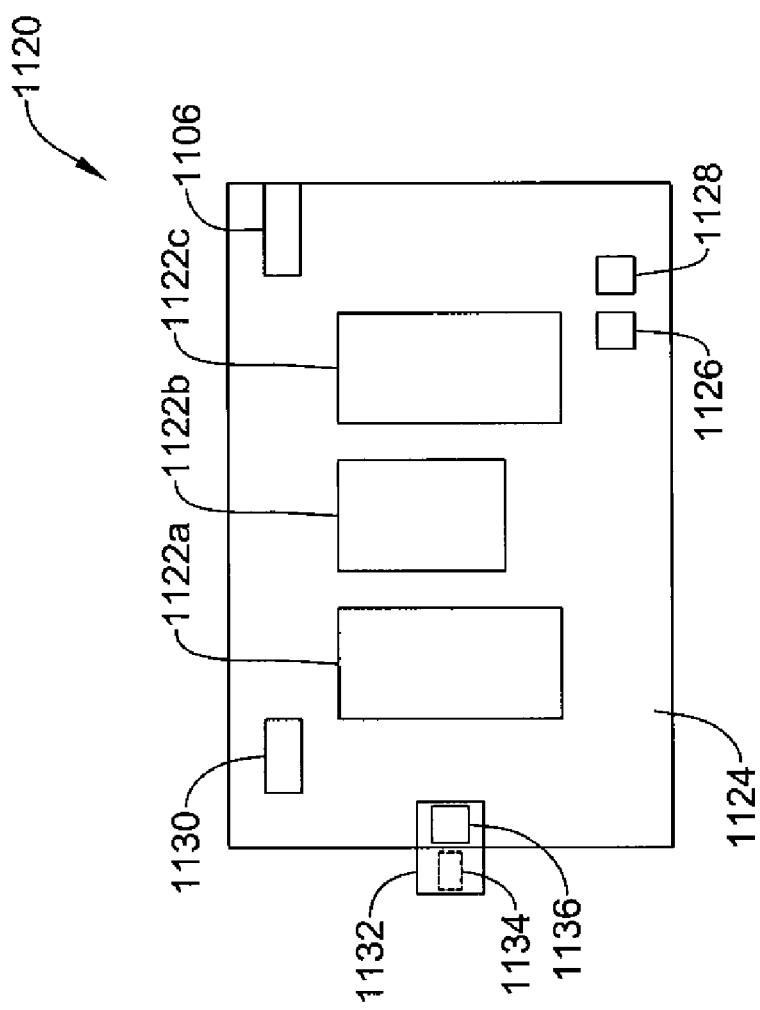
FIG. 25 is a schematic diagram of an illustrative cartridge.

In some cases, the reagents may be stored on a removable and/or disposable cartridge. FIG. 25 shows a disposable cartridge 1120 that includes three chambers 1122a, 1122b and 1122c, each for storing a reagent that is specific for the analysis that is to be performed using the cartridge 1120. A bar code 1124 is shown affixed to the cartridge 1120. Once the cartridge is properly inserted into a corresponding instrument, the instrument may read the bar code, and determine if the reagents are the proper reagents for the desired sample analysis, whether the reagents are beyond their specified expiration date, and so on.

The bar code 1124 may also identify a number of parameters related to the cartridge 1120. For example, the bar code 1124 may identify the cartridge, the analysis type(s) supported by the cartridge, cartridge specific calibration parameters if any, timing parameters for the analysis, input pressures and/or flow rates for the analysis, and so forth. In some cases, the bar code 1124 may also provide software for use by the instrument when performing an analysis with the cartridge. Rather than providing a bar code 1124, or in addition to providing a bar code 1124, an RFID tag may be provided and the instrument may include a mechanism for reading the RFID tag. The RFID tag can include similar information as described above with respect to the bar code 1124

Temperature may also affect the performance of some reagents. In some cases, a maximum temperature indicator 1126 and/or a minimum temperature indicator 1128 may be provided. The minimum temperature indicator 1128 may be similar to the freeze indicator available from JP Labs. The freeze indicator provided by JP labs is in the form of a label that can be easily affixed to a cartridge or other container. When the temperature of the freeze indicator is lowered below the freezing point of water, it undergoes an irreversible color change, e.g., blue-to-red. The instrument may include an optical interrogator that detects the color of the freeze indicator 1128, and if the reagents have been exposed to a temperature that is below a minimum temperature, the sample analyzer may not perform the analysis and/or not provide a result, and in some cases, may provide an error message or error code.

Likewise, the maximum temperature indicator 1126 may be similar to the temperature indicator available from JP Labs. These indicators undergo a color change when certain predetermined temperature (or temperature range), usually above room temperature, is reached. When heated, they change from colorless-to-red, colorless-to-green, blue-to-red, and so on. These indicators can be easily incorporated into commercially available ink vehicles, e.g., flexo and gravure. The instrument may include an optical interrogator that detects the color of the temperature indicator 1126, and if the reagents have been exposed to a temperature that is above a maximum temperature, the sample analyzer may not perform the analysis and/or not provide a result, and in some cases, may provide an error message or error code.

Humidity and/or moisture indicators may also be provided. The humidity and/or moisture indicators may be similar to those available from JP Labs. The humidity and/or moisture indicators may undergo a color change with total exposure to moisture. The time required for the color change can be varied from a few minutes to a few weeks under normal ambient humidity.

The illustrative cartridge 1120 may also include a time indicator 1130. In some examples, the cartridge 1120 may be shipped to the user in a sealed package. The sealed package may provide a controlled environment around the cartridge 1120. Before use, the user must remove the cartridge 1120 from the package, thereby exposing the cartridge 1120 to the outside environment. The time indicator 1130 may be activated when the package is opened, and may turn color or otherwise provide a detectable condition after a predetermined period of time has expired. The time indicator 1130 may be similar to the time indicator available from JP Labs.

The instrument may include an optical interrogator that detects the color of the time indicator 1130, and if the time period has expired, the sample analyzer may not perform the analysis and/or not provide a result, and in some cases, may provide an error message or error code. This may give the user a predetermined amount of time to open the cartridge package, load a blood or other sample into the cartridge 1120, and perform an analysis via the instrument. This may help reduce the chance that the user loads a sample into the cartridge 1120, and then waits too long before performing the analysis, thereby allowing the sample to coagulate, dry out, or otherwise change characteristics.

Rather than initiating a time indicator when the cartridge 1120 is removed from a package, a strip of tape 1132 or other material may be provided over the sample input port 1134 of the cartridge 1120. The strip of tape 1132 or other material may cover up a time indicator 1136. Prior to loading the sample into the cartridge, the user must remove the strip of tape 1132 or other material, which then exposes the time indicator to the environment and activates the time indicator. After a predetermined period of time, the time indicator 1136 may change color or otherwise provide a detectable condition.

The instrument may include an optical interrogator that detects the color of the time indicator 1136, and if the time period has expired, the sample analyzer may not perform the analysis and/or not provide a result, and in some cases, may provide an error message or error code. This may give the user a predetermined amount of time to remove the strip of tape 1132 or other material from the sample input port, load a blood or other sample into the cartridge 1120, and perform an analysis via the instrument. This may help reduce the chance that the user loads a sample into the cartridge 1120, and then waits too long before performing the analysis, thereby allowing the sample to coagulate, dry out, or otherwise change characteristics.

Figure 26:
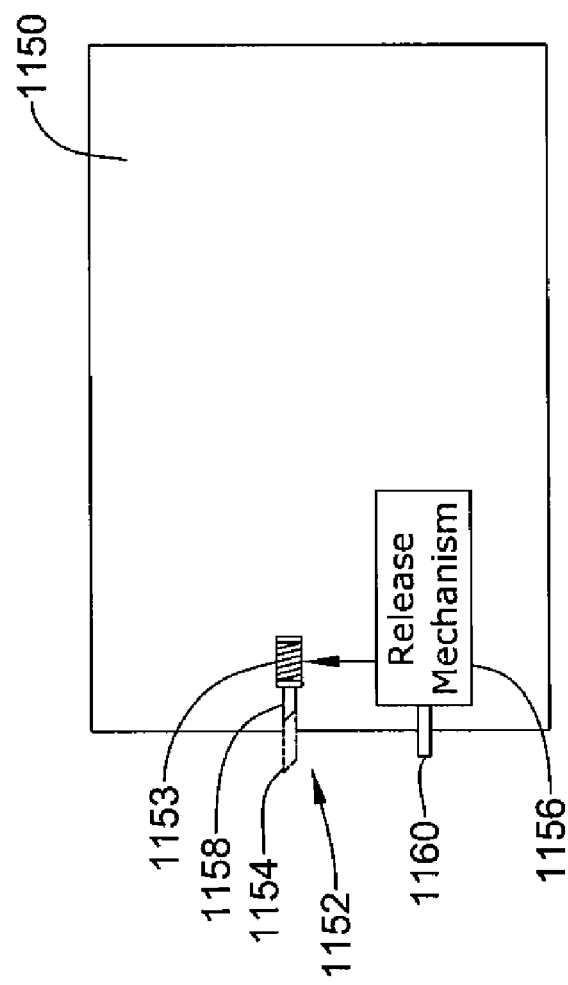
FIG. 26 is a schematic diagram of an illustrative cartridge that includes a spring activated lancet.

In some cases, a cartridge may include a spring activated lancet to aid in blood sample collection to the cartridge. For example, FIG. 26 shows an illustrative cartridge 1150 that includes a spring activated lancet 1152. The spring activated lancet 1152 may include a spring or other biasing element 1153 that bias the lancet in an extended position 1154. A release mechanism 1156 may be coupled to the spring activated lancet 1152 to lock the lancet in a retracted position 1158. When a release button or lever 1160 is actuated by a user, the release mechanism 1156 may release the spring activated lancet 1152, and the lancet may suddenly move from the retracted position 1158 to the extended position 1154. If the user's finger is positioned against the cartridge 1150 when the release button or lever 1160 is activated, the spring activated lancet 1152 may pierce the user's skin and draw an appropriate amount of blood. The spring activated lancet 1152 may be in fluid communication with a sample collection capillary (not shown) in the cartridge 1150, and thus in some examples, the blood sample may be directly delivered to the sample collection capillary of the cartridge 1150. The spring activated lancet 1152, release mechanism 1156 and release button or lever 1160 may be similar to the BD™ Lancet Device, available from Becton, Dickinson and Company.

Alternatively, a sample may be transferred from, for instance, a pricked finger via a pipette (possibly coated with an anti-coagulant) to the sample input or capillary of the cartridge. A syringe may be used for sample transfer and introduction to the cartridge. An alcohol swab may be used to prep the finger before a prick, lance or cut to the finger. A lancet with a dial-in depth setting may be used, such as lancet 1152 of cartridge 1150 in FIG. 26.

Figure 27:
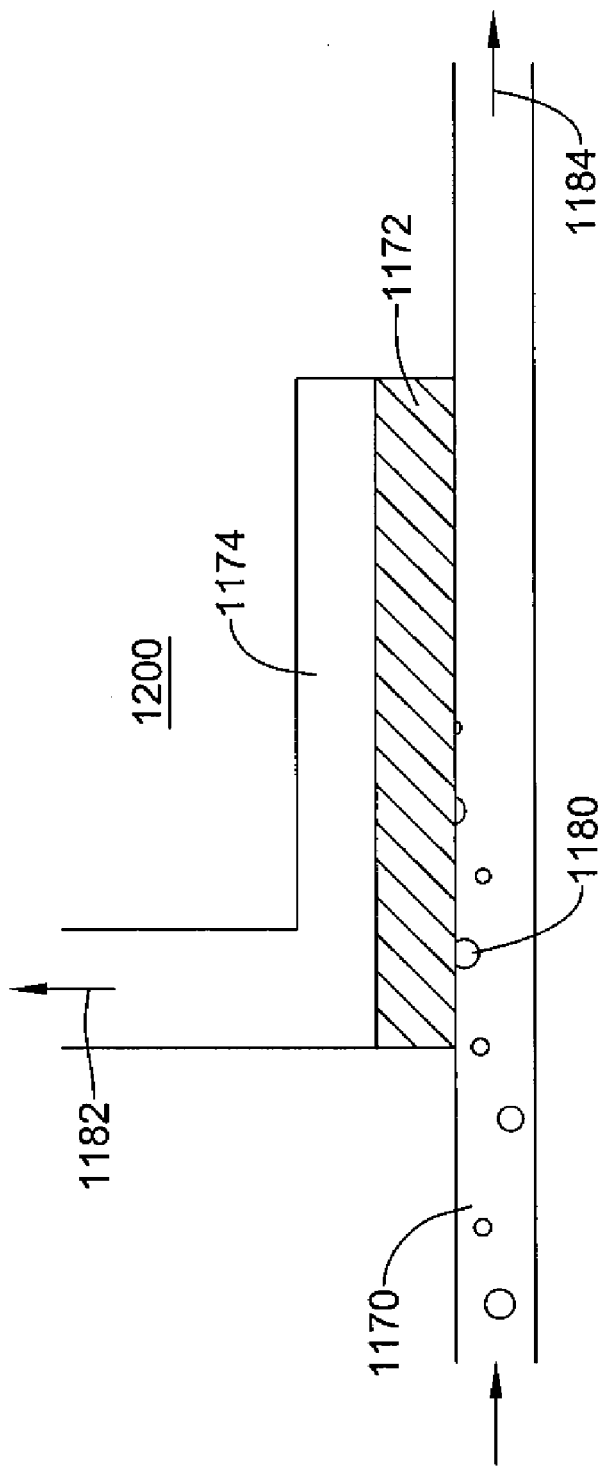
FIG. 27 is a schematic diagram of an illustrative cartridge having a membrane for remove bubbles from a flow channel.

In some cases, and referring to FIG. 27, a removable and/or disposable cartridge 1200 may include a mechanism to remove bubbles from a flow stream. In some cases, bubbles can be removed from liquid flow in a flow channel as they pass under a porous membrane that forms part of a wall of the flow channel. In FIG. 27, a bubbly liquid is shown flowing down a flow channel 1170. A membrane 1172 separates the flow channel 1170 from a vent chamber 1174. The vent chamber 1174 is held at a lower pressure than the pressure in the flow channel 1170. In some cases, the membrane is a hydrophobic membrane, such as the Fluoropore™, Mitex™ or Durapore™ membrane available from Millipore Corporation in Billerica, Mass. The Mitex™ membrane is made from PTFE and comes with pore sizes of 5 or 10 microns. The Fluoropore™ membrane is made from PTFE with HDPE support, and comes with pore sizes of 1 or 3 microns. The Durapore™ membrane is made from Polyvinylidene fluoride, and comes with pore sizes of 0.1, 0.22 and 0.45 microns. Hydrophobic membranes can often sustain higher pressure differentials without leaking fluid therethrough.

The pressure differential between the flow channel 1170 and vent chamber 1174 forces the gas in the bubbles 1180 through the membrane 1172 and out vent 1182, resulting in substantially reduced bubbles (desirably bubble free) in the liquid downstream of the membrane 1172. The bubble free liquid may then flow downstream as shown at 1184 for further processing by fluidic circuit on the removable and/or disposable cartridge.

Larger pore sizes require less pressure differential than smaller pore sizes to achieve the same flow rate of gas from the trapped bubbles 1180, but are unable to sustain as much pressure differential without allowing some of the liquid to pass therethrough. It is estimated that a membrane having one (1) micron pores should be able to sustain a pressure differential on the order of one (1) PSI, depending on the surface energies of the liquid and membrane and pore geometry.

Figure 28:
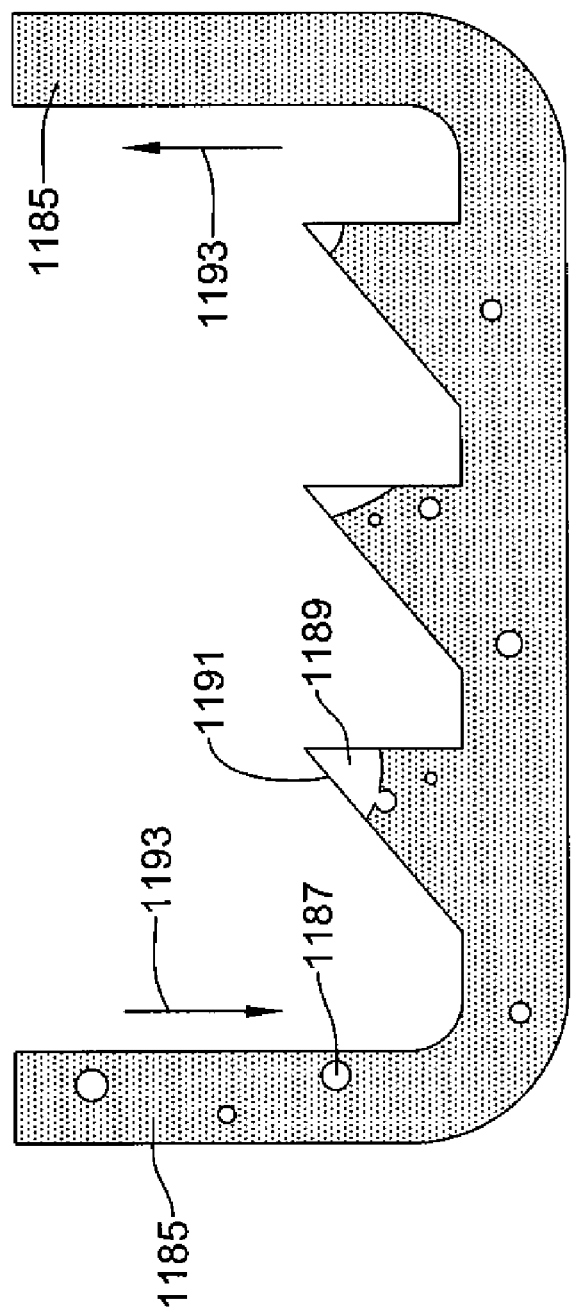
FIG. 28 is a schematic diagram of an illustrative example of a bubble trap in a flow channel.

FIG. 28 is schematic diagram of an illustrative example of a bubble trap 1191 on a side wall in a flow channel 1185. The bubbles 1187 may move along with a flow 1193 into one or more traps 1191, congregate and coalesce with a bubble 1189 already in the trap; or a bubble 1191 may become an initial bubble 1189 in a trap. The trap may be a deformation, such as a triangular hook, in a wall of the flow channel where bubbles may be caught as they pass by and not be able to flow out of the trap back into the flow stream. Besides being triangular as shown, the trap shape may also be rectangular, hemispherical, and so forth.

In some examples, the sample analyzer may have electronics and/or software for controlling the various components of the sample analyzer. In some cases, the sample analyzer may be powered by line voltage, but may have a battery backup in case of power loss. The electronics may also include a clock chip, sometimes with battery backup, to maintain an accurate time and date. Having an accurate time and date may be useful in, for example, comparing an expiration date of a reagent that might be read from a bar code or the like on the reagent package or cartridge, to determine if the reagent is still usable.

If power is lost during an analysis, and no battery backup is provided, the electronics and/or software may terminate the analysis, not issue a result, and in some cases, issue an error message or error code to the user.

The electronics and/or software may be coupled to various light sources and detectors of the sample analyzer. In some examples, the electronics and/or software may check the operation of the light sources and light detectors before, after and/or periodically or throughout a sample analysis. For example, the electronics and/or software may verify that the one or more detectors are detecting light provided by corresponding light sources before, after and/or periodically or throughout a sample analysis.

Alternatively, or in addition, irregularities in the cartridge, such as cracks in an optical window or dirt or debris on the optical window, may be identified after a cartridge is inserted into an instrument, but before an analysis procedure begins. This may be accomplished by, for example, activating one or more light sources to provide light through the optical window and detecting the optical profile (reflectance, scatter, FALS, SALS, LALS, and so forth) using one or more detectors. If the optical window includes cracks, dirt or debris on the optical window, or other irregularities, these irregularities may cause an unexpected optical profile at the detectors. If the electronics and/or software detect such irregularities, the sample analyzer may not perform the analysis and/or not provide a result, and in some cases, may provide an error message or error code. Unclean optics might be remedied with a swab.

If flow sensors are present in the sample analyzer, certain electronics and/or software may monitor the output of the flow sensors before, after or during an analysis, to confirm that the indicated flow rate(s) are within a desired range or fall along a desired profile. If the electronics and/or software detect that the indicated flow rate(s) do not fall within a desired range or do not fall along a desired profile, the sample analyzer may not perform the analysis and/or not provide a result, and in some cases, may provide an error message or error code.

In some cases, the sample analyzer may include some level of built-in-self-test (BIST). For example, in a test mode, some or all of the storage elements (e.g., registers) in the electronics may be selectively connected together in a serial scan chain, where test vectors can be serially scanned into the chained registers. In some cases, the inputs and outputs of the electronics may include a test register that is logically inserted only in the test mode. A functional clock cycle may be initiated, wherein the test vectors bits are released through the logic between registers, and the results are captured by the registers. The results may then be serially scanned out of the registers and compared to an expected result. This may provide robust testing of the electronics in the sample analyzer.

Many of such test vectors may be executed to achieve a desired fault coverage. In some cases, the fault coverage may be greater than 50 percent of the logic, greater than 60 percent of the logic, greater than 80 percent of the logic, greater than 90 percent of the logic, greater than 95 percent of the logic, or greater than 99 percent of the logic, as desired. Once tested, the electronics may be switched back into a functional mode, wherein normal functional operation of the sample analyzer may resume. The sample analyzer may automatically enter the test mode at periodic intervals, such as once an hour, once a day, once a week, once a month or any other desired interval, as desired.

In some cases, the electronics and/or software is designed and/or tested to provide a Mean-Time-Between-Failure (MTBF) of greater than 5,000 hours, greater than 8,000 hours, greater than 10,000, greater than 50,000 hours, greater than 100,000 hours or more, depending on the application.

In some examples, the sample analyzer may be connected to a remote site or sites via the internet. When so provided, test results may be delivered to the remote site for long term storage and/or further analysis, if desired. In addition, it is contemplated that the remote site may include diagnostic software that is capable of perform remote diagnostics and/or maintenance of the sample analyzer. In some cases, the remote site may automatically upgrade the firmware or software of the sample analyzer.

Card rejects and other errors may be sent to the remote site. The remote site may determine if a particular sample analyzer is experiencing unusually high errors. Unusually high errors may indicate a failed or marginal hardware component in the sample analyzer, and a service person may be dispatched from the remote site to fix/replace the component before the users detect the problem. Unusually high errors at a particular location may also indicate that the users at that location may need additional training. Such training can be dispatched from the remote site for laboratory personnel. The cartridge and instrument may be designed so that it is operable by untrained personnel.

The remote site may also statistically analyze the errors and/or BIST results from multiple sample analyzers and identify components, software or other areas of the sample analyzer that could be enhanced in subsequent versions of the sample analyzer.

The temperature, humidity and other environmental parameters in or around the sample analyzer may be periodically sensed and sent to the remote site, as well as impact, tilt and other sensor data, as desired.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A sample analyzer comprising:
an instrument having a slot; and
a cartridge including a flow channel, the cartridge configured to be inserted into the slot;
a light source positioned on a first side of the flow channel proximate to the cartridge when inserted in the slot; and
a detector positioned on the first side of the flow channel proximate to the cartridge when inserted in the slot; and
wherein:
the flow channel comprises a channel wall;
the channel wall has a first index of refraction;
a sample fluid in the flow channel has a second index of refraction;
the light source is for projecting light into the flow channel; and
the detector is configured to detect light reflected from an interface of the first and second indices of refraction and the light detected by the detector is indicative of the index of refraction of the fluid.

2. The analyzer of claim 1, wherein:
if the index of refraction of the fluid is not within a specified range, then the sample analyzer may not perform an analysis, not provide a result, indicate an incorrect fluid, and/or provide an error indication.

3. The analyzer of claim 1, wherein the channel wall is thin enough to permit optical tunneling if a delta between the first and second indices of refraction is within a range for the fluid to be satisfactory.

4. The analyzer of claim 1, wherein if the index of refraction of the fluid is not within the specified range the fluid may be a incorrect specimen or sample, have an incorrect reagent, bubbles, clots, contaminants, and/or the like.

5. The analyzer of claim 1, wherein:
the detector is for detecting light going through the channel wall and the fluid and out of the channel through the channel wall;
the light to the detector is indicative of an index of refraction of the fluid; and
if the index of refraction of the volume is not within a specified range for an appropriate sample fluid, then the sample analyzer may not perform an analysis, not provide a result, indicate an incorrect sample fluid, and/or provide an error indication.

6. A sample analyzer comprising:
an instrument having a slot, an energy source and a detector; and a cartridge, having at least one flow channel, for insertion into the slot;

wherein:

the energy source and detector are positioned on a same side of the flow channel and adjacent to the flow channel; and the detector is configured to detect a property of a fluid in the flow channel indicative of undesirable particles or bubbles in the fluid in the flow channel.

7. The analyzer of claim 6, wherein:

the energy source is for providing light through the flow channel at an angle relative to a wall of the flow channel;

the detector is for detecting a magnitude of scattered light from the flow channel;

a magnitude of a certain range is indicative of undesirable particles or bubbles in a fluid in the flow channel; and if the magnitude of the certain range is detected, then the analyzer may not provide a result or may provide an error indication.

8. The analyzer of claim 6, wherein:

the energy source is an ultrasound transducer, adjacent to the flow channel, for transmitting ultrasound into the flow channel;

the detector is an ultrasound receiver, adjacent to the flow channel, for receiving reflected ultrasound energy from the flow channel;

reflected ultrasound energy having a magnitude of a certain range is indicative of bubbles or other undesirable particles in the flow channel; and if reflected ultrasound energy having a magnitude of a certain range is received by the ultrasound receiver, then the analyzer would not provide a result and/or would provide an error indication.

9. The analyzer of claim 6, wherein:

the energy source is a pressure source for applying a certain change of pressure to a sample fluid in the flow channel;

the detector is a flow sensor, situated in the flow channel, for monitoring a flow rate in the flow channel;

a flow rate of the sample fluid is monitored by the flow sensor while a certain change of pressure is applied by the pressure source to the fluid in the flow channel;

a flow rate change per unit of time for the certain change of pressure indicates an amount of compressibility of the sample fluid; and the amount of compressibility of a specific range is indicative of bubbles in the sample fluid.

10. The analyzer of claim 9, wherein the pressure source is a high frequency pulse piezoresistive pressure source.

11. The analyzer of claim 9, if bubbles are indicated to be in the sample fluid in the flow channel, the analyzer will not provide a result and/or will provide an error indication.

12. The analyzer of claim 6, wherein:

the energy source is a pressure transducer for transmitting a pressure pulse in a sample fluid in the flow channel, at a first location along the flow channel to a terminal end of the sample fluid;

the detector is a pressure receiver for receiving the pressure pulse reflected by the terminal end of the fluid, at a second location along the flow channel; and a duration of time between transmitting a pressure pulse down the flow channel and receiving the reflected pulse is indicative of a location of the terminal end along the flow channel relative to the first and second locations.

13. The analyzer of claim 6, wherein:

the energy source is a pressure transducer for transmitting a pressure pulse in a sample fluid in the flow channel, at a first location along the flow channel to a terminal end of the sample fluid;

the detector is a pressure receiver for receiving the pressure pulse reflected by the terminal end of the fluid, at a second location along the flow channel; and a duration of time between transmitting a pressure pulse down the flow channel and receiving the reflected pulse is indicative of a location of the terminal end along the flow channel relative to the first and second locations.

14. The analyzer of claim 6, wherein:

the energy source is a pressure transducer for transmitting a pressure pulse in a first fluid in a first flow channel;

the detector is a pressure receiver for receiving the pressure pulse from a second fluid in a second flow channel;

a first fluid having a terminal end is in the first flow channel;

a second fluid having a terminal end is in the second flow channel; and if a pressure pulse is produced in the first fluid by the pressure transducer, a significant pressure pulse signal will appear at the pressure receiver upon a meeting of the terminal ends of the first and second fluids.

\* \* \* \* \*